US008357683B2

(12) United States Patent
Shenk et al.

(10) Patent No.: US 8,357,683 B2
(45) Date of Patent: *Jan. 22, 2013

(54) COMPOUNDS FOR ENZYME INHIBITION

(75) Inventors: Kevin D. Shenk, Palo Alto, CA (US); Francesco Parlati, San Francisco, CA (US); Han-jie Zhou, Foster City, CA (US); Catherine Sylvain, San Mateo, CA (US); Mark S. Smyth, Foster City, CA (US); Mark K. Bennett, Moraga, CA (US); Guy J. Laidig, Menlo Park, CA (US)

(73) Assignee: Onyx Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/328,909

(22) Filed: Dec. 16, 2011

(65) Prior Publication Data

US 2012/0088762 A1    Apr. 12, 2012

Related U.S. Application Data

(63) Continuation of application No. 12/708,753, filed on Feb. 19, 2010, now Pat. No. 8,080,545, which is a continuation of application No. 11/820,490, filed on Jun. 19, 2007, now Pat. No. 7,691,852.

(60) Provisional application No. 60/815,218, filed on Jun. 19, 2006.

(51) Int. Cl.
*A61K 31/5377* (2006.01)
*A61K 31/427* (2006.01)
*A61K 31/404* (2006.01)
*A61K 31/336* (2006.01)
*C07D 413/12* (2006.01)
*C07D 417/12* (2006.01)
*C07D 405/12* (2006.01)
*C07D 303/38* (2006.01)

(52) U.S. Cl. ............ 514/231.5; 514/365; 514/414; 514/475; 544/147; 548/204; 548/467; 549/548

(58) Field of Classification Search .............. 514/231.5, 514/414, 475, 365; 548/467, 204; 549/548; 544/147

See application file for complete search history.

(56) References Cited

U.S. PATENT DOCUMENTS

| | | | |
|---|---|---|---|
| 4,733,665 A | 3/1988 | Palmaz | |
| 4,990,448 A | 2/1991 | Konishi et al. | |
| 5,071,957 A | 12/1991 | Konishi et al. | |
| 5,134,127 A | 7/1992 | Stella et al. | |
| 5,135,919 A | 8/1992 | Folkman et al. | |
| 5,340,736 A | 8/1994 | Goldberg | |
| 5,376,645 A | 12/1994 | Stella et al. | |
| 5,441,944 A | 8/1995 | Weisz et al. | |
| 5,723,492 A | 3/1998 | Chandrakumar et al. | |
| 5,756,764 A | 5/1998 | Fenteany et al. | |
| 5,874,418 A | 2/1999 | Stella et al. | |
| 6,046,177 A | 4/2000 | Stella et al. | |
| 6,075,150 A | 6/2000 | Wang et al. | |
| 6,099,851 A | 8/2000 | Weisman et al. | |
| 6,133,248 A | 10/2000 | Stella | |
| 6,133,308 A | 10/2000 | Soucy et al. | |
| 6,150,415 A | 11/2000 | Hammock et al. | |
| 6,204,257 B1 | 3/2001 | Stella et al. | |
| 6,235,717 B1 | 5/2001 | Leban et al. | |
| 6,294,560 B1 | 9/2001 | Soucy et al. | |
| 6,410,512 B1 | 6/2002 | Mundy et al. | |
| 6,462,019 B1 | 10/2002 | Mundy et al. | |
| 6,492,333 B1 | 12/2002 | Mundy | |
| 6,613,541 B1 | 9/2003 | Vaddi et al. | |
| 6,617,309 B2 | 9/2003 | Tung et al. | |
| 6,656,904 B2 | 12/2003 | Mundy et al. | |
| 6,660,268 B1 | 12/2003 | Palombella et al. | |
| 6,740,674 B2 | 5/2004 | Klimko et al. | |
| 6,781,000 B1 | 8/2004 | Wang et al. | |
| 6,794,516 B2 | 9/2004 | Soucy et al. | |
| 6,831,099 B1 | 12/2004 | Crews et al. | |
| 6,838,252 B2 | 1/2005 | Mundy et al. | |
| 6,838,436 B1 | 1/2005 | Mundy et al. | |
| 6,849,743 B2 | 2/2005 | Soucy et al. | |
| 6,884,769 B1 | 4/2005 | Mundy et al. | |
| 6,902,721 B1 | 6/2005 | Mundy et al. | |
| 7,232,818 B2 | 6/2007 | Smyth et al. | |
| 7,388,017 B2 | 6/2008 | Tung et al. | |
| 7,417,042 B2 | 8/2008 | Smyth et al. | |
| 7,491,704 B2 | 2/2009 | Smyth et al. | |
| 7,687,456 B2 | 3/2010 | Zhou et al. | |
| 7,691,852 B2 * | 4/2010 | Shenk et al. ............ 514/231.5 |
| 7,737,112 B2 | 6/2010 | Lewis et al. | |
| 8,080,576 B2 * | 12/2011 | Shenk et al. ............ 514/414 |
| 8,129,346 B2 | 3/2012 | Smyth et al. | |
| 2002/0103127 A1 | 8/2002 | Mundy et al. | |
| 2002/0107203 A1 | 8/2002 | Mundy et al. | |

(Continued)

FOREIGN PATENT DOCUMENTS

EP    0 411 660    2/1991
EP    1 136 498    9/2001

(Continued)

OTHER PUBLICATIONS

"Definition of Cancer," [Retrieved from] http://www.medterms.com, 1 page [retrieved on Sep. 16, 2005].
Acharyya et al., "Cancer cachexia is regulated by selective targeting of skeletal muscle gene products" JCI 114:370-378, 2004.
Adams et al., "Proteasome Inhibitors: A Novel Class of Potent and Effective Antitumor Agents," Cancer Research, 1999, 59:2615-2622.
Adams, "The development of proteasome inhibitors as anticancer drugs," Cancer Cell, May 2003, 5:417-421.
Adams, Cancer Drug Discovery and Development, Protease Inhibitors in Cancer Therapy, 2004. Human Press, Chapter 20, Phase I trials, pp. 271-282.

(Continued)

*Primary Examiner* — Kristin Bianchi
(74) *Attorney, Agent, or Firm* — Fish & Richardson P.C.

(57) ABSTRACT

One aspect of the invention relates to inhibitors that preferentially inhibit immunoproteasome activity over constitutive proteasome activity. In certain embodiments, the invention relates to the treatment of immune related diseases, comprising administering a compound of the invention. In certain embodiments, the invention relates to the treatment of cancer, comprising administering a compound of the invention.

22 Claims, 2 Drawing Sheets

U.S. PATENT DOCUMENTS

| | | |
|---|---|---|
| 2002/0111292 A1 | 8/2002 | Mundy et al. |
| 2003/0224469 A1 | 12/2003 | Buchholz et al. |
| 2003/0236223 A1 | 12/2003 | Wagner et al. |
| 2004/0097420 A1 | 5/2004 | Palombella et al. |
| 2004/0106539 A1 | 6/2004 | Schubert et al. |
| 2004/0116329 A1 | 6/2004 | Epstein |
| 2004/0138153 A1 | 7/2004 | Ramesh et al. |
| 2004/0171556 A1 | 9/2004 | Purandare et al. |
| 2004/0254118 A1 | 12/2004 | He et al. |
| 2004/0266664 A1 | 12/2004 | Crews et al. |
| 2005/0025734 A1 | 2/2005 | Garrett et al. |
| 2005/0101781 A1 | 5/2005 | Agoulnik et al. |
| 2005/0245435 A1 | 11/2005 | Smyth et al. |
| 2005/0256324 A1 | 11/2005 | Laidig et al. |
| 2006/0030533 A1 | 2/2006 | Smyth et al. |
| 2006/0088471 A1 | 4/2006 | Bennett et al. |
| 2006/0128611 A1 | 6/2006 | Lewis |
| 2006/0241056 A1 | 10/2006 | Orlowski et al. |
| 2007/0105786 A1 | 5/2007 | Zhou et al. |
| 2007/0207950 A1 | 9/2007 | Yao et al. |
| 2007/0212756 A1 | 9/2007 | Greene et al. |
| 2008/0090785 A1 | 4/2008 | Smyth et al. |
| 2009/0105156 A1 | 4/2009 | Phiasivongsa et al. |
| 2009/0131421 A1 | 5/2009 | Smyth et al. |
| 2009/0156473 A1 | 6/2009 | Schubert |
| 2009/0182149 A1 | 7/2009 | Kawahara et al. |
| 2009/0203698 A1 | 8/2009 | Zhou et al. |
| 2009/0215093 A1 | 8/2009 | Bennett et al. |
| 2010/0144648 A1 | 6/2010 | Shenk et al. |
| 2010/0144649 A1 | 6/2010 | Shenk et al. |

FOREIGN PATENT DOCUMENTS

| | | |
|---|---|---|
| WO | WO 91/13904 | 9/1991 |
| WO | WO 94/15956 | 7/1994 |
| WO | WO 95/24914 | 9/1995 |
| WO | WO 96/13266 | 5/1996 |
| WO | WO 96/32105 | 10/1996 |
| WO | WO 98/010779 | 3/1998 |
| WO | WO 00/02548 | 1/2000 |
| WO | WO 00/61167 | 10/2000 |
| WO | WO 01/28579 | 4/2001 |
| WO | WO 03/059898 | 7/2003 |
| WO | WO 2005/105827 | 11/2005 |
| WO | WO 2005/111008 | 11/2005 |
| WO | WO 2005/111009 | 11/2005 |
| WO | WO 2006/017842 | 2/2006 |
| WO | WO 2006/045066 | 4/2006 |
| WO | WO 2006/086600 | 8/2006 |
| WO | WO 2006/099261 | 9/2006 |
| WO | WO 2007/056464 | 5/2007 |
| WO | WO 2007/067976 | 6/2007 |
| WO | WO 2007/149512 | 12/2007 |
| WO | WO 2008/140782 | 11/2008 |
| WO | WO 2009/045497 | 4/2009 |
| WO | WO 2010/036357 | 4/2010 |
| WO | WO 2010/048298 | 4/2010 |
| WO | WO 2010/145376 | 4/2010 |

OTHER PUBLICATIONS

Altun et al., "Effects of PS-341 on the Activity and Composition of Proteasomes in Multiple Myeloma Cells" Cancer Res 65:7896, 2005.

Almond et al. "The proteasome: a novel target for cancer chemotherapy" Leukemia, 16(4), 433-443, Apr. 2002.

Alves et al. "Diels-alder reactions of alkyl 2H-azirine-3-carboxylates with furans", J. Chem. Soc. Perkin Trans, 1:2969-2976, 2001.

Arastu Kapur et al., "Nonproteasomal targets of the proteasome inhibitors bortezomib and carfilzomib: a link to clinical adverse events", Clin Cancer Res., 17:2734-43, 2011.

Argiriadi, "Binding of alkylurea inhibitors to epoxide hydrolase implicates active site tyrosines in substrate activation," J. Biol. Chem., 2000, 275(20):15265-15270.

Bao et al. "PR-39 and PR-11 peptides inhibit ischemia-reperfusion injury by blocking proteasome-mediated IκBα degradation" Am. J. Physiol. Heart Circ. Physiol. 281:H2612-H2618, 2001.

Benedetti et al., "Versatile and Stereoselective Synthesis of Diamino Diol Dipeptide Isosteres, Core Units of Pseudopeptide HIV Protease Inhibitors," J. Org. Chem., 1997, 62:9348-9353.

Berge et al. "Pharmaceutical Salts", J. Pharm. Sci. 66(1), 1-19. Jan. 1977.

Bernier et al. "A Methionine aminopeptidase-2 Inhibitor, PPI-2458, for the treatment of reheumatoid arthritis", PNAS 101(29):10768-73, Jul. 20, 2004.

Bis et al. "Defining & Addressing Solid-State Risks After the Proof-of-Concept Stage of Pharmaceutical evelopment," Drug Development & Delivery, pp. 32-34, 2011.

Boccadoro et al. "Preclinical evaluation of the proteasome inhibitor bortezomib in cancer therapy", Cancer Cell International, 5(18), Jun. 1, 2005.

Bogyo et al. "Substrate binding and sequence preference of the proteasome revealed by active-site-directed affinity probes", Chemistry & Biology, 5(6)307-320, Jun. 1998.

Bogyo et al. "Biochemistry", PNAS 94:6629-6634, 1997.

Bougauchi et al., "Catalytic Asymmetric Epoxidation of .alpha., .beta.-Unsaturated Ketones Promoted by Lanthanoid Complexes," J. Am. Chem. Soc., 1997, 119:2329-2330.

Brinkley, Michael "A Brief Survey of Methods for Preparing Protein Conjugates with Dyes, Haptens, and Cross-Linking Reagents", Bioconjug. Chem 3:2-13, 1992.

Brittain et al. "Physical Characterization of Pharmaceutical Solids," Pharmaceutical Research, 8(8):963-973, 1991.

Brown et al., "Selective Reductions. 37. Asymmetric Reduction of Prochiral Ketones with .beta.-(3-Pinanyl)-9-borabicyclo[3.3.1]nonane," J. Org. Chem., 1985, 50:1384-1394.

Caira, "Crystalline Polymorphism of Organic Compounds," Topics in Current Chemistry, 1998, 198:163-208.

Cascio et al., "26S proteasomes and immunoproteasomes produce mainly N-extended versions of an antigenic peptide", EMBO J, 20:2357-2366, 2001.

Center for Drug Evaluation and Research, Application No. 21-602, Medical Review, Clinical NDA Review, "NDA 21-602 VELCADE™ (bortexomib) for injection," Clinical Review, 1-34, 2006.

Center for Drug Evaluation and Research, Application No. 21-602, Medical Review, Clinical NDA Review, "NDA 21-602 VELCADE™ (bortexomib) for injection," Clinical Review, 1-47, 2006.

Center for Drug Evaluation and Research, Application No. 21-602, Medical Review, Clinical NDA Review, "NDA 21-602 VELCADE™ (bortexomib) for injection," Clinical Review, 81-125, 2006.

Ciechanover, "The Ubiquitin-Proteasome Proteolytic Pathway," Cell, 1994, 79:13-21.

Cohen, "AIDS Mood Upbeat—For a Change," Science, 1995, 267:959-960.

Collins, Tucker, "Endothelial nuclear factor-κβ and the initiation of the atherosclerotic lesion", Lab. Invest. 68(5), 499-508, 1993.

Concise Encyclopedia Chemistry, 1993, p. 490.

Corey et al., "A General, Catalytic, and Enantioselective Synthesis of .alpha.-Amino Acids," J. Am. Chem. Soc., 1992, 114:1906-1908.

Corey et al., "Highly Enantioselective Borane Reduction of Ketones Catalyzed by Chiral Oxazaborolidines. Mechanism and Synthetic Implications," J. Am. Chem. Soc., 1987, 109:5551-5553.

Craiu et al. "Lactacystin and clasto-lactacystin β-lactone modify multiple proteasome β-subunits and inhibit intracellular protein degradation and major hisotcompatibility complex class I antigen presentation" J. of Biol. Chem. 272(20), 13437-13445, May 16, 1997.

Datta et al., "A Stereoselective Route to Hydroxyethylamine Dipeptide Isosteres," J. Am. Chem. Soc., 2000, 65:7609-7611.

Demo et al., "Antitumor Activity of PR-171, a Novel Irreversible Inhibitor of the Proteasome," Cancer Research, 2007, 67(13):6383-6391.

Dess et al., "A Useful 12-I-5 Triacetoxyperiodinane (the Dess-Martin Periodinane) for the Selective Oxidation of Primary or Secondary Alcohols and a Variety of Related 12-I-5 Species," J. Am. Chem. Soc., 1991, 113:7277-7287.

Dess et al., "Readily Accessible 12-I-5 Oxidant for the Conversion of Primary and Secondary Alcohols to Aldehydes and Ketones," J. Org. Chem., 1983, 48:4155-4156.

Diaz-Hernandez et al., "Neuronal Induction of the Immunoproteasome in Huntington's Disease" J. Neurosci., 23:11653-1161, 2003.

Dobler, "Total synthesis of (+)-epopromycin B and its analogues-studies on the inhibition of cellulose biosynthesis," Tetrahedron Letters, 2001, 42(2):215-218.

Egerer et al., "Tissue-Specific Up-Regulation of the Proteasome Subunit beta5i (LMP7) in Sjogren's Syndrome" Arthritis Rheum 54:1501-8, 2006.

Elliott et al., "The Proteasome a New Target for Novel Drug Therapies," Am J Clin Pathol., 2001, 116:637-646.

Elofsson et al., "Towards subunit-specific proteasome inhibitors: synthesis and evaluation of peptide .alpha.',.beta.'-epoxyketones," Chemistry & Biology, 1999, 6:811-822.

European Search Report, EP 08 16 4241, completed Jan. 22, 2009, 5 pages.

European Search Report, EP 09 00 6228, completed Aug. 25, 2009, 7 pages.

Favit et al. "Prevention of β-Amyloid Neurotoxicity by Blockade of the Ubiquitin-Proteasome Protealytic Pathway", Journ of Neurochemistry, 75(3):1258-1263, 2000.

"FDA mulls drug to slow late-stage Alzheimers[Online], [retrieved on Sep. 23, 2003]. Retrieved from the internet, U RL: hyyp;1 www.cnn.com/2003/HEALTH/conditions/09/24/alzheimers.drug. ap/index. html>".

Fenteany et al. "A β-lactone related to lactacystin induces neurite outgrowth in a neuroblastoma cell line and inhibits cell cycle progression in an osteosarcoma cell line", PNAS 91:3358-3362, Apr. 1994.

Figueiredo-Pereira et al., The Antitumor Drug Aclacinomycin A, Which Inhihits the Degradation of Ubiquitinated Proteins, Shows Selectivity for the Chymotrypsin-like Activity of the Bovine Pituitary 20 S Proteasome, The Journal of Biological Chemistry, 271(2):16455-16459, Jul. 1996.

First Vitality (2008, updated) Alzheimer's & Senile Dementia, http://www.1stvitality.co.uk/health/alzheimers/.
carnosine_proteasomal_alzheimers.htm, p. 1, 2008.

Fox et al. "Organic Chemistry", Publisher: Jones & Bartlett Pub, Published Jun. 15, 2004, Sec. 5-6, pp. 177-178, ISBN-10: 0763721972, ISBN-13: 9780763721978.

Gan et al., "Identification of Cathepsin B as a Mediator of Neuronal Death Induced by A-activated Microglial Cells Using a Functional Genomics Approach" J. Biol. Chem. 279:5565-5572, 2004.

Gao et al. "Inhibition of ubiquitin-proteasome pathway-mediated IκBα degradation by a naturally occurring antibacterial peptide" J. Clin. Invest. 106:439-448, 2000.

Garcia-Echeverria, "Peptide and Peptide-Like Modulators of 20S Proteasome Enzymatic Activity in Cancer Cells", International J. of Peptide Res. and Ther., 12(1):49-64, Mar. 1, 2006.

Garrett et al., "Selective inhibitors of the osteoblast proteasome stimulate bone formation in vivo and in vitro," J Clinical Investigation, 2003, 111:1771-1782.

Golub et al., "Molecular Classification of Cancer: Class Discovery and Class Prediction by Genes Expression Monitoring," Science, 1999, 286:531-537.

Gonzales et al. "Pain relief in chronic pancreatitis by pancreatico-jejunostomy. An institutional experience" Arch. Med. Res. 28(3), 387-390, 1997.

Gordon et al. "1207 Results of study PX-171-007 a phase 1b/2 study of carfilzomib, a selective proteasome inhibitor, in patients with selected advanced metastatic solid tumors" Eur. Journ. of Cancer. Supplement, 7(2):122-123, Sep. 2009.

Graz University of Technology, "Database of Fluorescent Dyes Properties and Applications" WWW.Fluorophonres.org, 33 pgs, Exhibit B to response filed with US Patent office on Sep. 16, 2008 for U.S. Appl. No. 11/254,541 (now abandoned).

Green et al. "Protective Groups in Organic Synthesis", 2nd ed., Wiley & Sons, Inc., New York (1991).

Griffith et al. "Molecular recognition of angiogenesis inhibitors fumagillin and ovalicin by methionine aminopeptidase", PNAS 95:15183-88, Dec. 1998.

Groettrup et al. "Selective proteasome inhibitors: modulators of antigen presentation?", Drug Discovery Today, 4(2):63-71, Feb. 1999.

Groll et al., "Crystal Structure of Epoxomicin:20S Proteasome Reveals a Molecular Basis for Selectivity of r¢,â¢-Epoxyketone Proteasome Inhibitors," J. Am. Chem. Soc. 2000, 122:1237-1238.

Gura, "Systems for Identifying New Drugs Are Often Faulty," Science, Nov. 7, 1997, 278(5340):1041-1042.

Hanada et aL, "Epoxomicin, A New Antitumor Agent of Microhial Origin", The Journal of Antihiotics, 45(11):1746-1752, Nove 1992.

Hanson et al., "Synthesis of New Dipeptide Analogues Containing Novel Ketovinyl and Hydroxyethylidene Isosteres via Grignard Addition to Chiral .alpha.-Amino Aldehydes," J. Org. Chem., 1985, 50:5399-5401.

Harding et al., "Novel Dipeptide Aldehydes Are Proteasome Inhibitors and Block the MHC-1 Antigen-Processing Pathway," J. Immunology, 1995, 155:1767-1775.

Hardy, "The secret life of the hair follicle," Trends in Genetics, 1992, 8:55-61.

Harris et al. "Effects of transforming growth factor β on bone nodule formation and expression of bone morphogenetic protein 2, osteocalcin, osteopontin, alkaline phosphatase, and type I collagen mRNA in long-term cultures of fetal rat calvarial osteoblasts", J. Bone Miner. Res. 9(6), 855-863, 1994.

Haugland, Rosaria "Coupling of Monoclonal Antibodies with Fluorophores", Methods Mol. Biol. 45, 205-221, 1995.

Hawley's Condensed Chemical Dictionary, 1993, p. 594.

Hilfiker, Ed., Polymorphism in the Pharmaceutical Industry, 2006, pp. 12-15.

Hoffman et al., "Highly Stereoselective Syntheses of syn- and anti-1,2-Amino Alcohols," J. Org. Chem., 2002, 67:1045-1056.

Huff, Joel R., "HIV Protease: A Novel Chemotherapeutic Target for AIDS," Journal of Medicinal Chemistry, 34(8):2305-2314, Aug. 1991.

Holbeck et al.,"Analysis of Food and Drug Administration-Approved Anticancer Agents in the NC160 Panel of Human Tumor Cell Lines", Mol Cancer Ther, 9:1451-1460, May 4, 2010.

International Preliminary Report on Patentability for corresponding PCT Application No. PCT/US2005/012740, issued Oct. 19, 2006, 11 pgs.

International Preliminary Report on Patentability for corresponding PCT Application No. PCT/US2005/016335, issued Nov. 14, 2006, 11 pgs.

International Preliminary Report on Patentability for PCT/US2005/017000, issued Nov. 21, 2006, 12 pages.

International Preliminary Report on Patentability for PCT/US2005/028246, issued Feb. 6, 2007, 8 pages.

International Preliminary Report on Patentability for PCT/US2005/037966, issued Apr. 24, 2007, 12 pages.

International Preliminary Report on Patentability for PCT/US2005/044451, issued Jun. 13, 2007, 8 pages.

International Preliminary Report on Patentability for PCT/US2008/005997, issued Nov. 10, 2009, 7 pages.

International Preliminary Report on Patentability for PCT/US2008/011443, issued Apr. 7, 2010, 12 pages.

International Preliminary Report on Patentability PCT/US2007/014427, issued Dec. 22, 2008, 8 pages.

International Preliminary Report on Patentability for PCT/US2010/056395, mailed May 24, 2012, 10 pages.

International Search Report (Partial) ) for PCT/US2008/011443, dated Dec. 9, 2008, 6 pages.

International Search Report and Written Opinion for corresponding PCT Application No. PCT/US2005/012740, mailed Jan. 9, 2006, 16 pgs.

International Search Report and Written Opinion for corresponding PCT Application No. PCT/US2005/016335, mailed Jan. 2, 2006, 17 pgs.

International Search Report and Written Opinion for PCT/US2007/014427, mailed Dec. 3, 2007, 12 pages.

International Search Report and Written Opinion for PCT/US2010/056395, mailed Mar. 15, 2011, 10 pages.

International Search Report and Written Opinion for PCT/US2011/026629, mailed Jun. 30, 2011, 18 pages.

International Search Report and Written Opinion for PCT/US2011/031436, mailed Nov. 28, 2011, 5 pages.

International Search Report and Written Opinion of the Internatinal Searching Authority for PCT/US2010/028126, mailed Jun. 9, 2010, 13 pages.

International Search Report and Written Opinion of the International Searching Authority for PCT/US2005/017000, mailed Feb. 3, 2006, 12 pages.

International Search Report and Written Opinion of the International Searching Authority for PCT/US2005/028246, mailed Jan. 19, 2006, 11 pages.

International Search Report and Written Opinion of the International Searching Authority for PCT/US2005/037966, mailed Jan. 24, 2006, 17 pages.

International Search Report and Written Opinion of the International Searching Authority for PCT/US2005/044451, mailed May 2, 2006, 12 pages.

International Search Report and Written Opinion of the International Searching Authority for PCT/US2006/043503, mailed Feb. 19, 2007, 17 pages.

International Search Report and Written Opinion of the International Searching Authority for PCT/US2008/005997, mailed Nov. 7, 2008, 8 pages.

International Search Report and Written Opinion of the International Searching Authority for PCT/US2008/011443, mailed Mar. 25, 2009, 16 pages.

International Search Report for PCT/US2009/061498, mailed Dec. 10, 2009, 5 pages.

Iqbal et al. "Potent Inhibitors of Proteasome", J. Med Chem. 38:2276-2277, 1995.

Iqbal et al., "Potent .alpha.-ketocarbonyl and boronic ester derived inhibitors of proteasome," Bioorganic & Medicinal Chemistry Letters, 1996, 6:287-290.

Ivanisevic et al. ("Uses of X-Ray Powder Diffraction in the pharmaceutical Industry," Pharmaceutical Sciences Encyclopedia: Drug Discovery, Development, and Manufacturing, Edited by Shayne C. Gad, 2010, pp. 1-42.

Jacobsen et al., "Asymmetric Dihydroxylation via Ligand-Accelerated Catalysis," J. Am. Chem. Soc., 1988, 110:1968-1970.

Jain, "Delivery of Molecular Medicine to Solid Tumors," Science, 1996, 271(5252):1079-1080.

Jones et al., "Total Synthesis of the Immunosuppressant (−)-FK-506," J. Am. Chem. Soc., 1989, 111:1157-1159.

Jung et al. "Melatonin in cancer management: progress and promise" Cancer Res., 66(22):9789-9793, 2006.

Khan et al., "Immunoproteasomes Largely Replace Constitutive Proteasomes During an Antiviral and Antibacterial Immune Response in the Liver" J Immunol 5 167:6859-6868, 2001.

Kessler et al. "Extended peptide-based inhibitors efficiently target the proteasome and reveal overlapping specificities of the catalytic β-subunits", Chem & Biol. 8(9), 913-929, Aug. 8, 2001.

Kisselev et al., "Proteasome inhibitirs: from research tools to drug candidates", Chemistry and Bioloty, 8(8):739-758, 2001.

Kijima et al. "Trapoxin, an antitumor cyclic tetrapeptide, is an irreversible inhibitor of mammalian histone deacetylase" J. Biol. Chem. 268(30):22429-22435, 1993.

Kim et al., "Proteasome inhibition by the natural products epoxomicin and dihydroeponemycin: insights into specificity and potency," Bioorganic & Medicinal Chemistry Letters, 1999, 9:3335-3340.

Kojima et al., "Two-way cleavage of β-amyloid protein precursor by multicatalytic proteinase" Fed. Eur. Biochem. Soc. 304:57-60, Jun. 1992.

Koong et al. Hypoxia causes the activation of nuclear factor-κB through the phosphorylation of IκBα on tyrosine residues1, Cancer Research, 54:1425-1430, Mar. 15, 1994.

Koong et al. Hypoxic activation of nuclear factor-κB is mediated by a Ras and Raf signaling pathway and does not involve MAP kinase (ERK1 or ERK2)1, Cancer Research, 54:5273-5279, Oct. 15, 1994.

Kreidenweiss et al. "Comprehensive study of proteasome nhibitors against Plasmodium falciparum laboratory strains and field isolates from Gabon", Malar J., 7(187):1-8, 2008.

Krise et al. "A Novel Prodrug Approach for Tertiary Amines: Synthesis and Preliminary Evaluation of N-Phosphonooxymethyl Prodrugs", J. Med. Chem. 42:3094-3100, 1999.

Kuhn et al.: "Potent activity of carfilzomib, a novel, irreversible inhibitor of the ubiquitin-proteasome pathway, against preclinical models of multiple myeloma", BLOOD, 110(9): 3281-3290 prepublished online: Jun. 25, 2007.

Kumatori et al., "Abnormally high expression of proteasomes in human leukemic cells," Proc. Natl. Acad. Sci. USA, 1990, 87:7071-7075.

Lala et al., "Role of notric oxide in tymor progression: Lessons from experimental tumors," Cancer and Metastasis Reviews, 1998, 17:91-106.

Le Blanc et al., "Growth in Vivo and Prolongs Survival in a Murine Model Proteasome Inhibitor PS-341 Inhibits Human Myeloma Cell," Cancer Research, 2002, 62:4996-5000, Published online Sep. 1, 2002.

Lecker et al., "Multiple types of skeletal muscle atrophy involve a common program of changes in gene expression", FASEB J 18:39-51, 2004.

Liang et al., "Synthesis of Cryptophycin 52 Using the Sharpless Asymmetric Dihydroxylation: Diol to Epoxide Transformation Optimized for a Base-Sensitive Substrate," J. Am. Chem. Soc., 2000, 65:3143-3147.

Lin et al. "Alteration of substrate and inhibitor specificity of feline immunodeficiency virus protease", J. Virol., 74(10):4710-4720, 2000.

Loftsson et al., "Pharmaceutical Applications of Cyclodextrins. 1. Drug Solubilization and Stabalization," Journal of Pharmaceutical Sciences, American Pharmaceutical Association, 85(10):1017-1025 (1996).

MacAry et al., "Mobilization of MHC class I molecules from late endosomes to the cell surface following activation of CD34-derived human Langerhans cells", PNAS 98:3982-3987, 2001.

Mandel et al. "Neuroprotective Strategies in Parkinson's Disease", CNS Drugs, 2003: 17(10); 729-62.

Marx et al., "Reactivity-Selectivity in the Swern Oxidation of Alcohols Using Dimethyl Sulfoxide-Oxalyl Chloride," J. Org. Chem., 1984, 49:788-793.

McGraw-Hill Dictionary of Chemical Terms, 1990, p. 282.

Meng et al., "Eponemycin Exerts Its Antitumor Effect through the Inhibition of Proteasome Function," Cancer Research, 1999, 59:2798-2801.

Meng et al., "Epoxomicin, a potent and selective proteasome inhibitor, exhibits in vivo antiinflamatory activity," Proc. Natl. Acad. Sci. USA, 1999, 96:10403-10408.

Mishto et al., "Immunoproteasome and LMP2 polymorphism in aged and Alzheimer's disease brains", Neurobiol. Aging, 27:54-66, 2006.

Molecular biology and biotechnology a comprehensive desk reference: Edited by R A Meyers. pp. 658-664. VCH, Weinheim, Germany, 1995, DM89 ISBN 1-56081-925-1.

Molecular Probes, Inc. , "Introduction to Fluorescence techniques", invitrogen detection technologies, 11 pgs, Molecular Probes, Inc. (2007), Exhibit A to response filed with US Patent Office on Sep. 16, 2008 for U.S. Appl. No. 11/254,541 (now abandoned).

Morissette Sherry, et al. "high-thoughput crystallization: polymorphs, salts, co-crystals and solvates of pharmaceutical solids, advanced drug delivery reivews" Amsterdam, vol. 56, No. 3, 2004 p. 276.

Morris, "Structural Aspects of Hydrates and Solvates in Polymorphism in Pharmaceutical Solids", Polymorphism in Pharmaceutical Solids, Ed H. G. Nbrittain, Marcel Dekker, New York, pp. 125-181 (1999).

Myung et al., "Lack of Proteasome Active Site Allostery as Revealed by Subunit-Specific Inhibitors," Molecular Cell, 2001, 7(2):411-420.

Myung et al., "The Ubiquitin-Proteasome Pathway and Proteasome Inhibitors," Medicinal Research Reviews, 2001, 21(4):245-273.

Nemoto et al., "Catalytic Asymmetric Epoxidation of Enones Using La-BINOL-Triphenylarsine Oxide Complex: Structural Determination of the Asymmetric Catalyst," J. Am. Chem. Soc., 2001, 123:2725-2732.

Newman et al. "Solid-state analysis of the active pharmaceutical ingredient in drug products," Drug Discovery Today, 8(19):898-905, 2003.

Oishi et al., "Diastereoselective synthesis of new psi '(E)-CH=CMel- and psi '(Z)-CH=CMe1-type alkene dipeptide isosteres by organocopper reagents and application to conformationally restricted cyclic RGD peptidomimetics," J. Org. Chem., 2002, 67:6162-6173.

Orlowski and Kuhn, "Proteasome Inhibitors in Cancer Therapy: Lessons from the First Decade," Clin. Canc. Res., 2008, 14:1649-165.

Orlowski et al., "Phase I Trial of the Proteasome Inhibitor PS-341 in Patients With Refractory Hematologic Malignancies," Journal of Clinical Oncology, 2002, 20(22):4420-4427.

Overkleeft et al. "Solid phase synthesis of peptide vinyl sulfone and peptide expoxyketone proteasome inhibitors", Tetrahedron Letters, 41(32), 6005-6009, 2000.

Palombella et al., "The Ubiquitin-Proteasome Pathway Is Required for Processing the NF-.kappa.B1 Precursor Protein and the Activation of NF-.kappa.B," Cell, 1994, 78:773-785.

Paugam et al., "Characterization and role of protozoan parasite proteasomes," Trends Parasitol., 2003, 19:55-59.

Pivazyan et al., "Inhibition of HIC-1 Protease by a Boron-Modified Polypeptide", Biochem. Pharm. 60:927-936, Mar. 2000.

Pye et al. "Proteasome inhibition ablates activation of NF-κB in myocardial reperfusion and reduces reperfusion of injury", Am. J. Physiol. Heart Circ. Physiol 284:H919-H926, 2003.

Qureshi et al., "The Proteasome as a Lipopolysaccharide-Binding Protein in Macrophages: Differential Effects of Proteasome Inhibition on Lipopolysaccharide-Induced Signaling Events," J. Immunology, 2003, 171:1515-1525.

Raw et al. "Regulatory considerations of pharmaceutical solid polymorphism in Abbreviated New Drug Applications (ANDAs)," Advanced Drug Delivery Reviews 56:397-414, 2004.

Reidlinger et al. "Catalytic Properties of 26 S and 20 S Proteasomes and Radiolabling of MB 1, LMP7, and C7 Subunits Associated with Trypsin-like and Chymotrypsin-like Activities", J. of Biol Chem. 272(40), 24899-24905, May 27, 1997.

Roccaro et al., "Selective inhibition of chymotrypsin-like activity of the immunoproteasome and constitutive proteasome in Waldenström macroglobulimia," Blood, 2010, 115:4051-4060.

Rossi et al., "Proteasome inhibitors in cancer therapy: death by indigestion," Cell Death and Differentiation, 2005, as:1255-1257.

Safadi et al. "Phosphoryloxymet hyl Carbarnates and Carbonates-Novel Water-Soluble Prodrugs for Amines and Hindered Alcohols", Pharmaceutical Research 10(9), 1350-1355, Mar. 2, 1993.

Schwarz et al., 'The Selective Proteasome Inhibitors Lactacystin and Epoxomicin Can Be Used to Either Up- or Down-Regulate Antigen Presentation at Nontoxic Doses', The Journal of Immunology, 164: 6148-6157, 2000.

Shah et al. "Analytical Techniques for Quantification of Amorphous/Crystalline Phases in Pharmaceutical Solids," Journal of Pharm. Sciences, 95(8):1641-1665, 2006.

Shao et al., "A New Asymmetric Synthesis of .alpha.-Methylcysteines via Chiral Aziridines," J. Org. Chem., 1995, 60:790-791.

Sharpless et al., "High Stereo- and Regioselectivities in the Transition Metal Catalyzed Epoxidations of Olefinic Alcohols by tert-Butyl Hydroperoxide," J. Am. Chem. Soc., 1973, 95:6136-6137.

Shoemaker, "The NCI60 human tumour cell line anticancer drug screen",Cancer, Nature Reviews, 6:813-823, Oct. 2006.

Simsek et al. "Hepatitis B Virus Large and Middle Glycoproteins Are Degraded by a Proteasome Pathway in Glucosidase-Inhibited Cells but Not in Cells with Functional Glucosidase Enzyme", J. Virol. 79(20), 12914-12920, Oct. 2005.

Sin et al., "Eponymycin analogues: syntheses and use as probes of angiogenesis," Bioorganic & Medicinal Chemistry Letters, 6(8):1209-1217, Aug. 1998.

Sin et al., "Total synthesis of the potent proteasome inhibitor epoxomicin: a useful tool for understanding proteasome biology," Bioorganic & Medicinal Chemistry Letters, 1999, 9:2283-2288.

Singhal et al. "Drug polymorphism and dosage form design: a practical perspective" Advanced Drug Delivery Reviews, 56:335-347, 2004.

Spaltenstein et al., "Design and Synthesis of Novel Protease Inhibitors. Tripeptide .alpha.',.beta.'-Epoxyketones as Nanomolar Inactivators of the Proteasome," Tetrahedron Letters, 1996, 37:1343-1346.

Stein et al., "Kinetic Characterization of the Chymotryptic Activity of the 20S Proteasome," Biochemistry, 1996, 35:3899-3908.

Strickley, Robert G., "Solubilizing Excipients in Oral and Injectable Formulations," Pharmaceutical Research, 21(2):201-230 (2004).

Stoklosa et al. "Prospects for p53-based cancer therapy", Acta Biochim Pol., 52(2): 321-328, 2005.

Sun et al., inhimbition of acute graft-versus-host disease with retention of graft-versus-tumor effects by the proteasome inhibitor bortezomib: PNAS, 101(21):8120-8125, (2004).

Szalay et al. "Ongoing coxsackievirus myocarditis is associated with increased formation and activity of myocardial immunoproteaseomes", Am. J. Pathol. 168(5), 1542-1552, May 2006.

Tawa et al., "Inhibitors of the Proteasome Reduce the Accelerated Proteolysis in Atrophying Rat Skeletal Muscles", JCI 100:197-203, 1997.

Terato et al. "Induction of arthritis with monoclonal antibodies to collagen1" J. Immunol, 148(7), 2103-2108, Apr. 1, 1992.

Thanos et al., "NF-.kappa.B: A Lesson in Family Values," Cell, 1995, 80:529-532.

Thompson Do., J. Pharm.Sc., 85:1017-1025, 1996 (cite at Loftsson).

Thompson., "Cyclodextrins-enabling excipients: their present and future use in pharmaceuticals," Critical Reviews in Therapeutic Drug Carrier Systems, 14(1):1-104 (1997).

Tong, Wei-Qin (Tony), "Applications of Complexation in the Formulation of Insoluble Compounds," R. Liu, Ed., pp. 111-139 (2000).

Traenckner et al., "A proteasome inhibitor prevents activation of NF-.kappa.B and stabilizes a newly phosphorylated form of I.kappa.B-.alpha. that is still bound to NF-.kappa.B," EMBO J., 1994, 13:5433-5441.

Tu et al., "An Efficient Assymettric Epoxidation Method for trans-Olefins Mediated by a Fructose-Derived Ketone," J. Am. Chem. Soc., 1996, 118:9806-9807.

Vogel's textbook of practical organic chemistry, 5th Ed. See p. 135, "2.20 Recrystallisation Techniques" and p. 141, 2nd paragraph onwards, 1989.

Voskoglou-Nomikos, "Clinical Predictive Value of the in Vitro Cell Line, Human Xenograft, and Mouse Allograft Preclinical Cancer Models," Clin Cancer Res., 2003, 9(11):4227-4239.

Wang et al., "A New Type of Ketone Catalyst for Asymmetric Epoxidation," J. Org. Chem., 1997, 62:8622-8623.

Watanabe et al. "Synthesis of boronic acid derivatives of tyropeptin: Proteasome inhibitors", Bioorg. & Med. Chem., 19(8):2343-2345, Apr. 2009.

WebMD "HIV and Aids", www.webmd.com/hiv-aids/guide/sexual-health-aids pp. 1-2, 2009, updated.

Wilson et al., "Novel disease targets and management approaches for diffuse large B-cell lymphoma", Leukemia & Lymphoma, 51 suppl. 1:1-10 abstract only, 2010.

Wipf et al., "Methyl- and (Trifluoromethyl)alkene Peptide Isosteres: Synthesis and Evaluation of Their Potential as .beta.-Turn Promoters and Peptide Mimetics," J. Org. Chem., 1998, 63:6088-6089.

Xu et al. "Mutations in the tumor suppressors Smad2 and Smad4 inactivate transforming growth factor βsignaling by targeting Smads to the ubiquitin-proteasome pathway", PNAS 97(9), 4820-4825, Apr. 25, 2000.

Yu et al. "The Ubiquitin-Proteasome System Facilitates the Transfer of Murine Coronavirus from Endosome to Cytoplasm during Virus Entry", J. Virol. 79(1), 644-648, Jan. 2005.

Zhou et al., "Design and Synthesis of an Orally Bioavailable and Selectrive Peptide Epoxyketone Proteasome Inhibitor (PR-047)," J. Med. Chem., 2009, 52 (9):3028-3038.

Zhu et al., "3D-QSAR studies of boron-containing dipeptides as proteasome inhibitors with CoMFA and CoMSIA methods", Eur Journ. Med. Chem., 44(4):1486-1499, Apr. 2009.

Zhu et al., "Design, Synthesis and biological evaluation of tripeptide boronic acid proteasome inhibitors", Bioorg & Med. Chem., 17(19):6851-6861, Oct. 2009.

Zollner et al. "Proteasome inhibition reduces superantigen-mediated T cell activation and the severity of psoriasis in a SCID-hu model", J. Clin. Invest., 109(5): 671-679, 2002.

* cited by examiner

| | | immunoproteasome expression level | | | | | |
|---|---|---|---|---|---|---|---|
| | | cell lines | | | patient samples | | |
| | | high | mixed | low | high | mixed | low |
| Multiple myeloma | | 3/4 | 1/4 | | 1/3 | 2/3 | |
| Leukemias | PML | 1/1 | | | | | |
| | AML | 4/6 | 2/6 | | 12/15 | 3/15 | |
| | CML | | | 2/2 | | | |
| | ALL | 1/1 | | | 6/6 | | |
| | APL | 1/1 | | | | | |
| | CLL | | | | 6/6 | | |
| Lymphomas | T cell | 6/6 | | | | | |
| | B cell | 3/7 | 4/7 | | | | |
| Solid tumors | | | | 4/4 | | | |

| high | mixed | low |
|---|---|---|
| >70% immunoproteasome | 30-70% immunoproteasome | <30% immunoproteasome |

Figure 1

COMPOUNDS FOR ENZYME INHIBITION

RELATED APPLICATIONS

This application is a continuation of U.S. patent application Ser. No. 12/708,753, filed Feb. 19, 2010, issued as U.S. Pat. No. 8,080,545 on Dec. 20, 2011, which is a continuation of U.S. patent application Ser. No. 11/820,490, filed Jun. 19, 2007, issued as U.S. Pat. No. 7,691,852, which claims the benefit of U.S. Provisional Application No. 60/815,218, filed Jun. 19, 2006. This application is related to U.S. patent application Ser. No. 12/708,932, filed Feb. 19, 2010, issued as U.S. Pat. No. 8,080,576. The contents of this application are incorporated herein by reference in its entirety.

BACKGROUND OF THE INVENTION

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, a multicatalytic protease, which cleaves proteins into short peptides through the action of its three major proteolytic activities. While having a general function in intracellular protein turnover, proteasome-mediated degradation also plays a key role in many processes such as major histocompatibility complex (MHC) class I presentation, apoptosis and cell viability, antigen processing, NF-κB activation, and transduction of pro-inflammatory signals.

The 20S proteasome is a 700 kDa cylindrical-shaped multicatalytic protease complex comprised of 28 subunits, classified as α- and β-type, that are arranged in 4 stacked heptameric rings. In yeast and other eukaryotes, 7 different α subunits form the outer rings and 7 different β subunits comprise the inner rings. The α subunits serve as binding sites for the 19S (PA700) and 11S (PA28) regulatory complexes, as well as a physical barrier for the inner proteolytic chamber formed by the two β subunit rings. Thus, in vivo, the proteasome is believed to exist as a 26S particle ("the 26S proteasome"). In vivo experiments have shown that inhibition of the 20S form of the proteasome can be readily correlated to inhibition of 26S proteasome.

Cleavage of amino-terminal prosequences of β subunits during particle formation expose amino-terminal threonine residues, which serve as the catalytic nucleophiles. The subunits responsible for catalytic activity in proteasome thus possess an amino terminal nucleophilic residue, and these subunits belong to the family of N-terminal nucleophile (Ntn) hydrolases (where the nucleophilic N-terminal residue is, for example, Cys, Ser, Thr, and other nucleophilic moieties). This family includes, for example, penicillin G acylase (PGA), penicillin V acylase (PVA), glutamine PRPP amidotransferase (GAT), and bacterial glycosylasparaginase. In addition to the ubiquitously expressed β subunits, higher vertebrates also possess three interferon-γ-inducible β subunits (LMP7, LMP2 and MECL1), which replace their normal counterparts, β5, β1 and β2, respectively. When all three IFN-γ-inducible subunits are present, the proteasome is referred to as an "immunoproteasome". Thus, eukaryotic cells can possess two forms of proteasomes in varying ratios.

Through the use of different peptide substrates, three major proteolytic activities have been defined for the eukaryote 20S proteasomes: chymotrypsin-like activity (CT-L), which cleaves after large hydrophobic residues; trypsin-like activity (T-L), which cleaves after basic residues; and peptidyl-glutamyl peptide hydrolyzing activity (PGPH), which cleaves after acidic residues. Two additional less characterized activities have also been ascribed to the proteasome: BrAAP activity, which cleaves after branched-chain amino acids; and SNAAP activity, which cleaves after small neutral amino acids. Although both forms of the proteasome possess all five enzymatic activities, differences in the extent of the activities between the forms have been described based on specific substrates. For both forms of the proteasome, the major proteasome proteolytic activities appear to be contributed by different catalytic sites within the 20S core.

There are several examples of small molecules which have been used to inhibit proteasome activity; however, these compounds generally lack the specificity to delineate between the two forms of the proteasome. Thus, the ability to explore and exploit the roles of each specific proteasome form at the cellular and molecular level has not been possible. Therefore, the creation of small molecule inhibitor(s) that preferentially inhibit a single form of the proteasome is needed to allow the exploration of the roles of each proteasome form at the cellular and molecular level.

SUMMARY OF THE INVENTION

One aspect of the invention relates to inhibitors that preferentially inhibit immunoproteasome activity over constitutive proteasome activity. In certain embodiments, the invention relates to the treatment of immune related diseases, comprising administering a compound of the invention. In certain embodiments, the invention relates to the treatment of cancer, comprising administering a compound of the invention.

One aspect of the invention relates to compounds having a structure of formula (I) or a pharmaceutically acceptable salt thereof,

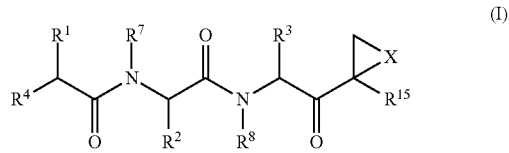

wherein
each Ar is independently an aromatic or heteroaromatic group optionally substituted with 1 to 4 substituents;
each A is independently selected from C=O, C=S, and SO$_2$, preferably C=O; or
A is optionally a covalent bond when adjacent to an occurrence of Z;
B is absent or is N(R$^9$)R$^{10}$, preferably absent;
L is absent or is selected from C=O, C=S, and SO$_2$, preferably SO$_2$ or C=O;
M is absent or is C$_{1-12}$alkyl, preferably C$_{1-8}$alkyl;
Q is absent or is selected from O, NH, and N—C$_{1-6}$alkyl;
X is selected from O, S, NH, and N—C$_{1-6}$alkyl, preferably O;
Y is absent or is selected from C=O and SO$_2$;
each Z is independently selected from O, S, NH, and N—C$_{1-6}$alkyl, preferably O; or
Z is optionally a covalent bond when adjacent to an occurrence of A;
R$^1$ is selected from H, —C$_{1-6}$alkyl-B, C$_{1-6}$hydroxyalkyl, C$_{1-6}$alkoxyalkyl, aryl, and C$_{1-6}$aralkyl;
R$^2$ and R$^3$ are each independently selected from aryl, C$_{1-6}$aralkyl, heteroaryl, and C$_{1-6}$heteroaralkyl;
R$^4$ is N(R$^5$)L-Q-R$^6$;

$R^5$ is selected from hydrogen, OH, $C_{1-6}$aralkyl, and $C_{1-6}$alkyl, preferably hydrogen;

$R^6$ is selected from hydrogen, $C_{1-6}$alkyl, $C_{1-6}$alkenyl, $C_{1-6}$alkynyl, Ar—Y—, carbocyclyl, heterocyclyl, an N-terminal protecting group, aryl, $C_{1-6}$aralkyl, heteroaryl, $C_{1-6}$heteroaralkyl, $R^{11}ZAZ$—$C_{1-8}$alkyl-, $R^{14}Z$—$C_{1-8}$alkyl-, $(R^{11}O)(R^{12}O)P(=O)O$—$C_{1-8}$alkyl-ZAZ—$C_{1-8}$alkyl-, $R^{11}ZAZ$—$C_{1-8}$alkyl-ZAZ—$C_{1-8}$alkyl-, heterocyclylMZAZ—$C_{1-8}$alkyl-, $(R^{11}O)(R^{12}O)P(=O)O$—$C_{1-8}$alkyl-, $(R^{13})_2N$—$C_{1-12}$alkyl-, $(R^{13})_3N^+$—$C_{1-12}$alkyl-, heterocyclylM-, carbocyclylM-, $R^{14}SO_2C_{1-8}$alkyl-, and $R^{14}SO_2NH$; preferably an N-capping group; or $R^5$ and $R^6$ together are $C_{1-6}$alkyl-Y—$C_{1-6}$alkyl, $C_{1-6}$alkyl-ZAZ—$C_{1-6}$alkyl, ZAZ—$C_{1-6}$alkyl-ZAZ—$C_{1-6}$alkyl, ZAZ—$C_{1-6}$alkyl-ZAZ, or $C_{1-6}$alkyl-A, thereby forming a ring;

$R^7$ and $R^8$ are independently selected from hydrogen, $C_{1-6}$alkyl, and $C_{1-6}$aralkyl, preferably hydrogen;

$R^9$ is selected from hydrogen, OH, and $C_{1-6}$alkyl, preferably $C_{1-6}$alkyl; and $R^{10}$ is an N-terminal protecting group;

$R^{11}$ and $R^{12}$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^{11}$ and $R^{12}$ together are $C_{1-6}$alkyl, thereby forming a ring;

each $R^{13}$ is independently selected from hydrogen and $C_{1-6}$alkyl, preferably $C_{1-6}$alkyl; and $R^{14}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

$R^{15}$ is selected from hydrogen, $C_{1-6}$alkyl, $C_{1-6}$hydroxyalkyl, $C_{1-6}$alkoxy, —C(O)O$C_{1-6}$alkyl, —C(O)NH$C_{1-6}$alkyl, and $C_{1-6}$aralkyl;

provided that in any occurrence of the sequence ZAZ, at least one member of the sequence must be other than a covalent bond.

Another aspect of the invention relates to compounds having a structure of formula (II) or a pharmaceutically acceptable salt thereof,

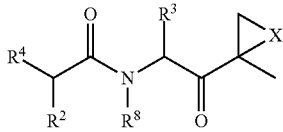

(II)

each Ar is independently an aromatic or heteroaromatic group optionally substituted with 1 to 4 substituents;

each A is independently selected from C=O, C=S, and $SO_2$, preferably C=O; or

A is optionally a covalent bond when adjacent to an occurrence of Z;

B is absent or is $N(R^9)R^{10}$, preferably absent;

L is absent or is selected from C=O, C=S, and $SO_2$, preferably $SO_2$ or C=O;

M is absent or is $C_{1-12}$alkyl, preferably $C_{1-8}$alkyl;

Q is absent or is selected from O, NH, and N—$C_{1-6}$alkyl;

X is selected from O, S, NH, and N—$C_{1-6}$alkyl, preferably O;

Y is absent or is selected from C=O and $SO_2$;

each Z is independently selected from O, S, NH, and N—$C_{1-6}$alkyl, preferably O; or Z is optionally a covalent bond when adjacent to an occurrence of A;

$R^2$ and $R^3$ are each independently selected from aryl, $C_{1-6}$aralkyl, heteroaryl, and $C_{1-6}$heteroaralkyl;

$R^4$ is $N(R^5)L$-Q-$R^6$;

$R^5$ is selected from hydrogen, OH, $C_{1-6}$aralkyl, and $C_{1-6}$alkyl, preferably hydrogen;

$R^6$ is selected from hydrogen, $C_{1-6}$alkyl, $C_{1-6}$alkenyl, $C_{1-6}$alkynyl, Ar—Y—, carbocyclyl, heterocyclyl, an N-terminal protecting group, aryl, $C_{1-6}$aralkyl, heteroaryl, $C_{1-6}$heteroaralkyl, $R^{11}ZAZ$—$C_{1-8}$alkyl-, $R^{14}Z$—$C_{1-8}$alkyl-, $(R^{11}O)(R^{12}O)P(=O)O$—$C_{1-8}$alkyl-ZAZ—$C_{1-8}$alkyl-, $R^{11}ZAZ$—$C_{1-8}$alkyl-ZAZ—$C_{1-8}$alkyl-, heterocyclylMZAZ—$C_{1-8}$alkyl-, $(R^{11}O)(R^{12}O)P(=O)O$—$C_{1-8}$alkyl-, $(R^{13})_2N$—$C_{1-12}$alkyl-, $(R^{13})_3N^+$—$C_{1-12}$alkyl-, heterocyclylM-, carbocyclylM-, $R^{14}SO_2C_{1-8}$alkyl-, and $R^{14}SO_2NH$; preferably an N-capping group; or $R^5$ and $R^6$ together are $C_{1-6}$alkyl-Y—$C_{1-6}$alkyl, $C_{1-6}$alkyl-ZAZ—$C_{1-6}$alkyl, ZAZ—$C_{1-6}$alkyl-ZAZ—$C_{1-6}$alkyl, ZAZ—$C_{1-6}$alkyl-ZAZ, or $C_{1-6}$alkyl-A, thereby forming a ring;

$R^8$ is selected from hydrogen, $C_{1-6}$alkyl, and $C_{1-6}$aralkyl, preferably hydrogen;

$R^9$ is selected from hydrogen, OH, and $C_{1-6}$alkyl, preferably $C_{1-6}$alkyl; and $R^{10}$ is an N-terminal protecting group;

$R^{11}$ and $R^{12}$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^{11}$ and $R^{12}$ together are $C_{1-6}$alkyl, thereby forming a ring;

each $R^{13}$ is independently selected from hydrogen and $C_{1-6}$alkyl, preferably $C_{1-6}$alkyl; and $R^{14}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

$R^{15}$ is selected from hydrogen, $C_{1-6}$alkyl, $C_{1-6}$hydroxyalkyl, $C_{1-6}$alkoxy, —C(O)O$C_{1-6}$alkyl, —C(O)NH$C_{1-6}$alkyl, and $C_{1-6}$aralkyl;

provided that in any occurrence of the sequence ZAZ, at least one member of the sequence must be other than a covalent bond.

Another aspect of the invention relates to compounds having a structure of formula (III) or a pharmaceutically acceptable salt thereof,

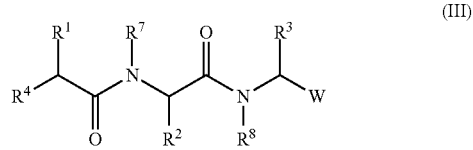

(III)

wherein each A is independently selected from C=O, C=S, and $SO_2$, preferably C=O; or A is optionally a covalent bond when adjacent to an occurrence of Z;

B is absent or is $N(R^9)R^{10}$, preferably absent;

L is absent or is selected from C=O, C=S, and $SO_2$, preferably $SO_2$ or C=O;

M is absent or is $C_{1-12}$alkyl, preferably $C_{1-8}$alkyl;

W is selected from —CHO and —B(O$R^{11}$)$_2$;

Q is absent or is selected from O, NH, and N—$C_{1-6}$alkyl;

Y is absent or is selected from C=O and $SO_2$;

each Z is independently selected from O, S, NH, and N—$C_{1-6}$alkyl, preferably O; or Z is optionally a covalent bond when adjacent to an occurrence of A;

R$^1$ is selected from H, —C$_{1-6}$alkyl-B, C$_{1-6}$hydroxyalkyl, C$_{1-6}$alkoxyalkyl, aryl, and C$_{1-6}$aralkyl;

R$^2$ and R$^3$ are each independently selected from aryl, C$_{1-6}$aralkyl, heteroaryl, and C$_{1-6}$heteroaralkyl;

R$^4$ is N(R$^5$)L-Q-R$^6$;

R$^5$ is selected from hydrogen, OH, C$_{1-6}$aralkyl, and C$_{1-6}$alkyl, preferably hydrogen;

R$^6$ is selected from hydrogen, C$_{1-6}$alkyl, C$_{1-6}$alkenyl, C$_{1-6}$alkynyl, Ar—Y—, carbocyclyl, heterocyclyl, an N-terminal protecting group, aryl, C$_{1-6}$aralkyl, heteroaryl, C$_{1-6}$heteroaralkyl, R$^{11}$ZAZ—C$_{1-8}$alkyl-, R$^{14}$Z—C$_{1-8}$alkyl-, (R$^{11}$O)(R$^{12}$O)P(=O)O—C$_{1-8}$alkyl-ZAZ—C$_{1-8}$alkyl-, R$^{11}$ZAZ—C$_{1-8}$alkyl-ZAZ—C$_{1-8}$alkyl-, heterocyclylMZAZ—C$_{1-8}$alkyl-, (R$^{11}$O)(R$^{12}$O)P(=O)O—C$_{1-8}$alkyl-, (R$^{13}$)$_2$N—C$_{1-12}$alkyl-, (R$^{13}$)$_3$N$^+$—C$_{1-12}$alkyl-, heterocyclylM-, carbocyclylM-, R$^{14}$SO$_2$C$_{1-8}$alkyl-, and R$^{14}$SO$_2$NH; preferably an N-capping group; or R$^5$ and R$^6$ together are C$_{1-6}$alkyl-Y—C$_{1-6}$alkyl, C$_{1-6}$alkyl-ZAZ—C$_{1-6}$alkyl, ZAZ—C$_{1-6}$alkyl-ZAZ—C$_{1-6}$alkyl, ZAZ—C$_{1-6}$alkyl-ZAZ, or C$_{1-6}$alkyl-A, thereby forming a ring;

R$^7$ and R$^8$ are independently selected from hydrogen, C$_{1-6}$alkyl, and C$_{1-6}$aralkyl, preferably hydrogen;

R$^9$ is selected from hydrogen, OH, and C$_{1-6}$alkyl, preferably C$_{1-6}$alkyl; and R$^{10}$ is an N-terminal protecting group;

R$^{11}$ and R$^{12}$ are independently selected from hydrogen, metal cation, C$_{1-6}$alkyl, C$_{1-6}$alkenyl, C$_{1-6}$alkynyl, aryl, heteroaryl, C$_{1-6}$aralkyl, and C$_{1-6}$heteroaralkyl, preferably from hydrogen, metal cation, and C$_{1-6}$alkyl, or R$^{11}$ and R$^{12}$ together are C$_{1-6}$alkyl, thereby forming a ring;

each R$^{13}$ is independently selected from hydrogen and C$_{1-6}$alkyl, preferably C$_{1-6}$alkyl; and R$^{14}$ is independently selected from hydrogen, C$_{1-6}$alkyl, C$_{1-6}$alkenyl, C$_{1-6}$alkynyl, carbocyclyl, heterocyclyl, aryl, heteroaryl, C$_{1-6}$aralkyl, and C$_{1-6}$heteroaralkyl;

each R$^{16}$ is independently selected from hydrogen and C$_{1-6}$alkyl; or two occurrences of R$^{11}$ together may be C$_{1-6}$alkyl, thereby forming a ring together with the intervening boron and oxygen atoms to which they are attached;

provided that in any occurrence of the sequence ZAZ, at least one member of the sequence must be other than a covalent bond.

Another aspect of the invention relates to compounds having a structure of formula (IV) or a pharmaceutically acceptable salt thereof,

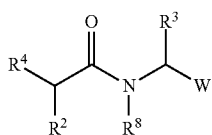

(IV)

wherein each A is independently selected from C=O, C=S, and SO$_2$, preferably C=O; or A is optionally a covalent bond when adjacent to an occurrence of Z;

L is absent or is selected from C=O, C=S, and SO$_2$, preferably SO$_2$ or C=O;

M is absent or is C$_{1-12}$alkyl, preferably C$_{1-8}$alkyl;

W is selected from —CHO and —B(OR$^{11}$)$_2$;

Q is absent or is selected from O, NH, and N—C$_{1-6}$alkyl;

Y is absent or is selected from C=O and SO$_2$;

each Z is independently selected from O, S, NH, and N—C$_{1-6}$alkyl, preferably O; or Z is optionally a covalent bond when adjacent to an occurrence of A;

R$^2$ and R$^3$ are each independently selected from aryl, C$_{1-6}$aralkyl, heteroaryl, and C$_{1-6}$heteroaralkyl;

R$^4$ is N(R$^5$)L-Q-R$^6$;

R$^5$ is selected from hydrogen, OH, C$_{1-6}$aralkyl, and C$_{1-6}$alkyl, preferably hydrogen;

R$^6$ is selected from hydrogen, C$_{1-6}$alkyl, C$_{1-6}$alkenyl, C$_{1-6}$alkynyl, Ar—Y—, carbocyclyl, heterocyclyl, an N-terminal protecting group, aryl, C$_{1-6}$aralkyl, heteroaryl, C$_{1-6}$heteroaralkyl, R$^{11}$ZAZ—C$_{1-8}$alkyl-, R$^{14}$Z—C$_{1-8}$alkyl-, (R$^{11}$O)(R$^{12}$O)P(=O)O—C$_{1-8}$alkyl-ZAZ—C$_{1-8}$alkyl-, R$^{11}$ZAZ—C$_{1-8}$alkyl-ZAZ—C$_{1-8}$alkyl-, heterocyclylMZAZ—C$_{1-8}$alkyl-, (R$^{11}$O)(R$^{12}$O)P(=O)O—C$_{1-8}$alkyl-, (R$^{13}$)$_2$N—C$_{1-12}$alkyl-, (R$^{13}$)$_3$N$^+$—C$_{1-12}$alkyl-, heterocyclylM-, carbocyclylM-, R$^{14}$SO$_2$C$_{1-8}$alkyl-, and R$^{14}$SO$_2$NH; preferably an N-capping group; or R$^5$ and R$^6$ together are C$_{1-6}$alkyl-Y—C$_{1-6}$alkyl, C$_{1-6}$alkyl-ZAZ—C$_{1-6}$alkyl, ZAZ—C$_{1-6}$alkyl-ZAZ—C$_{1-16}$alkyl, ZAZ—C$_{1-6}$alkyl-ZAZ, or C$_{1-6}$alkyl-A, thereby forming a ring;

R$^8$ is selected from hydrogen, C$_{1-6}$alkyl, and C$_{1-6}$aralkyl, preferably hydrogen;

R$^9$ is selected from hydrogen, OH, and C$_{1-6}$alkyl, preferably C$_{1-6}$alkyl; and R$^{10}$ is an N-terminal protecting group;

R$^{11}$ and R$^{12}$ are independently selected from hydrogen, metal cation, C$_{1-6}$alkyl, C$_{1-6}$alkenyl, C$_{1-6}$alkynyl, aryl, heteroaryl, C$_{1-6}$aralkyl, and C$_{1-6}$heteroaralkyl, preferably from hydrogen, metal cation, and C$_{1-6}$alkyl, or R$^{11}$ and R$^{12}$ together are C$_{1-6}$alkyl, thereby forming a ring;

each R$^{13}$ is independently selected from hydrogen and C$_{1-6}$alkyl, preferably C$_{1-6}$alkyl; and R$^{14}$ is independently selected from hydrogen, C$_{1-6}$alkyl, C$_{1-6}$alkenyl, C$_{1-6}$alkynyl, carbocyclyl, heterocyclyl, aryl, heteroaryl, C$_{1-6}$aralkyl, and C$_{1-6}$heteroaralkyl;

each R$^{16}$ is independently selected from hydrogen and C$_{1-6}$alkyl; or two occurrences of R$^{11}$ together may be C$_{1-6}$alkyl, thereby forming a ring together with the intervening boron and oxygen atoms to which they are attached;

provided that in any occurrence of the sequence ZAZ, at least one member of the sequence must be other than a covalent bond.

BRIEF DESCRIPTION OF THE FIGURES

FIG. 1 shows the immunoproteasome expression level of certain cell lines and patient samples, including multiple myeloma, leukemias, lymphomas, and solid tumors.

DETAILED DESCRIPTION OF THE INVENTION

Figure 2:
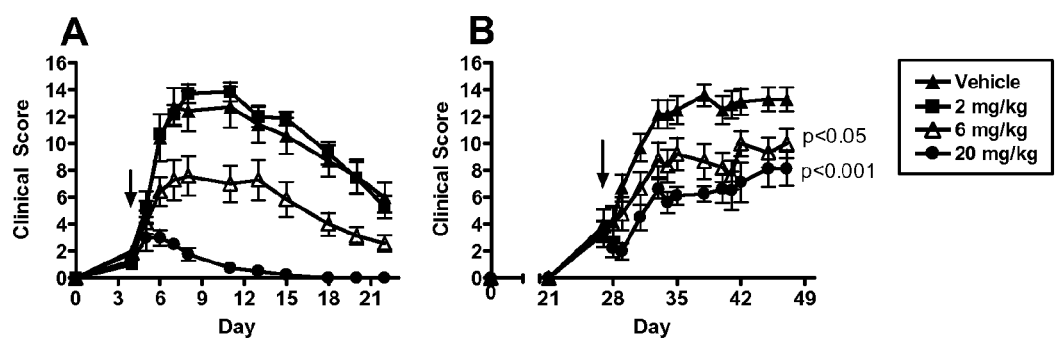
FIG. 2A shows the effect of Compound 14 on disease progression in mouse models of rheumatoid arthritis (RA) where dosing began when animals first showed signs of disease (indicated by arrows) and data shown is average disease score (±SEM; N=7/group) and is representative of three independent experiments.
FIG. 2B shows the effect of Compound 14 on disease progression in mouse models of RA where RA was induced on Day 0 in female DBA/1 mice by immunization with bovine type II collagen in CFA where dosing began when animals first showed signs of disease (indicated by arrows) and data shown is average disease score (±SEM; N=10/group).

The invention involves compounds useful as enzyme inhibitors. These compounds are generally useful to inhibit enzymes having a nucleophilic group at the N-terminus. For example, activities of enzymes or enzyme subunits having N-terminal amino acids with nucleophiles in their side chains, such as threonine, serine, or cysteine can be successfully inhibited by the enzyme inhibitors described herein. Activities of enzymes or enzyme subunits having non-amino acid nucleophilic groups at their N-termini, such as, for example, protecting groups or carbohydrates, can also be successfully inhibited by the enzyme inhibitors described herein.

While not bound by any particular theory of operation, it is believed that such N-terminal nucleophiles of Ntn form covalent adducts with the epoxide, aziridine, aldehyde, or borate functional group of the enzyme inhibitors described herein. For example, in the β5/Pre2 subunit of 20S proteasome, the N-terminal threonine is believed to irreversibly form a morpholino or piperazino adduct upon reaction with a peptide epoxide or aziridine such as those described below. Such adduct formation would involve ring-opening cleavage of the epoxide or aziridine.

Regarding the stereochemistry, the Cahn-Ingold-Prelog rules for determining absolute stereochemistry are followed. These rules are described, for example, in Organic Chemistry, Fox and Whitesell; Jones and Bartlett Publishers, Boston, Mass. (1994); Section 5-6, pp 177-178, which section is hereby incorporated by reference. Peptides can have a repeating backbone structure with side chains extending from the backbone units. Generally, each backbone unit has a side chain associated with it, although in some cases, the side chain is a hydrogen atom. In other embodiments, not every backbone unit has an associated side chain. Peptides useful in peptide epoxides or peptide aziridines have two or more backbone units. In some embodiments useful for inhibiting chymotrypsin-like (CT-L) activity of the proteasome, between two and eight backbone units are present, and in some preferred embodiments for CT-L inhibition, between two and six backbone units are present.

The side chains extending from the backbone units can include natural aliphatic or aromatic amino acid side chains, such as hydrogen (glycine), methyl (alanine), isopropyl (valine), sec-butyl (isoleucine), isobutyl (leucine), phenylmethyl (phenylalanine), and the side chain constituting the amino acid proline. The side chains can also be other branched or unbranched aliphatic or aromatic groups such as ethyl, n-propyl, n-butyl, t-butyl, and aryl substituted derivatives such as 1-phenylethyl, 2-phenylethyl, (1-naphthyl)methyl, (2-naphthyl)methyl, 1-(1-naphthyl)ethyl, 1-(2-naphthyl)ethyl, 2-(1-naphthyl)ethyl, 2-(2-naphthyl)ethyl, and similar compounds. The aryl groups can be further substituted with branched or unbranched C1-6alkyl groups, or substituted alkyl groups, acetyl and the like, or further aryl groups, or substituted aryl groups, such as benzoyl and the like. Heteroaryl groups can also be used as side chain substituents. Heteroaryl groups include nitrogen-, oxygen-, and sulfur-containing aryl groups such as thienyl, benzothienyl, naphthothienyl, thianthrenyl, furyl, pyranyl, isobenzofuranyl, chromenyl, pyrrolyl, imidazolyl, pyrazolyl, pyridyl, pyrazinyl, indolyl, purinyl, quinolyl, and the like.

In some embodiments, polar or charged residues can be introduced into the peptide epoxides or peptide aziridines. For example, naturally occurring amino acids such as hydroxy-containing (Thr, Tyr, Ser) or sulfur-containing (Met, Cys) can be introduced, as well as non-essential amino acids, for example, taurine, carnitine, citrulline, cystine, ornithine, norleucine and others. Non-naturally occurring side chain substituents with charged or polar moieties can also be included, such as, for example, C1-6alkyl chains or C6-12aryl groups with one or more hydroxy, short chain alkoxy, sulfide, thio, carboxyl, ester, phospho, amido or amino groups, or such substituents substituted with one or more halogen atoms. In some preferred embodiments, there is at least one aryl group present in a side chain of the peptide moiety.

In some embodiments, the backbone units are amide units [—NH—CHR—C(=O)—], in which R is the side chain. Such a designation does not exclude the naturally occurring amino acid proline, or other non-naturally occurring cyclic secondary amino acids, which will be recognized by those of skill in the art.

In other embodiments, the backbone units are N-alkylated amide units (for example, N-methyl and the like), olefinic analogs (in which one or more amide bonds are replaced by olefinic bonds), tetrazole analogs (in which a tetrazole ring imposes a cis-configuration on the backbone), or combinations of such backbone linkages. In still other embodiments, the amino acid α-carbon is modified by α-alkyl substitution, for example, aminoisobutyric acid. In some further embodiments, side chains are locally modified, for example, by ΔE or ΔZ dehydro modification, in which a double bond is present between the α and β atoms of the side chain, or for example by ΔE or ΔZ cyclopropyl modification, in which a cyclopropyl group is present between the α and β atoms of the side chain. In still further embodiments employing amino acid groups, D-amino acids can be used. Further embodiments can include side chain-to-backbone cyclization, disulfide bond formation, lactam formation, azo linkage, and other modifications discussed in "Peptides and Mimics, Design of Conformationally Constrained" by Hruby and Boteju, in "Molecular Biology and Biotechnology: A Comprehensive Desk Reference", ed. Robert A. Meyers, VCH Publishers (1995), pp. 658-664, which is hereby incorporated by reference.

One aspect of the invention relates to compounds having a structure of formula (I) or a pharmaceutically acceptable salt thereof,

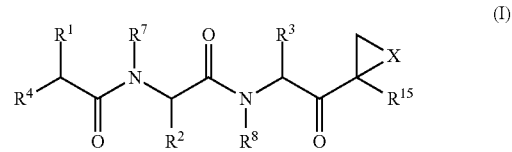

(I)

wherein each Ar is independently an aromatic or heteroaromatic group optionally substituted with 1 to 4 substituents;

each A is independently selected from C=O, C=S, and SO$_2$, preferably C=O; or

A is optionally a covalent bond when adjacent to an occurrence of Z;

B is absent or is N(R$^9$)R$^{10}$, preferably absent;

L is absent or is selected from C=O, C=S, and SO$_2$, preferably SO$_2$ or C=O;

M is absent or is C$_{1-12}$alkyl, preferably C$_{1-8}$alkyl;

Q is absent or is selected from O, NH, and N—C$_{1-6}$alkyl;

X is selected from O, S, NH, and N—C$_{1-6}$alkyl, preferably O;

Y is absent or is selected from C=O and SO$_2$;

each Z is independently selected from O, S, NH, and N—C$_{1-6}$alkyl, preferably O; or Z is optionally a covalent bond when adjacent to an occurrence of A;

R¹ is selected from H, —$C_{1-6}$alkyl-B, $C_{1-6}$hydroxyalkyl, $C_{1-6}$alkoxyalkyl, aryl, and $C_{1-6}$aralkyl;

R² and R³ are each independently selected from aryl, $C_{1-6}$aralkyl, heteroaryl, and $C_{1-6}$heteroaralkyl;

R⁴ is N(R⁵)L-Q-R⁶;

R⁵ is selected from hydrogen, OH, $C_{1-6}$aralkyl, and $C_{1-6}$alkyl, preferably hydrogen;

R⁶ is selected from hydrogen, $C_{1-6}$alkyl, $C_{1-6}$alkenyl, $C_{1-6}$alkynyl, Ar—Y—, carbocyclyl, heterocyclyl, an N-terminal protecting group, aryl, $C_{1-6}$aralkyl, heteroaryl, $C_{1-6}$heteroaralkyl, R¹¹ZAZ—$C_{1-8}$alkyl-, R¹⁴Z—$C_{1-8}$alkyl-, (R¹¹O)(R¹²O)P(=O)O—$C_{1-8}$alkyl-ZAZ—$C_{1-8}$alkyl-, R¹¹ZAZ—$C_{1-8}$alkyl-ZAZ—$C_{1-8}$alkyl-, heterocyclylMZAZ—$C_{1-8}$alkyl-, (R¹¹O)(R¹²O)P(=O)O—$C_{1-8}$alkyl-, (R¹³)₂N—$C_{1-12}$alkyl-, (R¹³)₃N⁺—$C_{1-12}$alkyl-, heterocyclylM-, carbocyclylM-, R¹⁴SO₂$C_{1-8}$alkyl-, and R¹⁴SO₂NH; preferably an N-capping group, more preferably t-butoxycarbonyl or benzyloxycarbonyl; or R⁵ and R⁶ together are $C_{1-6}$alkyl-Y—$C_{1-6}$alkyl, $C_{1-6}$alkyl-ZAZ—$C_{1-6}$alkyl, ZAZ—$C_{1-6}$alkyl-ZAZ—$C_{1-6}$alkyl, ZAZ—$C_{1-6}$alkyl-ZAZ, or $C_{1-6}$alkyl-A, thereby forming a ring;

R⁷ and R⁸ are independently selected from hydrogen, $C_{1-6}$alkyl, and $C_{1-6}$aralkyl, preferably hydrogen;

R⁹ is selected from hydrogen, OH, and $C_{1-6}$alkyl, preferably $C_{1-6}$alkyl; and R¹⁰ is an N-terminal protecting group;

R¹¹ and R¹² are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or R¹¹ and R¹² together are $C_{1-6}$alkyl, thereby forming a ring;

each R¹³ is independently selected from hydrogen and $C_{1-6}$alkyl, preferably $C_{1-6}$alkyl; and R¹⁴ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

R¹⁵ is selected from hydrogen, $C_{1-6}$alkyl, $C_{1-6}$hydroxyalkyl, $C_{1-6}$alkoxy, —C(O)OC$_{1-6}$alkyl, —C(O)NHC$_{1-6}$alkyl, and $C_{1-6}$aralkyl, preferably $C_{1-6}$alkyl and $C_{1-6}$hydroxyalkyl, more preferably methyl, ethyl, hydroxymethyl, and 2-hydroxyethyl;

provided that in any occurrence of the sequence ZAZ, at least one member of the sequence must be other than a covalent bond.

In certain embodiments, R¹ is selected from —$C_{1-6}$alkyl-B and $C_{1-6}$aralkyl. In certain such embodiments, R¹ is substituted with one or more substituents selected from hydroxy, halogen, amide, amine, carboxylic acid (or a salt thereof), ester (including $C_{1-6}$alkyl ester, $C_{1-5}$alkylester, and aryl ester), thiol, or thioether. In certain preferred such embodiments, R¹ is substituted with one or more substituents selected from carboxylic acid and ester. In certain embodiments, R¹ is selected from methyl, ethyl, isopropyl, carboxymethyl, and benzyl. In certain embodiments R¹ is —$C_{1-6}$alkyl-B and $C_{1-6}$aralkyl. In certain preferred such embodiments, B is absent.

In certain embodiments, R² is selected from $C_{1-6}$aralkyl and $C_{1-6}$heteroaralkyl. In certain such embodiments, R² is selected from $C_{1-6}$alkyl-phenyl, $C_{1-6}$alkyl-indolyl, $C_{1-6}$alkyl-thienyl, $C_{1-6}$alkyl-thiazolyl, and $C_{1-6}$alkyl-isothiazolyl, wherein the alkyl moiety may contain six, five, four, three, two, or one carbon atoms, preferably one or two. In certain such embodiments, R² is substituted with one or more substituents selected from hydroxy, halogen, amide, amine, carboxylic acid (or a salt thereof), ester (including $C_{1-6}$alkyl ester, $C_{1-5}$alkyl ester, and aryl ester), thiol, or thioether. In certain such embodiments, R² is substituted with a substituent selected from alkyl, trihaloalkyl, alkoxy, hydroxy, or cyano. In certain such embodiments, R² is selected from $C_{1-6}$alkyl-phenyl and $C_{1-6}$alkyl-indolyl. In certain preferred such embodiments, R² is selected from

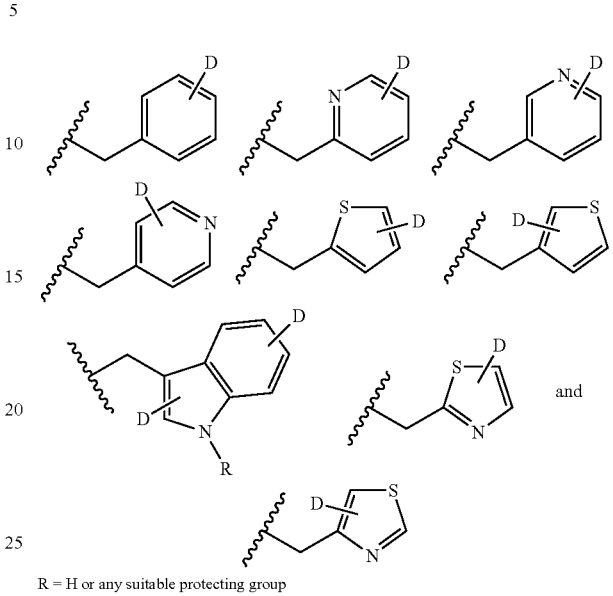

R = H or any suitable protecting group wherein D is selected from H, OMe, OBu$^t$, OH, CN, CF₃ and CH₃. In certain embodiments D is selected from H, OMe, OH, CN, CF₃ and CH₃.

In certain preferred such embodiments where D is attached to a six-membered ring, D is attached at the 4-position relative to the point of attachment, preferably excluding embodiments where the 4-position of the ring is occupied by the nitrogen of a pyridine ring.

In certain embodiments, R³ is selected from $C_{1-6}$aralkyl and $C_{1-6}$heteroaralkyl, wherein the alkyl moiety may contain six, five, four, three, two, or one carbon atoms, preferably one or two. In certain such embodiments, R³ is substituted with one or more substituents selected from hydroxy, halogen, amide, amine, carboxylic acid (or a salt thereof), ester (including $C_{1-6}$alkyl ester, $C_{1-5}$alkyl ester, and aryl ester), thiol, or thioether. In certain such embodiments, R³ is substituted with a substituent selected from alkyl, trihaloalkyl, alkoxy, hydroxy, or cyano. In certain such embodiments, R³ is selected from $C_{1-6}$alkyl-phenyl and $C_{1-6}$alkyl-indolyl. In certain preferred such embodiments, R³ is selected from

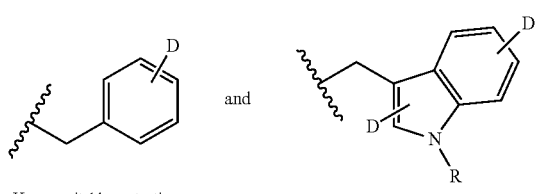

R = H, any suitable protecting group wherein D is selected from H, OMe, OBu$^t$, OH, CN, CF₃ or CH₃. In certain embodiments, D is selected from H, OMe, OH, CN, CF₃ or CH₃.

In certain embodiments, R⁵ is hydrogen, L is C=O or SO₂, R⁶ is Ar—Y—, and each Ar is independently selected from phenyl, indolyl, benzofuranyl, naphthyl, quinolinyl, quinolonyl, thienyl, pyridyl, pyrazyl, and the like. In certain such embodiments, Ar may be substituted with Ar-E-, where E is selected from a direct bond, —O—, and $C_{1-6}$alkyl. In certain other such embodiments where Q is $C_{1-6}$alkyl, Q may be substituted, preferably with Ar, e.g., phenyl.

In certain embodiments, $R^5$ is hydrogen, Q is absent, L is C=O or $SO_2$, and $R^6$ is selected from Ar—Y and heterocyclyl. In certain preferred such embodiments, heterocyclyl is selected from chromonyl, chromanyl, morpholino, and piperidinyl. In certain other preferred such embodiments, Ar is selected from phenyl, indolyl, benzofuranyl, naphthyl, quinolinyl, quinolonyl, thienyl, pyridyl, pyrazyl, and the like.

In certain embodiments, $R^5$ is hydrogen, L is C=O or $SO_2$, Q is absent, and $R^6$ is $C_{1-6}$alkenyl, where $C_{1-6}$alkenyl is a substituted vinyl group where the substituent is preferably an aryl or heteroaryl group, more preferably a phenyl group optionally substituted with one to four substituents.

In certain embodiments, L and Q are absent and $R^6$ is selected from $C_{1-6}$alkyl, $C_{1-6}$alkenyl, $C_{1-6}$alkynyl, $C_{1-6}$aralkyl, and $C_{1-6}$heteroaralkyl. In certain such embodiments, $R^5$ is $C_{1-6}$alkyl and $R^6$ is selected from butyl, allyl, propargyl, phenylmethyl, 2-pyridyl, 3-pyridyl, and 4-pyridyl.

In other embodiments, L is $SO_2$, Q is absent, and $R^6$ is selected from $C_{1-6}$alkyl and aryl. In certain such embodiments, $R^6$ is selected from methyl and phenyl.

In certain embodiments, L is C=O and $R^6$ is selected from $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^{11}$ZA-$C_{1-8}$alkyl-, $R^{14}$Z—$C_{1-8}$alkyl-, $(R^{11}O)(R^{12}O)P(=O)O$—$C_{1-8}$alkyl-, $(R^{11}O)(R^{12}O)P(=O)O$—$C_{1-8}$alkyl-ZAZ—$C_{1-8}$alkyl-, $(R^{11}O)(R^{12}O)P(=O)O$—$C_{1-8}$alkyl-Z—$C_{1-8}$alkyl-, $R^{11}$ZA-$C_{1-8}$alkyl-ZAZ—$C_{1-8}$alkyl-, heterocyclylMZAZ—$C_{1-8}$alkyl-, $(R^{13})_2$N—$C_{1-8}$alkyl-, $(R^{13})_3$N$^+$—$C_{1-8}$alkyl-, heterocyclylM-, carbocyclylM-, $R^{14}SO_2C_{1-8}$alkyl-, and $R^{14}SO_2$NH—, wherein each occurrence of Z and A is independently other than a covalent bond. In certain embodiments, L is C=O, Q is absent, and $R^6$ is H.

In certain embodiments, $R^5$ is $C_{1-6}$alkyl, $R^6$ is $C_{1-6}$alkyl, Q is absent, and L is C=O. In certain such embodiments, $R^6$ is ethyl, isopropyl, 2,2,2-trifluoroethyl, or 2-(methylsulfonyl)ethyl.

In other embodiments, L is C=O, Q is absent, and $R^6$ is $C_{1-6}$aralkyl. In certain such embodiments, $R^6$ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, $R^5$ is $C_{1-6}$alkyl, and $R^6$ is aryl. In certain such embodiments, $R^6$ is substituted or unsubstituted phenyl.

In certain embodiments, L is C=O, Q is absent, and $R^6$ is selected from heteroaryl and $C_{1-6}$heteroaralkyl. In certain such embodiments, $R^6$ is heteroaryl selected from pyrrole, furan, thiophene, imidazole, isoxazole, oxazole, oxadiazole, thiazole, thiadiazole, triazole, pyrazole, pyridine, pyrazine, pyridazine and pyrimidine. In certain alternative such embodiments, $R^6$ is $C_{1-6}$heteroaralkyl selected from pyrrolylmethyl, furanylmethyl, thienylmethyl, imidazolylmethyl, isoxazolylmethyl, oxazolylmethyl, oxadiazolylmethyl, thiazolylmethyl, thiadiazolylmethyl, triazolylmethyl, pyrazolylmethyl, pyridylmethyl, pyrazinylmethyl, pyridazinylmethyl and pyrimidinylmethyl.

In certain embodiments, L is C=O, Q is absent or O, and $R^6$ is carbocyclylM-, wherein M is $C_{0-1}$alkyl. In certain such embodiments, $R^6$ is cyclopropyl or cyclohexyl.

In certain embodiments, L and A are C=O, Q is absent, Z is O, M is $C_{1-8}$alkyl, preferably methylene, and $R^6$ is selected from $R^{11}$ZA-$C_{1-8}$alkyl-, $R^{14}$Z—$C_{1-8}$alkyl-, $R^{11}$ZA-$C_{1-8}$alkyl-ZAZ— $C_{1-8}$ alkyl-, $(R^{11}O)(R^{12}O)P(=O)O$—$C_{1-8}$alkyl-ZAZ—$C_{1-8}$alkyl-, $(R^{11}O)(R^{12}O)P(=O)O$—$C_{1-8}$alkyl-Z—$C_{1-8}$alkyl-, and heterocyclylMZAZ—$C_{1-8}$alkyl-, wherein each occurrence of A is independently other than a covalent bond. In certain such embodiments, $R^6$ is heterocyclylMZAZ—$C_{1-8}$alkyl- where heterocyclyl is substituted or unsubstituted oxodioxolenyl or N(R wherein $R^{16}$ and $R^{17}$ together are $C_{1-6}$alkyl-Y—$C_{1-6}$alkyl, preferably $C_{1-3}$alkyl-Y—$C_{1-3}$alkyl, thereby forming a ring.

In certain preferred embodiments, L is C=O, Q is absent, M is $C_{1-8}$alkyl, and $R^6$ is selected from $(R^{11}O)(R^{12}O)P(=O)O$—$C_{1-8}$alkyl-, $(R^{13})_2NC_{1-8}$alkyl, $(R^{13})_3N^+C_{1-8}$alkyl-, and heterocyclyl-M-. In certain such embodiments, $R^6$ is $(R^{13})_2NC_{1-8}$alkyl or $(R^{13})_3N^+C_{1-8}$alkyl-, where $R^{13}$ is $C_{1-6}$alkyl. In certain other such embodiments, $R^6$ is heterocyclylM-, where heterocyclyl is selected from morpholino, piperidino, piperazino, and pyrrolidino.

In certain embodiments, L is C=O, $R^5$ is $C_{1-6}$alkyl, Q is selected from O and NH and $R^6$ is selected from $C_{1-6}$alkyl, cycloalkyl-M, $C_{1-6}$aralkyl, and $C_{1-6}$heteroaralkyl. In other embodiments, L is C=O, $R^5$ is $C_{1-6}$alkyl, Q is selected from O and NH and $R^6$ is $C_{1-6}$alkyl, where $C_{1-6}$alkyl is selected from methyl, ethyl, and isopropyl. In further embodiments, L is C=O, $R^5$ is $C_{1-6}$alkyl, Q is selected from O and NH and $R^6$ is $C_{1-6}$aralkyl, where aralkyl is phenylmethyl. In other embodiments, L is C=O, $R^5$ is $C_{1-6}$alkyl, Q is selected from O and NH, and $R^6$ is $C_{1-6}$heteroaralkyl, where heteroaralkyl is (4-pyridyl)methyl.

In certain embodiments, L is absent or is C=O, and $R^5$ and $R^6$ together are $C_{1-6}$alkyl-Y—$C_{1-6}$alkyl, $C_{1-6}$alkyl-ZA-$C_{1-6}$alkyl, or $C_{1-6}$alkyl-A, wherein each occurrence of Z and A is independently other than a covalent bond, thereby forming a ring. In certain preferred embodiments, L is C=O, Q and Y are absent, and $R^5$ and $R^6$ together are $C_{1-3}$alkyl-Y—$C_{1-3}$alkyl. In another preferred embodiment, L and Q are absent, and $R^5$ and $R^6$ together are $C_{1-3}$alkyl-Y—$C_{1-3}$alkyl. In another preferred embodiment, L is C=O, Q is absent, Y is selected from NH and N—$C_{1-4}$alkyl, and $R^5$ and $R^6$ together are $C_{1-3}$alkyl-Y—$C_{1-3}$alkyl. In another preferred embodiment, L is C=O, Y is absent, and $R^5$ and $R^6$ together are $C_{1-3}$alkyl-Y—$C_{1-3}$alkyl. In another preferred embodiment, L and A are C=O, and $R^5$ and $R^6$ together are $C_{1-2}$alkyl-ZA-$C_{1-2}$alkyl. In another preferred embodiment, L and A are C=O and $R^5$ and $R^6$ together are $C_{2-3}$alkyl-A.

In certain embodiments, $R^7$ and $R^8$ are independently selected from hydrogen and $C_{1-6}$alkyl. In certain preferred such embodiments, $R^7$ and $R^8$ are independently selected from hydrogen and methyl. In more preferred such embodiments, $R^7$ and $R^8$ are both hydrogen.

In certain embodiments, X is O, $R^2$ and $R^3$ are each independently $C_{1-6}$aralkyl, and $R^1$ is selected from $C_{1-6}$alkyl, $C_{1-6}$hydroxyalkyl, $C_{1-6}$alkoxyalkyl, aryl, and $C_{1-6}$aralkyl, any of which is optionally substituted with one or more of amide, amine, carboxylic acid (or a salt thereof), ester (including $C_{1-6}$alkyl ester, $C_{1-5}$alkyl ester, and aryl ester), thiol, or thioether substituents.

Suitable N-terminal protecting groups known in the art of peptide syntheses, include t-butoxy carbonyl (Boc), benzoyl (Bz), fluoren-9-ylmethoxycarbonyl (Fmoc), triphenylmethyl (trityl) and trichloroethoxycarbonyl (Troc) and the like. The use of various N-protecting groups, e.g., the benzyloxy carbonyl group or the t-butyloxycarbonyl group (Boc), various coupling reagents, e.g., dicyclohexylcarbodiimide (DCC), 1,3-diisopropylcarbodiimide (DIC), 1-(3-dimethylaminopropyl)-3-ethylcarbodiimide (EDC), N-hydroxyazabenzotriazole (HATU), carbonyldiimidazole, or 1-hydroxybenzotriazole monohydrate (HOBT), and various cleavage conditions: for example, trifluoracetic acid (TFA), HCl in dioxane, hydrogenation on Pd—C in organic solvents (such as methanol or ethyl acetate), boron tris(trifluoroacetate), and cyanogen bromide, and reaction in solution with isolation and purification of intermediates are well-known in the art of peptide synthesis, and are equally applicable to the preparation of the subject compounds. Suitable protecting N-terminal protecting groups may also be found, for example, in Greene, T. W.; Wuts, P. G. M. "Protective Groups in Organic Synthesis", 3rd ed.; Wiley: New York, 1999 or Kocieński, P. J., "Protecting Groups", Georg Thieme Verlag, 1994.

In certain embodiments, the stereochemical configuration of the carbons bearing $R^1$, $R^2$, or $R^3$ are independently D or L. In certain preferred embodiments, the stereochemical configuration of at least one of the carbons bearing $R^1$, $R^2$, and $R^3$ respectively is D. In certain preferred such embodiments, the stereochemical configuration of the carbon bearing $R^1$ is D. In certain such embodiments, the stereochemical configuration of the carbon bearing $R^2$ is D. In certain such embodiments, the stereochemical configuration of the carbon bearing $R^3$ is D. In certain embodiments the stereochemical configuration of at least two of the carbons bearing $R^1$, $R^2$, and $R^3$ respectively is D. In yet another preferred embodiment, the stereochemical configuration of all three of the carbons bearing $R^1$, $R^2$, and $R^3$ respectively is D.

Another aspect of the invention relates to compounds having a structure of formula (II) or a pharmaceutically acceptable salt thereof, (II)

each Ar is independently an aromatic or heteroaromatic group optionally substituted with 1 to 4 substituents;
each A is independently selected from C=O, C=S, and $SO_2$, preferably C=O; or
A is optionally a covalent bond when adjacent to an occurrence of Z;
B is absent or is $N(R^9)R^{10}$, preferably absent;
L is absent or is selected from C=O, C=S, and $SO_2$, preferably $SO_2$ or C=O;
M is absent or is $C_{1-12}$alkyl, preferably $C_{1-8}$alkyl;
Q is absent or is selected from O, NH, and N—$C_{1-6}$alkyl;
X is selected from O, S, NH, and N—$C_{1-6}$alkyl, preferably O;
Y is absent or is selected from C=O and $SO_2$;
each Z is independently selected from O, S, NH, and N—$C_{1-6}$alkyl, preferably O; or
Z is optionally a covalent bond when adjacent to an occurrence of A;
$R^2$ and $R^3$ are each independently selected from aryl, $C_{1-6}$aralkyl, heteroaryl, and $C_{1-6}$heteroaralkyl;
$R^4$ is $N(R^5)L$-Q-$R^6$;
$R^5$ is selected from hydrogen, OH, $C_{1-6}$aralkyl, and $C_{1-6}$alkyl, preferably hydrogen;
$R^6$ is selected from hydrogen, $C_{1-6}$alkyl, $C_{1-6}$alkenyl, $C_{1-6}$alkynyl, Ar—Y—, carbocyclyl, heterocyclyl, an N-terminal protecting group, aryl, $C_{1-6}$aralkyl, heteroaryl, $C_{1-6}$heteroaralkyl, $R^{11}$ZAZ—$C_{1-8}$alkyl-, $R^{14}$Z—$C_{1-8}$alkyl-, $(R^{11}O)(R^{12}O)P(=O)O$—$C_{1-8}$alkyl-ZAZ—$C_{1-8}$alkyl-, $R^{11}$ZAZ—$C_{1-8}$alkyl-ZAZ—$C_{1-8}$alkyl-, heterocyclylMZAZ—$C_{1-8}$alkyl-, $(R^{11}O)(R^{12}O)P(=O)O$—$C_{1-8}$alkyl-, $(R^{13})_2N$—$C_{1-12}$alkyl-, $(R^{13})_3N^+$—$C_{1-12}$alkyl-, heterocyclylM-, carbocyclylM-, $R^{14}SO_2C_{1-8}$alkyl-, and $R^{14}SO_2NH$; preferably an N-capping group, more preferably t-butoxycarbonyl or benzyloxycarbonyl; or $R^5$ and $R^6$ together are $C_{1-6}$alkyl-Y—$C_{1-6}$alkyl, $C_{1-6}$alkyl-ZAZ—$C_{1-6}$alkyl, ZAZ—$C_{1-6}$alkyl-ZAZ—$C_{1-6}$alkyl, ZAZ—$C_{1-6}$alkyl-ZAZ, or $C_{1-6}$alkyl-A, thereby forming a ring;
$R^8$ is selected from hydrogen, $C_{1-6}$alkyl, and $C_{1-6}$aralkyl, preferably hydrogen;
$R^9$ is selected from hydrogen, OH, and $C_{1-6}$alkyl, preferably $C_{1-6}$alkyl; and
$R^{10}$ is an N-terminal protecting group;
$R^{11}$ and $R^{12}$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^{11}$ and $R^{12}$ together are $C_{1-6}$alkyl, thereby forming a ring;
each $R^{13}$ is independently selected from hydrogen and $C_{1-6}$alkyl, preferably $C_{1-6}$alkyl; and
$R^{14}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;
$R^{15}$ is selected from hydrogen, $C_{1-6}$alkyl, $C_{1-6}$hydroxyalkyl, $C_{1-6}$alkoxy, —C(O)O$C_{1-6}$alkyl, —C(O)NH$C_{1-6}$alkyl, and $C_{1-6}$aralkyl, preferably $C_{1-6}$alkyl and $C_{1-6}$hydroxyalkyl, more preferably methyl, ethyl, hydroxymethyl, and 2-hydroxyethyl;
provided that in any occurrence of the sequence ZAZ, at least one member of the sequence must be other than a covalent bond.

In certain embodiments, $R^2$ is selected from $C_{1-6}$aralkyl and $C_{1-6}$heteroaralkyl. In certain such embodiments, $R^2$ is selected from $C_{1-6}$alkyl-phenyl, $C_{1-6}$alkyl-indolyl, $C_{1-6}$alkyl-thienyl, $C_{1-6}$alkyl-thiazolyl, and $C_{1-6}$alkyl-isothiazolyl, wherein the alkyl moiety may contain six, five, four, three, two, or one carbon atoms, preferably one or two. In certain such embodiments, $R^2$ is substituted with one or more substituents selected from hydroxy, halogen, amide, amine, carboxylic acid (or a salt thereof), ester (including $C_{1-6}$alkyl ester, $C_{1-5}$alkyl ester, and aryl ester), thiol, or thioether. In certain such embodiments, $R^2$ is substituted with a substituent selected from alkyl, trihaloalkyl, alkoxy, hydroxy, or cyano. In certain such embodiments, $R^2$ is selected from $C_{1-6}$alkyl-phenyl and $C_{1-6}$alkyl-indolyl. In certain preferred such embodiments, $R^2$ is selected from R = H or any suitable protecting group wherein D is selected from H, OMe, OBu$^t$, OH, CN, $CF_3$ and $CH_3$. In certain embodiments D is selected from H, OMe, OH, CN, $CF_3$ and $CH_3$.

In certain preferred such embodiments where D is attached to a six-membered ring, D is attached at the 4-position relative to the point of attachment, preferably excluding embodiments where the 4-position of the ring is occupied by the nitrogen of a pyridine ring.

In certain embodiments, $R^3$ is selected from $C_{1-6}$aralkyl and $C_{1-6}$heteroaralkyl. In certain the alkyl moiety may contain six, five, four, three, two, or one carbon atoms, preferably one or two. In certain such embodiments, $R^3$ is substituted with one or more substituents selected from hydroxy, halogen, amide, amine, carboxylic acid (or a salt thereof), ester (including $C_{1-6}$alkyl ester, $C_{1-5}$alkyl ester, and aryl ester), thiol, or thioether. In certain such embodiments, $R^3$ is substituted with a substituent selected from alkyl, trihaloalkyl, alkoxy, hydroxy, or cyano. In certain such embodiments, $R^3$ is selected from $C_{1-6}$alkyl-phenyl and $C_{1-6}$alkyl-indolyl. In certain preferred such embodiments, $R^3$ is selected from

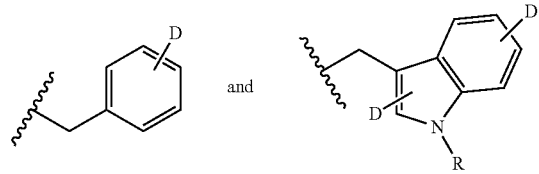

R = H, any suitable protecting group wherein D is selected from H, OMe, OBu$^t$, OH, CN, CF$_3$ or CH$_3$. In certain embodiments, D is selected from H, OMe, OH, CN, CF$_3$ or CH$_3$.

In certain embodiments, $R^5$ is hydrogen, L is C=O or SO$_2$, $R^6$ is Ar—Y—, and each Ar is independently selected from phenyl, indolyl, benzofuranyl, naphthyl, quinolinyl, quinolonyl, thienyl, pyridyl, pyrazyl, and the like. In certain such embodiments, Ar may be substituted with Ar-E-, where E is selected from a direct bond, —O—, and $C_{1-6}$alkyl. In certain other such embodiments where Q is $C_{1-6}$alkyl, Q may be substituted, preferably with Ar, e.g., phenyl.

In certain embodiments, $R^5$ is hydrogen, Q is absent, L is C=O or SO$_2$, and $R^6$ is selected from Ar—Y and heterocyclyl. In certain preferred such embodiments, heterocyclyl is selected from chromonyl, chromanyl, morpholino, and piperidinyl. In certain other preferred such embodiments, Ar is selected from phenyl, indolyl, benzofuranyl, naphthyl, quinolinyl, quinolonyl, thienyl, pyridyl, pyrazyl, and the like.

In certain embodiments, $R^5$ is hydrogen, L is C=O or SO$_2$, Q is absent, and $R^6$ is $C_{1-6}$alkenyl, where $C_{1-6}$alkenyl is a substituted vinyl group where the substituent is preferably an aryl or heteroaryl group, more preferably a phenyl group optionally substituted with one to four substituents.

In certain embodiments, L and Q are absent and $R^6$ is selected from $C_{1-6}$alkyl, $C_{1-6}$alkenyl, $C_{1-6}$alkynyl, $C_{1-6}$aralkyl, and $C_{1-6}$heteroaralkyl. In certain such embodiments, $R^5$ is $C_{1-6}$alkyl and $R^6$ is selected from butyl, allyl, propargyl, phenylmethyl, 2-pyridyl, 3-pyridyl, and 4-pyridyl.

In other embodiments, L is SO$_2$, Q is absent, and $R^6$ is selected from $C_{1-6}$alkyl and aryl. In certain such embodiments, $R^6$ is selected from methyl and phenyl.

In certain embodiments, L is C=O and $R^6$ is selected from $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^{11}$ZA-$C_{1-8}$alkyl-, $R^{14}$Z—$C_{1-8}$alkyl-, $(R^{11}O)(R^{12}O)P(=O)—C_{1-8}$alkyl-, $(R^{11}O)(R^{12}O)P(=O)O—C_{1-8}$alkyl-ZAZ—$C_{1-8}$alkyl-, $(R^{11}O)(R^{12}O)P(=O)O—C_{1-8}$alkyl-Z—$C_{1-8}$alkyl-, $R^{11}$ZA-$C_{1-8}$alkyl-ZAZ—$C_{1-8}$alkyl-, heterocyclylMZAZ—$C_{1-8}$alkyl-, $(R^{13})_2$N—$C_{1-8}$alkyl-, $(R^{13})_3$N$^+$—$C_{1-8}$alkyl-, heterocyclylM-, carbocyclylM-, $R^{14}$SO$_2C_{1-8}$alkyl-, and $R^{14}$SO$_2$NH—, wherein each occurrence of Z and A is independently other than a covalent bond. In certain embodiments, L is C=O, Q is absent, and $R^6$ is H.

In certain embodiments, $R^5$ is $C_{1-6}$alkyl, $R^6$ is $C_{1-6}$alkyl, Q is absent, and L is C=O. In certain such embodiments, $R^6$ is ethyl, isopropyl, 2,2,2-trifluoroethyl, or 2-(methylsulfonyl)ethyl.

In other embodiments, L is C=O, Q is absent, and $R^6$ is $C_{1-6}$aralkyl. In certain such embodiments, $R^6$ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, $R^5$ is $C_{1-6}$alkyl, and $R^6$ is aryl. In certain such embodiments, $R^6$ is substituted or unsubstituted phenyl.

In certain embodiments, L is C=O, Q is absent, and $R^6$ is selected from heteroaryl and $C_{1-6}$heteroaralkyl. In certain such embodiments, $R^6$ is heteroaryl selected from pyrrole, furan, thiophene, imidazole, isoxazole, oxazole, oxadiazole, thiazole, thiadiazole, triazole, pyrazole, pyridine, pyrazine, pyridazine and pyrimidine. In certain alternative such embodiments, $R^6$ is $C_{1-6}$heteroaralkyl selected from pyrrolylmethyl, furanylmethyl, thienylmethyl, imidazolylmethyl, isoxazolylmethyl, oxazolylmethyl, oxadiazolylmethyl, thiazolylmethyl, thiadiazolylmethyl, triazolylmethyl, pyrazolylmethyl, pyridylmethyl, pyrazinylmethyl, pyridazinylmethyl and pyrimidinylmethyl.

In certain embodiments, L is C=O, Q is absent or O, and $R^6$ is carbocyclylM-, wherein M is $C_{0-1}$alkyl. In certain such embodiments, $R^6$ is cyclopropyl or cyclohexyl.

In certain embodiments, L and A are C=O, Q is absent, Z is O, M is $C_{1-8}$alkyl, preferably methylene, and $R^6$ is selected from $R^{11}$ZA-$C_{1-8}$alkyl-, $R^{14}$Z—$C_{1-8}$alkyl-, $R^{11}$ZA-$C_{1-8}$alkyl-ZAZ—$C_{1-8}$alkyl-, $(R^{11}O)(R^{12}O)P(=O)O—C_{1-8}$alkyl-ZAZ—$C_{1-8}$alkyl-, $(R^{11}O)(R^{12}O)P(=O)O—C_{1-8}$alkyl-Z—$C_{1-8}$alkyl-, and heterocyclylMZAZ—$C_{1-8}$alkyl-, wherein each occurrence of A is independently other than a covalent bond. In certain such embodiments, $R^6$ is heterocyclylMZAZ—$C_{1-8}$alkyl- where heterocyclyl is substituted or unsubstituted oxodioxolenyl or $N(R^{16})(R^{17})$, wherein $R^{16}$ and $R^{17}$ together are $C_{1-6}$alkyl-Y—$C_{1-6}$alkyl, preferably $C_{1-3}$alkyl-Y—$C_{1-3}$alkyl, thereby forming a ring.

In certain preferred embodiments, L is C=O, Q is absent, M is $C_{1-8}$alkyl, and $R^6$ is selected from $(R^{11}O)(R^{12}O)P(=O)O—C_{1-8}$alkyl-, $(R^{13})_2NC_{1-8}$alkyl, $(R^{13})_3N^+C_{1-8}$alkyl-, and heterocyclyl-M-. In certain such embodiments, $R^6$ is $(R^{13})_2NC_{1-8}$alkyl or $(R^{13})_3N^+C_{1-8}$alkyl-, where $R^{13}$ is $C_{1-6}$alkyl. In certain other such embodiments, $R^6$ is heterocyclylM-, where heterocyclyl is selected from morpholino, piperidino, piperazino, and pyrrolidino.

In certain embodiments, L is C=O, $R^5$ is $C_{1-6}$alkyl, Q is selected from O and NH and $R^6$ is selected from $C_{1-6}$alkyl, cycloalkyl-M, $C_{1-6}$aralkyl, and $C_{1-6}$heteroaralkyl. In other embodiments, L is C=O, $R^5$ is $C_{1-6}$alkyl, Q is selected from O and NH, and $R^6$ is $C_{1-6}$alkyl, where $C_{1-6}$alkyl is selected from methyl, ethyl, and isopropyl. In further embodiments, L is C=O, $R^5$ is $C_{1-6}$alkyl, Q is selected from O and NH and $R^6$ is $C_{1-6}$aralkyl, where aralkyl is phenylmethyl. In other embodiments, L is C=O, $R^5$ is $C_{1-6}$alkyl, Q is selected from O and NH, and $R^6$ is $C_{1-6}$heteroaralkyl, where heteroaralkyl is (4-pyridyl)methyl.

In certain embodiments, L is absent or is C=O, and $R^5$ and $R^6$ together are $C_{1-6}$alkyl-Y—$C_{1-6}$alkyl, $C_{1-6}$alkyl-ZA-$C_{1-6}$alkyl, or $C_{1-6}$alkyl-A, wherein each occurrence of Z and A is independently other than a covalent bond, thereby forming a ring. In certain preferred embodiments, L is C=O, Q and Y are absent, and $R^5$ and $R^6$ together are $C_{1-3}$alkyl-Y—$C_{1-3}$alkyl. In another preferred embodiment, L and Q are absent, and $R^5$ and $R^6$ together are $C_{1-3}$alkyl-Y—$C_{1-3}$alkyl. In another preferred embodiment, L is C=O, Q is absent, Y is selected from NH and N—$C_{1-6}$alkyl, and $R^5$ and $R^6$ together are $C_{1-3}$alkyl-Y—$C_{1-3}$alkyl. In another preferred embodiment, L is C=O, Y is absent, and $R^5$ and $R^6$ together are $C_{1-3}$alkyl-Y—$C_{1-3}$alkyl. In another preferred embodiment, L and A are C=O, and $R^5$ and $R^6$ together are $C_{1-2}$alkyl-ZA-$C_{1-2}$alkyl. In another preferred embodiment, L and A are C=O and $R^5$ and $R^6$ together are $C_{2-3}$alkyl-A.

In certain embodiments, $R^8$ is selected from hydrogen and $C_{1-6}$alkyl. In certain preferred such embodiments, $R^8$ is selected from hydrogen and methyl. In more preferred such embodiments, $R^8$ is hydrogen.

In certain embodiments, X is O, $R^2$ and $R^3$ are each independently $C_{1-6}$aralkyl, and $R^1$ is selected from $C_{1-6}$alkyl, $C_{1-6}$hydroxyalkyl, $C_{1-6}$alkoxyalkyl, aryl, and $C_{1-6}$aralkyl, any of which is optionally substituted with one or more of amide, amine, carboxylic acid (or a salt thereof), ester (including $C_{1-6}$alkyl ester, $C_{1-5}$alkyl ester, and aryl ester), thiol, or thioether substituents.

In certain embodiments, the stereochemical configuration of the carbons bearing $R^2$ or $R^3$ are independently D or L. In certain preferred embodiments, the stereochemical configuration of at least one of the carbons bearing $R^2$ and $R^3$ respectively is D. In certain such embodiments, the stereochemical configuration of the carbon bearing $R^2$ is D. In such embodiments, the stereochemical configuration of the carbon bearing $R^3$ is D. In certain embodiments, the stereochemical configuration of both of the carbons bearing $R^2$ and $R^3$ respectively is D.

Another aspect of the invention relates to compounds having a structure of formula (III) or a pharmaceutically acceptable salt thereof,

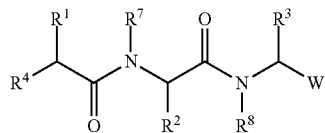

(III)

wherein
each A is independently selected from C=O, C=S, and $SO_2$, preferably C=O; or
A is optionally a covalent bond when adjacent to an occurrence of Z;
B is absent or is $N(R^9)R^{10}$, preferably absent;
L is absent or is selected from C=O, C=S, and $SO_2$, preferably $SO_2$ or C=O;
M is absent or is $C_{1-12}$alkyl, preferably $C_{1-8}$alkyl;
W is selected from —CHO and —B(OR$^{11}$)$_2$;
Q is absent or is selected from O, NH, and N—$C_{1-6}$alkyl;
Y is absent or is selected from C=O and $SO_2$;
each Z is independently selected from O, S, NH, and N—$C_{1-6}$alkyl, preferably O; or
Z is optionally a covalent bond when adjacent to an occurrence of A;
$R^1$ is selected from H, —$C_{1-6}$alkyl-B, $C_{1-6}$hydroxyalkyl, $C_{1-6}$alkoxyalkyl, aryl, and $C_{1-6}$aralkyl;
$R^2$ and $R^3$ are each independently selected from aryl, $C_{1-6}$aralkyl, heteroaryl, and $C_{1-6}$heteroaralkyl;
$R^4$ is $N(R^5)$L-Q-$R^6$;

$R^5$ is selected from hydrogen, OH, $C_{1-6}$aralkyl, and $C_{1-6}$alkyl, preferably hydrogen;

$R^6$ is selected from hydrogen, $C_{1-6}$alkyl, $C_{1-6}$alkenyl, $C_{1-6}$alkynyl, Ar—Y—, carbocyclyl, heterocyclyl, an N-terminal protecting group, aryl, $C_{1-6}$aralkyl, heteroaryl, $C_{1-6}$heteroaralkyl, $R^{11}$ZAZ—$C_{1-8}$alkyl-, $R^{14}$Z—$C_{1-18}$alkyl-, $(R^{11}O)(R^{12}O)P(=O)O$—$C_{1-8}$alkyl-ZAZ—$C_{1-8}$alkyl-, $R^{11}$ZAZ—$C_{1-8}$alkyl-ZAZ—$C_{1-8}$alkyl-, heterocyclylMZAZ—$C_{1-8}$alkyl-, $(R^{11}O)(R^{12}O)P(=O)O$—$C_{1-8}$alkyl-, $(R^{13})_2$N—$C_{1-12}$alkyl-, $(R^{13})_3$N$^+$—$C_{1-12}$alkyl-, heterocyclylM-, carbocyclylM-, $R^{14}SO_2C_{1-8}$alkyl-, and $R^{14}SO_2$NH; preferably an N-capping group, more preferably t-butoxycarbonyl or benzyloxycarbonyl; or $R^5$ and $R^6$ together are $C_{1-6}$alkyl-Y—$C_{1-6}$alkyl, $C_{1-6}$alkyl-ZAZ—$C_{1-6}$alkyl, ZAZ—$C_{1-6}$alkyl-ZAZ—$C_{1-16}$alkyl, ZAZ—$C_{1-6}$alkyl-ZAZ, or $C_{1-6}$alkyl-A, thereby forming a ring;

$R^7$ and $R^8$ are independently selected from hydrogen, $C_{1-6}$alkyl, and $C_{1-6}$aralkyl, preferably hydrogen;

$R^9$ is selected from hydrogen, OH, and $C_{1-6}$alkyl, preferably $C_{1-6}$alkyl; and $R^{10}$ is an N-terminal protecting group;

$R^{11}$ and $R^{12}$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^{11}$ and $R^{12}$ together are $C_{1-6}$alkyl, thereby forming a ring;

each $R^{13}$ is independently selected from hydrogen and $C_{1-6}$alkyl, preferably $C_{1-6}$alkyl; and $R^{14}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

each $R^{16}$ is independently selected from hydrogen and $C_{1-6}$alkyl; or two occurrences of $R^{11}$ together may be $C_{1-6}$alkyl, thereby forming a ring together with the intervening boron and oxygen atoms to which they are attached;

provided that in any occurrence of the sequence ZAZ, at least one member of the sequence must be other than a covalent bond.

In certain embodiments, $R^1$ is selected from —$C_{1-6}$alkyl-B and $C_{1-6}$aralkyl. In certain such embodiments, $R^1$ is substituted with one or more substituents selected from hydroxy, halogen, amide, amine, carboxylic acid (or a salt thereof), ester (including $C_{1-6}$alkyl ester, $C_{1-5}$alkyl ester, and aryl ester), thiol, or thioether. In certain preferred such embodiments, $R^1$ is substituted with one or more substituents selected from carboxylic acid and ester. In certain embodiments, $R^1$ is selected from methyl, ethyl, isopropyl, carboxymethyl, and benzyl. In certain embodiments $R^1$ is —$C_{1-6}$alkyl-B and $C_{1-6}$aralkyl. In certain preferred such embodiments, B is absent.

In certain embodiments, $R^2$ is selected from $C_{1-6}$aralkyl and $C_{1-6}$heteroaralkyl. In certain such embodiments, $R^2$ is selected from $C_{1-6}$alkyl-phenyl, $C_{1-6}$alkyl-indolyl, $C_{1-6}$alkyl-thienyl, $C_{1-6}$alkyl-thiazolyl, and $C_{1-6}$alkyl-isothiazolyl, wherein the alkyl moiety may contain six, five, four, three, two, or one carbon atoms, preferably one or two. In certain such embodiments, $R^2$ is substituted with one or more substituents selected from hydroxy, halogen, amide, amine, carboxylic acid (or a salt thereof), ester (including $C_{1-6}$alkyl ester, $C_{1-5}$alkyl ester, and aryl ester), thiol, or thioether. In certain such embodiments, $R^2$ is substituted with a substituent selected from alkyl, trihaloalkyl, alkoxy, hydroxy, or cyano. In certain such embodiments, $R^2$ is selected from $C_{1-6}$alkyl-phenyl and $C_{1-6}$alkyl-indolyl. In certain preferred such embodiments, $R^2$ is selected from

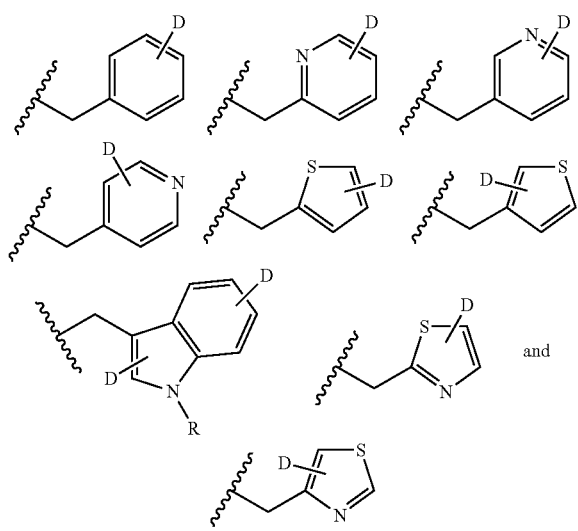

R = H or any suitable protecting group wherein D is selected from H, OMe, OBu$^t$, OH, CN, CF$_3$ and CH$_3$. In certain embodiments D is selected from H, OMe, OH, CN, CF$_3$ and CH$_3$.

In certain preferred such embodiments where D is attached to a six-membered ring, D is attached at the 4-position relative to the point of attachment, preferably excluding embodiments where the 4-position of the ring is occupied by the nitrogen of a pyridine ring.

In certain embodiments, $R^3$ is selected from $C_{1-6}$aralkyl and $C_{1-6}$heteroaralkyl. In certain the alkyl moiety may contain six, five, four, three, two, or one carbon atoms, preferably one or two. In certain such embodiments, $R^3$ is substituted with one or more substituents selected from hydroxy, halogen, amide, amine, carboxylic acid (or a salt thereof), ester (including $C_{1-6}$alkyl ester, $C_{1-5}$alkyl ester, and aryl ester), thiol, or thioether. In certain such embodiments, $R^3$ is substituted with a substituent selected from alkyl, trihaloalkyl, alkoxy, hydroxy, or cyano. In certain such embodiments, $R^3$ is selected from $C_{1-6}$alkyl-phenyl and $C_{1-6}$alkyl-indolyl. In certain preferred such embodiments, $R^3$ is selected from

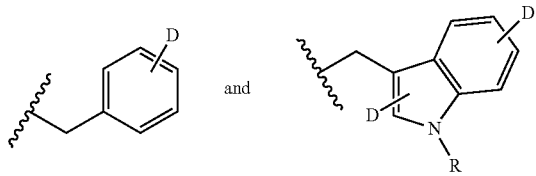

R = H, any suitable protecting group wherein D is selected from H, OMe, OBu$^t$, OH, CN, CF$_3$ or CH$_3$. In certain embodiments, D is selected from H, OMe, OH, CN, CF$_3$ or CH$_3$.

In certain embodiments, $R^5$ is hydrogen, L is C=O or SO$_2$, $R^6$ is Ar—Y—, and each Ar is independently selected from phenyl, indolyl, benzofuranyl, naphthyl, quinolinyl, quinolonyl, thienyl, pyridyl, pyrazyl, and the like. In certain such embodiments, Ar may be substituted with Ar-E-, where E is selected from a direct bond, —O—, and $C_{1-6}$alkyl. In certain other such embodiments where Q is $C_{1-6}$alkyl, Q may be substituted, preferably with Ar, e.g., phenyl.

In certain embodiments, $R^5$ is hydrogen, Q is absent, L is C=O or SO$_2$, and $R^6$ is selected from Ar—Y and heterocyclyl. In certain preferred such embodiments, heterocyclyl is selected from chromonyl, chromanyl, morpholino, and piperidinyl. In certain other preferred such embodiments, Ar is selected from phenyl, indolyl, benzofuranyl, naphthyl, quinolinyl, quinolonyl, thienyl, pyridyl, pyrazyl, and the like.

In certain embodiments, $R^5$ is hydrogen, L is C=O or SO$_2$, Q is absent, and $R^6$ is $C_{1-6}$alkenyl, where $C_{1-6}$alkenyl is a substituted vinyl group where the substituent is preferably an aryl or heteroaryl group, more preferably a phenyl group optionally substituted with one to four substituents.

In certain embodiments, L and Q are absent and $R^6$ is selected from $C_{1-6}$alkyl, $C_{1-6}$alkenyl, $C_{1-6}$alkynyl, $C_{1-6}$aralkyl, and $C_{1-6}$heteroaralkyl. In certain such embodiments, $R^5$ is $C_{1-6}$alkyl and $R^6$ is selected from butyl, allyl, propargyl, phenylmethyl, 2-pyridyl, 3-pyridyl, and 4-pyridyl.

In other embodiments, L is SO$_2$, Q is absent, and $R^6$ is selected from $C_{1-6}$alkyl and aryl. In certain such embodiments, $R^6$ is selected from methyl and phenyl.

In certain embodiments, L is C=O and $R^6$ is selected from $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^{11}$ZA-$C_{1-8}$alkyl-, $R^{14}$Z—$C_{1-8}$alkyl-, $(R^{11}O)(R^{12}O)P(=O)O$—$C_{1-8}$alkyl-, $(R^{11}O)(R^{12}O)P(=O)O$—$C_{1-8}$alkyl-ZAZ—$C_{1-8}$alkyl-, $(R^{11}O)(R^{12}O)P(=O)O$—$C_{1-8}$alkyl-Z—$C_{1-8}$alkyl-, $R^{11}$ZA-$C_{1-8}$alkyl-ZAZ—$C_{1-8}$alkyl-, heterocyclylMZAZ—$C_{1-8}$alkyl-, $(R^{13})_2$N—$C_{1-8}$alkyl-, $(R^{13})_3$N$^+$—$C_{1-8}$alkyl-, heterocyclylM-, carbocyclylM-, $R^{14}$SO$_2$C$_{1-8}$alkyl-, and $R^{14}$SO$_2$NH—, wherein each occurrence of Z and A is independently other than a covalent bond. In certain embodiments, L is C=O, Q is absent, and $R^6$ is H.

In certain embodiments, $R^5$ is $C_{1-6}$alkyl, $R^6$ is $C_{1-6}$alkyl, Q is absent, and L is C=O. In certain such embodiments, $R^6$ is ethyl, isopropyl, 2,2,2-trifluoroethyl, or 2-(methylsulfonyl)ethyl.

In other embodiments, L is C=O, Q is absent, and $R^6$ is $C_{1-6}$aralkyl. In certain such embodiments, $R^6$ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, $R^5$ is $C_{1-6}$alkyl, and $R^6$ is aryl. In certain such embodiments, $R^6$ is substituted or unsubstituted phenyl.

In certain embodiments, L is C=O, Q is absent, and $R^6$ is selected from heteroaryl and $C_{1-6}$heteroaralkyl. In certain such embodiments, $R^6$ is heteroaryl selected from pyrrole, furan, thiophene, imidazole, isoxazole, oxazole, oxadiazole, thiazole, thiadiazole, triazole, pyrazole, pyridine, pyrazine, pyridazine and pyrimidine. In certain alternative such embodiments, $R^6$ is $C_{1-6}$heteroaralkyl selected from pyrrolylmethyl, furanylmethyl, thienylmethyl, imidazolylmethyl, isoxazolylmethyl, oxazolylmethyl, oxadiazolylmethyl, thiazolylmethyl, thiadiazolylmethyl, triazolylmethyl, pyrazolylmethyl, pyridylmethyl, pyrazinylmethyl, pyridazinylmethyl and pyrimidinylmethyl.

In certain embodiments, L is C=O, Q is absent or O, and $R^6$ is carbocyclylM-, wherein M is $C_{0-1}$alkyl. In certain such embodiments, $R^6$ is cyclopropyl or cyclohexyl.

In certain embodiments, L and A are C=O, Q is absent, Z is O, M is $C_{1-8}$alkyl, preferably methylene, and $R^6$ is selected from $R^{11}$ZA-$C_{1-8}$alkyl-, $R^{14}$Z—$C_{1-8}$alkyl-, $R^{11}$ZA—$C_{1-8}$alkyl-ZAZ—$C_{1-8}$alkyl-, $(R^{11}O)(R^{12}O)P(=O)O$—$C_{1-8}$alkyl-ZAZ—$C_{1-8}$alkyl-, $(R^{11}O)(R^{12}O)P(=O)O$—$C_{1-8}$alkyl-Z—$C_{1-8}$alkyl-, and heterocyclylMZAZ—$C_{1-8}$alkyl-, wherein each occurrence of A is independently other than a covalent bond. In certain such embodiments, $R^6$ is heterocyclylMZAZ—$C_{1-8}$alkyl- where heterocyclyl is substituted or unsubstituted oxodioxolenyl or $N(R^{16})(R^{17})$, wherein $R^{16}$ and $R^{17}$ together are $C_{1-16}$alkyl-Y—$C_{1-6}$alkyl, preferably $C_{1-3}$alkyl-Y—$C_{1-3}$alkyl, thereby forming a ring.

In certain preferred embodiments, L is C=O, Q is absent, M is $C_{1-8}$alkyl, and $R^6$ is selected from $(R^{11}O)(R^{12}O)P(=O)$ O—$C_{1-8}$alkyl-, $(R^{13})_2NC_{1-8}$alkyl, $(R^{13})_3N^+C_{1-8}$alkyl-, and heterocyclyl-M-. In certain such embodiments, $R^6$ is $(R^{13})_2$ $NC_{1-8}$alkyl or $(R^{13})_3N^+C_{1-8}$alkyl-, where $R^{13}$ is $C_{1-6}$alkyl. In certain other such embodiments, $R^6$ is heterocyclylM-, where heterocyclyl is selected from morpholino, piperidino, piperazino, and pyrrolidino.

In certain embodiments, L is C=O, $R^5$ is $C_{1-6}$alkyl, Q is selected from O and NH and $R^6$ is selected from $C_{1-6}$alkyl, cycloalkyl-M, $C_{1-6}$aralkyl, and $C_{1-6}$heteroaralkyl. In other embodiments, L is C=O, $R^5$ is $C_{1-6}$alkyl, Q is selected from O and NH, and $R^6$ is $C_{1-6}$alkyl, where $C_{1-6}$alkyl is selected from methyl, ethyl, and isopropyl. In further embodiments, L is C=O, $R^5$ is $C_{1-6}$alkyl, Q is selected from O and NH and $R^6$ is $C_{1-6}$aralkyl, where aralkyl is phenylmethyl. In other embodiments, L is C=O, $R^5$ is $C_{1-6}$alkyl, Q is selected from O and NH, and $R^6$ is $C_{1-6}$heteroaralkyl, where heteroaralkyl is (4-pyridyl)methyl.

In certain embodiments, L is absent or is C=O, and $R^5$ and $R^6$ together are $C_{1-6}$alkyl-Y—$C_{1-6}$alkyl, $C_{1-6}$alkyl-ZA-$C_{1-6}$alkyl, or $C_{1-6}$alkyl-A, wherein each occurrence of Z and A is independently other than a covalent bond, thereby forming a ring. In certain preferred embodiments, L is C=O, Q and Y are absent, and $R^5$ and $R^6$ together are $C_{1-3}$alkyl-Y—$C_{1-3}$alkyl. In another preferred embodiment, L and Q are absent, and $R^5$ and $R^6$ together are $C_{1-3}$alkyl-Y—$C_{1-3}$alkyl. In another preferred embodiment, L is C=O, Q is absent, Y is selected from NH and N—$C_{1-6}$alkyl, and $R^5$ and $R^6$ together are $C_{1-3}$alkyl-Y—$C_{1-3}$alkyl. In another preferred embodiment, L is C=O, Y is absent, and $R^5$ and $R^6$ together are $C_{1-3}$alkyl-Y—$C_{1-3}$alkyl. In another preferred embodiment, L and A are C=O, and $R^5$ and $R^6$ together are $C_{1-2}$alkyl-ZA-$C_{1-2}$alkyl. In another preferred embodiment, L and A are C=O and $R^5$ and $R^6$ together are $C_{2-3}$alkyl-A.

In certain embodiments, $R^7$ and $R^8$ are independently selected from hydrogen and $C_{1-6}$alkyl. In certain preferred such embodiments, $R^7$ and $R^8$ are independently selected from hydrogen and methyl. In more preferred such embodiments, $R^7$ and $R^8$ are both hydrogen.

In certain embodiments, X is O, $R^2$ and $R^3$ are each independently $C_{1-6}$aralkyl, and $R^1$ is selected from $C_{1-6}$alkyl, $C_{1-6}$hydroxyalkyl, $C_{1-6}$alkoxyalkyl, aryl, and $C_{1-6}$aralkyl, any of which is optionally substituted with one or more of amide, amine, carboxylic acid (or a salt thereof), ester (including $C_{1-6}$alkyl ester, $C_{1-5}$alkyl ester, and aryl ester), thiol, or thioether substituents.

In certain embodiments, the stereochemical configuration of the carbons bearing $R^1$, $R^2$, or $R^3$ are independently D or L. In certain preferred embodiments, the stereochemical configuration of at least one of the carbons bearing $R^1$, $R^2$, and $R^3$ respectively is D. In certain preferred such embodiments, the stereochemical configuration of the carbon bearing $R^1$ is D. In certain such embodiments, the stereochemical configuration of the carbon bearing $R^2$ is D. In certain such embodiments, the stereochemical configuration of the carbon bearing $R^3$ is D. In certain embodiments the stereochemical configuration of at least two of the carbons bearing $R^1$, $R^2$, and $R^3$ respectively is D. In yet another preferred embodiment, the stereochemical configuration of all three of the carbons bearing $R^1$, $R^2$, and $R^3$ respectively is D.

Another aspect of the invention relates to compounds having a structure of formula (IV) or a pharmaceutically acceptable salt thereof,

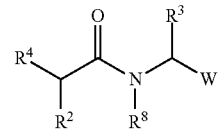

(IV)

wherein each A is independently selected from C=O, C=S, and $SO_2$, preferably C=O; or A is optionally a covalent bond when adjacent to an occurrence of Z;

L is absent or is selected from C=O, C=S, and $SO_2$, preferably $SO_2$ or C=O;

M is absent or is $C_{1-12}$alkyl, preferably $C_{1-8}$alkyl;

W is selected from —CHO and —$B(OR^{11})_2$;

Q is absent or is selected from O, NH, and N—$C_{1-6}$alkyl;

Y is absent or is selected from C=O and $SO_2$;

each Z is independently selected from O, S, NH, and N—$C_{1-6}$alkyl, preferably O; or Z is optionally a covalent bond when adjacent to an occurrence of A;

$R^2$ and $R^3$ are each independently selected from aryl, $C_{1-6}$aralkyl, heteroaryl, and $C_{1-6}$heteroaralkyl;

$R^4$ is $N(R^5)L-Q-R^6$;

$R^5$ is selected from hydrogen, OH, $C_{1-6}$aralkyl, and $C_{1-6}$alkyl, preferably hydrogen;

$R^6$ is selected from hydrogen, $C_{1-6}$alkyl, $C_{1-6}$alkenyl, $C_{1-6}$alkynyl, Ar—Y—, carbocyclyl, heterocyclyl, an N-terminal protecting group, aryl, $C_{1-6}$aralkyl, heteroaryl, $C_{1-6}$heteroaralkyl, $R^{11}ZAZ$—$C_{1-8}$alkyl-, $R^{14}Z$—$C_{1-8}$alkyl-, $(R^{11}O)(R^{12}O)P(=O)O$—$C_{1-8}$alkyl-ZAZ—$C_{1-8}$alkyl-, $R^{11}ZAZ$—$C_{1-8}$alkyl-ZAZ—$C_{1-8}$alkyl-, heterocyclylMZAZ—$C_{1-8}$alkyl-, $(R^{11}O)(R^{12}O)P(=O)O$—$C_{1-8}$alkyl-, $(R^{13})_2N$—$C_{1-12}$alkyl-, $(R^{13})_3N^+$—$C_{1-12}$alkyl-, heterocyclylM-, carbocyclylM-, $R^{14}SO_2C_{1-8}$alkyl-, and $R^{14}SO_2NH$; preferably an N-capping group, more preferably t-butoxycarbonyl or benzyloxycarbonyl; or $R^5$ and $R^6$ together are $C_{1-6}$alkyl-Y—$C_{1-6}$alkyl, $C_{1-6}$alkyl-ZAZ—$C_{1-6}$alkyl, ZAZ—$C_{1-6}$alkyl-ZAZ—$C_{1-6}$alkyl, ZAZ—$C_{1-6}$alkyl-ZAZ, or $C_{1-6}$alkyl-A, thereby forming a ring;

$R^8$ is selected from hydrogen, $C_{1-6}$alkyl, and $C_{1-6}$aralkyl, preferably hydrogen;

$R^9$ is selected from hydrogen, OH, and $C_{1-6}$alkyl, preferably $C_{1-6}$alkyl; and $R^{10}$ is an N-terminal protecting group;

$R^{11}$ and $R^{12}$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^{11}$ and $R^{12}$ together are $C_{1-6}$alkyl, thereby forming a ring;

each $R^{13}$ is independently selected from hydrogen and $C_{1-6}$alkyl, preferably $C_{1-6}$alkyl; and $R^{14}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

each $R^{16}$ is independently selected from hydrogen and $C_{1-6}$alkyl; or two occurrences of $R^{11}$ together may be $C_{1-6}$alkyl, thereby forming a ring together with the intervening boron and oxygen atoms to which they are attached;

provided that in any occurrence of the sequence ZAZ, at least one member of the sequence must be other than a covalent bond.

In certain embodiments, $R^2$ is selected from $C_{1-6}$aralkyl and $C_{1-6}$heteroaralkyl. In certain such embodiments, $R^2$ is selected from $C_{1-6}$alkyl-phenyl, $C_{1-6}$alkyl-indolyl, $C_{1-6}$alkyl-thienyl, $C_{1-6}$alkyl-thiazolyl, and $C_{1-6}$alkyl-isothiazolyl, wherein the alkyl moiety may contain six, five, four, three, two, or one carbon atoms, preferably one or two. In certain such embodiments, $R^2$ is substituted with one or more substituents selected from hydroxy, halogen, amide, amine, carboxylic acid (or a salt thereof), ester (including $C_{1-6}$alkyl ester, $C_{1-5}$alkyl ester, and aryl ester), thiol, or thioether. In certain such embodiments, $R^2$ is substituted with a substituent selected from alkyl, trihaloalkyl, alkoxy, hydroxy, or cyano. In certain such embodiments, $R^2$ is selected from $C_{1-6}$alkyl-phenyl and $C_{1-6}$alkyl-indolyl. In certain preferred such embodiments, $R^2$ is selected from

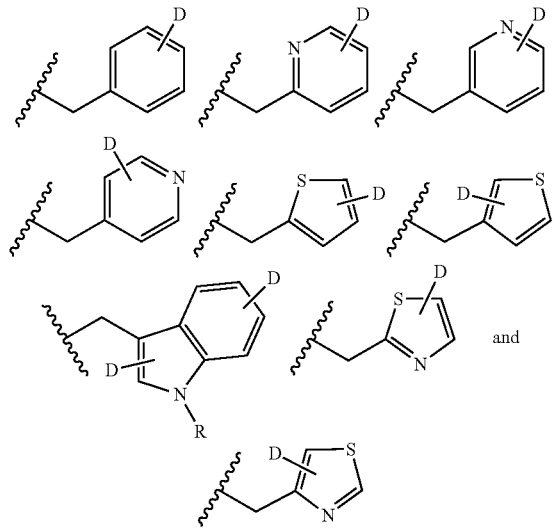

R = H or any suitable protecting group wherein D is selected from H, OMe, OBu$^t$, OH, CN, $CF_3$ and $CH_3$. In certain embodiments D is selected from H, OMe, OH, CN, $CF_3$ and $CH_3$.

In certain preferred such embodiments where D is attached to a six-membered ring, D is attached at the 4-position relative to the point of attachment, preferably excluding embodiments where the 4-position of the ring is occupied by the nitrogen of a pyridine ring.

In certain embodiments, $R^3$ is selected from $C_{1-6}$aralkyl and $C_{1-6}$heteroaralkyl. In certain the alkyl moiety may contain six, five, four, three, two, or one carbon atoms, preferably one or two. In certain such embodiments, $R^3$ is substituted with one or more substituents selected from hydroxy, halogen, amide, amine, carboxylic acid (or a salt thereof), ester (including $C_{1-6}$alkyl ester, $C_{1-5}$alkyl ester, and aryl ester), thiol, or thioether. In certain such embodiments, $R^3$ is substituted with a substituent selected from alkyl, trihaloalkyl, alkoxy, hydroxy, or cyano. In certain such embodiments, $R^3$ is selected from $C_{1-6}$alkyl-phenyl and $C_{1-6}$alkyl-indolyl. In certain preferred such embodiments, $R^3$ is selected from

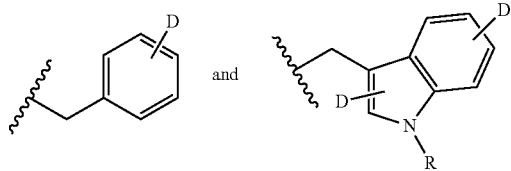

R = H, any suitable protecting group wherein D is selected from H, OMe, OBu$^t$, OH, CN, $CF_3$ or $CH_3$. In certain embodiments, D is selected from H, OMe, OH, CN, $CF_3$ or $CH_3$.

In certain embodiments, $R^5$ is hydrogen, L is C=O or $SO_2$, $R^6$ is Ar—Y—, and each Ar is independently selected from phenyl, indolyl, benzofuranyl, naphthyl, quinolinyl, quinolonyl, thienyl, pyridyl, pyrazyl, and the like. In certain such embodiments, Ar may be substituted with Ar-E-, where E is selected from a direct bond, —O—, and $C_{1-6}$alkyl. In certain other such embodiments where Q is $C_{1-6}$alkyl, Q may be substituted, preferably with Ar, e.g., phenyl.

In certain embodiments, $R^5$ is hydrogen, Q is absent, L is C=O or $SO_2$, and $R^6$ is selected from Ar—Y and heterocyclyl. In certain preferred such embodiments, heterocyclyl is selected from chromonyl, chromanyl, morpholino, and piperidinyl. In certain other preferred such embodiments, Ar is selected from phenyl, indolyl, benzofuranyl, naphthyl, quinolinyl, quinolonyl, thienyl, pyridyl, pyrazyl, and the like.

In certain embodiments, $R^5$ is hydrogen, L is C=O or $SO_2$, Q is absent, and $R^6$ is $C_{1-6}$alkenyl, where $C_{1-6}$alkenyl is a substituted vinyl group where the substituent is preferably an aryl or heteroaryl group, more preferably a phenyl group optionally substituted with one to four substituents.

In certain embodiments, L and Q are absent and $R^6$ is selected from $C_{1-6}$alkyl, $C_{1-6}$alkenyl, $C_{1-6}$alkynyl, $C_{1-6}$aralkyl, and $C_{1-6}$heteroaralkyl. In certain such embodiments, $R^5$ is $C_{1-6}$alkyl and $R^6$ is selected from butyl, allyl, propargyl, phenylmethyl, 2-pyridyl, 3-pyridyl, and 4-pyridyl.

In other embodiments, L is $SO_2$, Q is absent, and $R^6$ is selected from $C_{1-6}$alkyl and aryl. In certain such embodiments, $R^6$ is selected from methyl and phenyl.

In certain embodiments, L is C=O and $R^6$ is selected from $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^{11}$ZA-$C_{1-8}$alkyl-, $R^{14}$Z—$C_{1-8}$alkyl-, $(R^{11}O)(R^{12}O)P(=O)O$—$C_{1-8}$alkyl-, $(R^{11}O)(R^{12}O)P(=O)O$—$C_{1-8}$alkyl-ZAZ—$C_{1-8}$alkyl-, $(R^{11}O)(R^{12}O)P(=O)O$—$C_{1-8}$alkyl-Z—$C_{1-8}$alkyl-, $R^{11}$ZA-$C_{1-8}$alkyl-ZAZ—$C_{1-8}$alkyl-, heterocyclylMZAZ—$C_{1-8}$alkyl-, $(R^{13})_2$N—$C_{1-8}$alkyl-, $(R^{13})_3$N$^+$—$C_{1-8}$alkyl-, heterocyclylM-, carbocyclylM-, $R^{14}SO_2C_{1-8}$alkyl-, and $R^{14}SO_2NH$—, wherein each occurrence of Z and A is independently other than a covalent bond. In certain embodiments, L is C=O, Q is absent, and $R^6$ is H.

In certain embodiments, $R^5$ is $C_{1-6}$alkyl, $R^6$ is $C_{1-6}$alkyl, Q is absent, and L is C=O. In certain such embodiments, $R^6$ is ethyl, isopropyl, 2,2,2-trifluoroethyl, or 2-(methylsulfonyl)ethyl.

In other embodiments, L is C=O, Q is absent, and $R^6$ is $C_{1-6}$aralkyl. In certain such embodiments, $R^6$ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, $R^5$ is $C_{1-6}$alkyl, and $R^6$ is aryl. In certain such embodiments, $R^6$ is substituted or unsubstituted phenyl.

In certain embodiments, L is C=O, Q is absent, and $R^6$ is selected from heteroaryl and $C_{1-6}$heteroaralkyl. In certain such embodiments, $R^6$ is heteroaryl selected from pyrrole, furan, thiophene, imidazole, isoxazole, oxazole, oxadiazole, thiazole, thiadiazole, triazole, pyrazole, pyridine, pyrazine, pyridazine and pyrimidine. In certain alternative such embodiments, $R^6$ is $C_{1-6}$heteroaralkyl selected from pyrrolylmethyl, furanylmethyl, thienylmethyl, imidazolylmethyl, isoxazolylmethyl, oxazolylmethyl, oxadiazolylmethyl, thiazolylmethyl, thiadiazolylmethyl, triazolylmethyl, pyrazolylmethyl, pyridylmethyl, pyrazinylmethyl, pyridazinylmethyl and pyrimidinylmethyl.

In certain embodiments, L is C=O, Q is absent or O, and $R^6$ is carbocyclylM-, wherein M is $C_{0-1}$alkyl. In certain such embodiments, $R^6$ is cyclopropyl or cyclohexyl.

In certain embodiments, L and A are C=O, Q is absent, Z is O, M is $C_{1-8}$alkyl, preferably methylene, and $R^6$ is selected from $R^{11}ZA-C_{1-8}$alkyl-, $R^{14}Z-C_{1-8}$alkyl-, $R^{11}ZA-C_{1-8}$alkyl-ZAZ—$C_{1-8}$alkyl-, $(R^{11}O)(R^{12}O)P(=O)O-C_{1-8}$alkyl-ZAZ—$C_{1-8}$alkyl-, $(R^{11}O)(R^{12}O)P(=O)O-C_{1-8}$alkyl-Z—$C_{1-8}$alkyl-, and heterocyclylMZAZ—$C_{1-8}$alkyl-, wherein each occurrence of A is independently other than a covalent bond. In certain such embodiments, $R^6$ is heterocyclylMZAZ—$C_{1-8}$alkyl- where heterocyclyl is substituted or unsubstituted oxodioxolenyl or $N(R^{16})(R^{17})$, wherein $R^{16}$ and $R^{17}$ together are $C_{1-6}$alkyl-Y—$C_{1-6}$alkyl, preferably $C_{1-3}$alkyl-Y—$C_{1-3}$alkyl, thereby forming a ring.

In certain preferred embodiments, L is C=O, Q is absent, M is $C_{1-8}$alkyl, and $R^6$ is selected from $(R^{11}O)(R^{12}O)P(=O)O-C_{1-8}$alkyl-, $(R^{13})_2NC_{1-8}$alkyl, $(R^{13})_3N^+C_{1-8}$alkyl-, and heterocyclyl-M-. In certain such embodiments, $R^6$ is $(R^{13})_2NC_{1-8}$alkyl or $(R^{13})_3N^+C_{1-8}$alkyl-, where $R^{13}$ is $C_{1-6}$alkyl. In certain other such embodiments, $R^6$ is heterocyclylM-, where heterocyclyl is selected from morpholino, piperidino, piperazino, and pyrrolidino.

In certain embodiments, L is C=O, $R^5$ is $C_{1-6}$alkyl, Q is selected from O and NH and $R^6$ is selected from $C_{1-6}$alkyl, cycloalkyl-M, $C_{1-6}$aralkyl, and $C_{1-6}$heteroaralkyl. In other embodiments, L is C=O, $R^5$ is $C_{1-6}$alkyl, Q is selected from O and NH, and $R^6$ is $C_{1-6}$alkyl, where $C_{1-6}$alkyl is selected from methyl, ethyl, and isopropyl. In further embodiments, L is C=O, $R^5$ is $C_{1-6}$alkyl, Q is selected from O and NH and $R^6$ is $C_{1-6}$aralkyl, where aralkyl is phenylmethyl. In other embodiments, L is C=O, $R^5$ is $C_{1-6}$alkyl, Q is selected from O and NH, and $R^6$ is $C_{1-6}$heteroaralkyl, where heteroaralkyl is (4-pyridyl)methyl.

In certain embodiments, L is absent or is C=O, and $R^5$ and $R^6$ together are $C_{1-6}$alkyl-Y—$C_{1-6}$alkyl, $C_{1-6}$alkyl-ZA-$C_{1-6}$alkyl, or $C_{1-6}$alkyl-A, wherein each occurrence of Z and A is independently other than a covalent bond, thereby forming a ring. In certain preferred embodiments, L is C=O, Q and Y are absent, and $R^5$ and $R^6$ together are $C_{1-3}$alkyl-Y—$C_{1-3}$alkyl. In another preferred embodiment, L and Q are absent, and $R^5$ and $R^6$ together are $C_{1-3}$alkyl-Y—$C_{1-3}$alkyl. In another preferred embodiment, L is C=O, Q is absent, Y is selected from NH and N—$C_{1-6}$alkyl, and $R^5$ and $R^6$ together are $C_{1-3}$alkyl-Y—$C_{1-3}$alkyl. In another preferred embodiment, L is C=O, Y is absent, and $R^5$ and $R^6$ together are $C_{1-3}$alkyl-Y—$C_{1-3}$alkyl. In another preferred embodiment, L and A are C=O, and $R^5$ and $R^6$ together are $C_{1-2}$alkyl-ZA-$C_{1-2}$alkyl. In another preferred embodiment, L and A are C=O and $R^5$ and $R^6$ together are $C_{2-3}$alkyl-A.

In certain embodiments, $R^8$ is selected from hydrogen and $C_{1-6}$alkyl. In certain preferred such embodiments, $R^8$ is selected from hydrogen and methyl. In more preferred such embodiments, $R^8$ is hydrogen.

In certain embodiments, X is O, $R^2$ and $R^3$ are each independently $C_{1-6}$aralkyl, and $R^1$ is selected from $C_{1-6}$alkyl, $C_{1-6}$hydroxyalkyl, $C_{1-6}$alkoxyalkyl, aryl, and $C_{1-6}$aralkyl, any of which is optionally substituted with one or more of amide, amine, carboxylic acid (or a salt thereof), ester (including $C_{1-6}$alkyl ester, $C_{1-5}$alkyl ester, and aryl ester), thiol, or thioether substituents.

In certain embodiments, the stereochemical configuration of the carbons bearing $R^2$ or $R^3$ are independently D or L. In certain preferred embodiments, the stereochemical configuration of at least one of the carbons bearing $R^2$ and $R^3$ respectively is D. In certain such embodiments, the stereochemical configuration of the carbon bearing $R^2$ is D. In such embodiments, the stereochemical configuration of the carbon bearing $R^3$ is D. In certain embodiments, the stereochemical configuration of both of the carbons bearing $R^2$ and $R^3$ respectively is D.

One aspect of the invention relates to inhibitors that preferentially inhibit immunoproteasome activity over constitutive proteasome activity. In certain embodiments, the $EC_{50}$ ratio of a compound of any one of formulae I to IV in an assay of constitutive proteasome activity as compared to the $EC_{50}$ of the same compound in an assay of immunoproteasome activity is greater than 1. In certain such embodiments, the $EC_{50}$ is greater than 2, 3, 4 or even 5. Suitable assays for the determination of the constitutive proteasome activity and the immunoproteasome activity are described herein (see Example 18).

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1-6}$alkoxyalkyl" refers to a $C_{1-6}$alkyl group substituted with an alkoxy group, thereby forming an ether.

The term "$C_{1-6}$aralkyl", as used herein, refers to a $C_{1-6}$alkyl group substituted with an aryl group.

The terms "amine" and "amino" are art-recognized and refer to both unsubstituted and substituted amines and salts thereof, e.g., a moiety that can be represented by the general formulae:

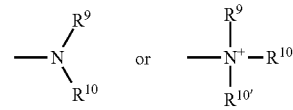

wherein $R^9$, $R^{10}$ and $R^{10'}$ each independently represent a hydrogen, an alkyl, an alkenyl, —$(CH_2)_m$—$R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In preferred embodiments, only one of $R^9$ or $R^{10}$ can be a carbonyl, e.g., $R^9$, $R^{10}$, and the nitrogen together do not form an imide. In even more preferred embodiments, $R^9$ and $R^{10}$ (and optionally $R^{10'}$) each independently represent a hydrogen, an alkyl, an alkenyl, or —$(CH_2)_m$—$R^8$. In certain embodiments, an amino group is basic, meaning it has a $pK_a$>7.00. The protonated forms of these functional groups have $pK_a$s above 7.00.

The terms "amide" and "amido" are art-recognized as an amino-substituted carbonyl and includes a moiety that can be represented by the general formula:

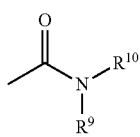

wherein $R^9$, $R^{10}$ are as defined above. Preferred embodiments of the amide will not include imides which may be unstable.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls.

The term "carbonyl" is art-recognized and includes such moieties as can be represented by the general formula:

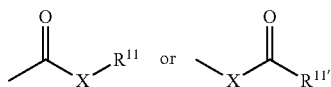

wherein X is a bond or represents an oxygen or a sulfur, and $R^{11}$ represents a hydrogen, an alkyl, an alkenyl, —$(CH_2)_m$—$R^8$ or a pharmaceutically acceptable salt, $R^{11'}$ represents a hydrogen, an alkyl, an alkenyl or —$(CH_2)_m$—$R^8$, where m and $R^8$ are as defined above. Where X is an oxygen and $R^{11}$ or $R^{11'}$ is not hydrogen, the formula represents an "ester". Where X is an oxygen, and $R^{11}$ is a hydrogen, the formula represents a "carboxylic acid".

As used herein, "enzyme" can be any partially or wholly proteinaceous molecule which carries out a chemical reaction in a catalytic manner. Such enzymes can be native enzymes, fusion enzymes, proenzymes, apoenzymes, denatured enzymes, farnesylated enzymes, ubiquitinated enzymes, fatty acylated enzymes, gerangeranylated enzymes, GPI-linked enzymes, lipid-linked enzymes, prenylated enzymes, naturally-occurring or artificially-generated mutant enzymes, enzymes with side chain or backbone modifications, enzymes having leader sequences, and enzymes complexed with non-proteinaceous material, such as proteoglycans, proteoliposomes. Enzymes can be made by any means, including natural expression, promoted expression, cloning, various solution-based and solid-based peptide syntheses, and similar methods known to those of skill in the art.

The term "C1-6heteroaralkyl", as used herein, refers to a C1-6alkyl group substituted with a heteroaryl group.

The terms "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, isoxazole, oxazole, oxadiazole, thiazole, thiadiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, phosphorus, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms. The term terms "heterocyclyl" or "heterocyclic group" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, tetrahydropyran, piperidine, piperazine, pyrrolidine, morpholine, lactones, lactams, and the like.

The term "$C_{1-6}$hydroxyalkyl" refers to a $C_{1-6}$alkyl group substituted with a hydroxy group.

As used herein, the term "inhibitor" is meant to describe a compound that blocks or reduces an activity of an enzyme (for example, inhibition of proteolytic cleavage of standard fluorogenic peptide substrates such as suc-LLVY-AMC, Box-LLR-AMC and Z-LLE-AMC, inhibition of various catalytic activities of the 20S proteasome). An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme.

As used herein, the term "peptide" includes not only standard amide linkage with standard α-substituents, but commonly utilized peptidomimetics, other modified linkages, non-naturally occurring side chains, and side chain modifications, as detailed below.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prodrug" encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "thioether" refers to an alkyl group, as defined above, having a sulfur moiety attached thereto. In preferred embodiments, the "thioether" is represented by —S-alkyl. Representative thioether groups include methylthio, ethylthio, and the like.

As used herein, the term "treating" or "treatment" includes reversing, reducing, or arresting the symptoms, clinical signs, and underlying pathology of a condition in manner to improve or stabilize a subject's condition.

Uses of Enzyme Inhibitors

The biological consequences of proteasome inhibition are numerous. Proteasome inhibition has been suggested as a prevention and/or treatment of a multitude of diseases including, but not limited to, proliferative diseases, neurotoxic/degenerative diseases, ischemic conditions, inflammation, immune-related diseases, HIV, cancers, organ graft rejection, septic shock, viral and parasitic infections, conditions associated with acidosis, macular degeneration, pulmonary conditions, muscle wasting diseases, fibrotic diseases, bone and hair growth diseases.

Proteasome inhibitors can be used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation).

At the cellular level, the accumulation of polyubiquitinated proteins, cell morphological changes, and apoptosis have been reported upon treatment of cells with various proteasome inhibitors. Yet, it should be noted that commercially available proteasome inhibitors inhibit both the constitutive and immuno-forms of the proteasome. Even bortezomib, the only FDA-approved proteasome inhibitor for the treatment of relapsed multiple myeloma patients, does not distinguish between the two forms (Altun et al, Cancer Res 65:7896, 2005). Thus, what is known about therapeutic proteasome inhibition is based on work with molecules that inhibit both forms of the proteasome. Accordingly, compounds of the invention may be beneficial for reducing the severity of side effects associated with molecules that inhibit both forms of the proteasome.

Immunoproteasome expression occurs predominantly in cells and organs that make up the lymphatic system, such as white blood cells (leukocytes), bone marrow, and the thymus, spleen and lymph nodes. Although some organs preferentially express constitutive proteasomes (e.g., heart), others such as adrenal, liver, lung and gut, appear to express both forms.

The immune system, of which leukocytes and lymphoid tissues play a major role, is responsible for protecting an organism from outside biological influences. When functioning properly, it protects the body against bacterial and viral infections. The immune system also screens for autologous cells that have undergone oncogenic transformation. Intracellular proteolysis generates small peptides for presentation to T-lymphocytes to induce MHC class I-mediated immune responses. The proteasome is the main provider of these precursor peptides, however, differences between antigenic peptides have been observed between cells with varying amounts of each proteasome form (Cascio et al, EMBO J. 20:2357-2366, 2001). In certain embodiments, the invention relates to a method for inhibiting antigen presentation in a cell, including exposing the cell to a compound described herein. In certain embodiments, the invention relates to a method for altering the repertoire of antigenic peptides produced by the proteasome or other Ntn with multicatalytic activity. For example, if the activity of the immunoproteasome proteasome is selectively inhibited, a different set of antigenic peptides may be produced by the remaining constitutive proteasome and presented in MHC molecules on the surfaces of cells than would be produced and presented without any enzyme inhibition.

Several disorders and disease states have been associated with aberrant immune system function, herein referred to as immune-related conditions. Perhaps the most common immune-related condition is the allergic disorders such as allergies, asthma and atopic dermatitis like eczema. These occur when the immune system overreacts to exposure to antigens in the environment. Thus, a further embodiment is a method for suppressing the immune system of a subject including administering to the subject an effective amount of a proteasome inhibitor compound in a manner described herein.

Immunodeficiency disorders occur when a part of the immune system is not working properly or is not present. They can affect B lymphyctes, T lymphocytes, or phagocytes and be either inherited (e.g., IgA deficiency, severe combined immunodeficiency (SCID), thymic dysplasia and chronic granulomatous) or acquired (e.g., acquired immunodeficiency syndrome (AIDS), human immunodeficiency virus (HIV) and drug-induced immunodeficiencies). A dosing strategy utilizing selective proteasome inhibitors of the invention may be used to treat immune-related conditions such as immunodeficiency disorders.

In autoimmune disorders, the immune system inappropriately attacks the body's healthy organs and tissues as if they were foreign invaders. An example of an autoimmune disease is Sjogren's Syndrome, which is characterized by infiltration and focal accumulation of lymphocytes in the exocrine glands. A study examining the proteasome expression level revealed a significant up-regulation of beta5i (LMP7) exclusively in the salivary glands of SS patients (Egerer et al, Arthritis Rheum 54:1501-8, 2006). Other examples of such immune-related conditions include lupus, rheumatoid arthritis, scleroderma, ankylosing spondylitis, dermatomyositis, psoriasis, multiple sclerosis and inflammatory bowel disease (such as ulcerative colitis and Crohn's disease). Tissue/organ transplant rejection occurs when the immune system mistakenly attacks the cells being introduced to the host's body. Graft versus host disease (GVHD), resulting from allogenic transplantation, arises when the T cells from the donor tissue go on the offensive and attack the host's tissues. In all three circumstances, autoimmune disease, transplant rejection and GVHD, modulating the immune system by treating the subject with a composition of the invention could be beneficial.

Inflammation is the first response of the immune system to infection or irritation. A cellular component of inflammation involves the movement of leukocytes, which express immunoproteasome, from blood vessels into the inflamed tissue. These cells take on the important role of removing the irritant, bacteria, parasite or cell debris. Proteasome inhibitors are already known to have anti-inflammatory activity (Meng et al, PNAS 96:10403-10408, 1999). In cases of chronic inflammation, which is characterized by a dominating presence of macrophages, the cells that originally served as defensive agents begin to release toxins and cytokines, including TNF-α, now become injurious to the body, resulting in tissue damage and loss. In certain embodiments, the invention relates to a method of treating inflammation and inflammatory diseases comprising administering to the subject in need of such treatment an effective amount of a proteasome inhibitor compound described herein. Inflammatory diseases include acute (e.g., bronchitis, conjunctivitis, pancreatitis) and chronic conditions (e.g., chronic cholecstitis, bronchiectasis, aortic valve stenosis, restenosis, psoriasis and arthritis), along with conditions associated with inflammation such as fibrosis, infection and ischemia.

Following tissue damage, including damage due to the inflammation process, progression of regeneration and repair begins. During the regeneration step, lost tissue is replaced by proliferation of cells of the same type, which reconstruct the normal architecture. However, improper regeneration of the tissue architecture may have severe consequences. In some cases of chronic inflammatory liver disease, the regenerated tissue forms an abnormal nodular architecture leading to cirrhosis and portal hypertension. The repair process is where lost tissue is replaced by a fibrous scar which is produced from granulation tissue. Fibrosis is the excessive and persistent formation of scar tissue resulting from the hyperproliferative growth of fibroblasts and is associated with activation of the TGF-β signaling pathway. Fibrosis involves extensive deposition of extracellular matrix and can occur within virtually any tissue or across several different tissues. Normally, the level of intracellular signaling protein (Smad) that activate transcription of target genes upon TGF-β stimulation is regulated by proteasome activity (Xu et al., 2000). However, accelerated degradation of the TGF-β signaling components has been observed in cancers and other hyperproliferative conditions. Thus, certain embodiments of the invention relate to a method for treating hyperproliferative conditions such as diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases and extrinsic lung disorders). The treatment of burn victims is often hampered by fibrosis, thus, in certain embodiments, the invention relates to the topical or systemic administration of inhibitors to treat burns. Wound closure following surgery is often associated with disfiguring scars, which may be prevented by inhibition of fibrosis. Thus, in certain embodiments, the invention relates to a method for the prevention or reduction of scarring.

Infection by bacteria, parasite or virus all result in initiating the inflammatory process. When the resulting inflammation overwhelms the whole organism, systemic inflammatory response syndrome (SIRS) occurs. The term sepsis is applied when this is due to infection. Overproduction of lipopolysaccharide (LPS)-induced cytokines such as TNFα is considered to be central to the processes associated with septic shock. Not surprisingly, LPS also induces an increase in all components of the MHC-1 pathway including the immunoproteasome subunits LMP2 and LMP7 (MacAry et al, PNAS 98:3982-3987, 2001). Furthermore, it is generally accepted that the first step in the activation of cells by LPS is the binding of LPS to specific membrane receptors. The α- and β-subunits of the 20S proteasome complex have been identified as LPS-binding proteins, suggesting that the LPS-induced signal transduction may be an important therapeutic target in the treatment or prevention of sepsis (Qureshi, N. et al., J. Immun. (2003) 171: 1515-1525). Therefore, in certain embodiments, the proteasome inhibitors disclosed herein may be used for the inhibition of TNFα to prevent and/or treat septic shock.

In another embodiment, the disclosed compositions are useful for the treatment of a parasitic infection, such as infections caused by protozoan parasites. The proteasome of these parasites is considered to be involved primarily in cell differentiation and replication activities (Paugam et al., Trends Parasitol. 2003, 19(2): 55-59). Furthermore, *entamoeba* species have been shown to lose encystation capacity when exposed to proteasome inhibitors (Gonzales, et al., Arch. Med. Res. 1997, 28, Spec No: 139-140). In certain such embodiments, the proteasome inhibitor compositions herein are useful for the treatment of parasitic infections in humans caused by a protozoan parasite selected from *Plasmodium* sps. (including *P. falciparum, P. vivax, P. malariae,* and *P. ovale*, which cause malaria), *Trypanosoma* sps. (including *T. cruzi*, which causes Chagas' disease, and *T. brucei* which causes African sleeping sickness), *Leishmania* sps. (including *L. amazonesis, L. donovani, L. infantum, L. mexicana,* etc.), *Pneumocystis carinii* (a protozoan known to cause pneumonia in AIDS and other immunosuppressed patients), *Toxoplasma gondii, Entamoeba histolytica, Entamoeba invadens*, and *Giardia lamblia*. In certain embodiments, the disclosed compositions are useful for the treatment of parasitic infections in animals and livestock caused by a protozoan parasite selected from *Plasmodium hermani, Cryptosporidium* sps., *Echinococcus granulosus, Eimeria tenella, Sarcocystis neurona,* and *Neurospora crassa*. Other compounds useful as proteasome inhibitors in the treatment of parasitic diseases are described in WO 98/10779, which is incorporated herein in its entirety.

In certain embodiments, the proteasome inhibitor compositions inhibit proteasome activity in a parasite without recovery in white blood cells. In certain such embodiments, the long half-life of blood cells may provide prolonged protection with regard to therapy against recurring exposures to parasites. In certain embodiments, the proteasome inhibitors described herein may provide prolonged protection with regard to chemoprophylaxis against future infection.

Viral infections contribute to the pathology of many diseases. Heart conditions such as ongoing myocarditis and dilated cardiomyopathy have been linked to the coxsackievirus B3. In a comparative whole-genome microarray analyses of infected mouse hearts, all three immunoproteasome subunits were uniformly up-regulated in hearts of mice which developed chronic myocarditis (Szalay et al, Am J Pathol 168:1542-52, 2006). Some viruses utilize the ubiquitin-proteasome system in the viral entry step where the virus is released from the endosome into the cytosol. The mouse hepatitis virus (MHV) belongs to the Coronaviridae family, which also includes the severe acute respiratory syndrome (SARS) coronvirus. Yu and Lai (J Virol 79:644-648, 2005) demonstrated that treatment of cells infected with MHV with a proteasome inhibitor resulted in a decrease in viral replication, correlating with reduced viral titer as compared to that of untreated cells. The human hepatitis B virus (HBV), a member of the Hepadnaviridae virus family, requires virally encoded envelop proteins to propagate Inhibiting the proteasome degradation pathway causes a significant reduction in the amount of secreted envelope proteins (Simsek et al, J Virol 79:12914-12920, 2005). In addition to HBV, other hepatitis viruses (A, C, D and E) may also utilize the ubiquitin-proteasome degradation pathway for secretion, morphogenesis and pathogenesis.

The bacterium *Listeria monocytogenes* causes a condition known as listeriosis, the manifestations of which range from mild (nausea, vomiting and diarrhea) to severe (septicemia, meningitis, encephalitis). A quantitative analysis of changes in proteasome subunit composition revealed that infection of mice with lymphocytic choriomeningitis virus or *Listeria monocytogenes* lead to an almost complete replacement of constitutive proteasomes by immunoproteasomes in the liver within seven days (Khan et al, J Immunol 167:6859-6868, 2001). Prokaryotes have what is equivalent to the eukaryote 20S proteasome particle. While the subunit composition of the prokaryote 20S particle is simpler than that of eukaryotes, it does have the ability to hydrolyze peptide bonds in a similar manner. For example, the nucleophilic attack on the peptide bond occurs through the threonine residue on the N-terminus of the β-subunits. Thus, an embodiment of this invention relates to a method of treating prokaryotic infections, comprising administering to a subject an effective amount of a proteasome inhibitor composition disclosed herein. Prokaryotic infections may include diseases caused by either mycobacteria (such as tuberculosis, leprosy or Buruli Ulcer) or archaebacteria.

Accordingly, in certain embodiments, the invention relates to a method for treating infection (e.g., bacterial, parasitic or viral), including contacting a cell with (or administering to a subject) an effective amount of a compound disclosed herein.

Ischemia and reperfusion injury results in hypoxia, a condition in which there is a deficiency of oxygen reaching the tissues of the body. This condition causes increased degradation of IκBα, thereby resulting in the activation of NF-κB (Koong et al., 1994). Interestingly, factors which have been identified as being able to enhance immunoproteasome expression, TNF-α and lipopolysaccharide, also stimulate NF-κB activation. It has been demonstrated that the severity of injury resulting in hypoxia can be reduced with the administration of a proteasome inhibitor (Gao et al., 2000; Bao et al., 2001; Pye et al., 2003). Therefore, certain embodiments of the invention relate to a method of treating an ischemic condition or reperfusion injury comprising administering to a subject in need of such treatment an effective amount of a proteasome inhibitor compound disclosed herein. Examples of such conditions or injuries include, but are not limited to, acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

Cachexia is a syndrome characterized by wasting of skeletal muscle associated with enhanced proteolysis due to the ubiquitin-proteasome pathway. Inhibiting the proteasome reduces proteolysis, thereby reducing both muscle protein loss and the nitrogenous load on kidneys or liver (Tawa et al., JCI 100:197-203, 1997). In cachexia, elevated expression of proinflammatory cytokines, TNF-α and IFN-γ, both of which stimulate expression of immunoproteasome subunits, have been reported (Acharyya et al., JCI 114:370-378, 2004). In fact, most types of muscle atrophy exhibit elevated rates of protein degradation (Lecker et al., FASEB J 18:39-51, 2004). Muscle wasting manifests itself in several life threatening diseases, including cancer, sepsis, renal failure, AIDS, fasting, denervation atrophy, acidosis, diabetes, disuse atrophy and congestive heart failure. One embodiment of the invention relates to the treatment of cachexia and muscle-wasting diseases. Methods of the invention are useful for treating conditions such as cancer, chronic infectious diseases, fever, muscle disuse (atrophy) and denervation, nerve injury, fasting, renal failure associated with acidosis, and hepatic failure. See, e.g., Goldberg, U.S. Pat. No. 5,340,736.

Degradation of certain proteins by the proteasome effect signaling mechanisms that, in turn, effect gene transcription, cell cycle and metabolic pathways. As noted above, proteasome inhibitors block both degradation and processing of ubiquitinated NF-κB in vitro and in vivo. Proteasome inhibitors also block IκB-A degradation and NF-κB activation (Palombella, et al. Cell (1994) 78:773-785; and Traenckner, et al., EMBO J. (1994) 13:5433-5441). One embodiment of the invention is a method for inhibiting IκB-α degradation, including contacting the cell with a compound described herein.

In certain embodiments, the invention relates to methods for affecting cyclin-dependent eukaryotic cell cycles, including exposing a cell (in vitro or in vivo) to a proteasome inhibitor disclosed herein. Cyclins are proteins involved in cell cycle control. The proteasome participates in the degradation of cyclins. Examples of cyclins include mitotic cyclins, G1 cyclins, and cyclin B. Degradation of cyclins enables a cell to exit one cell cycle stage (e.g., mitosis) and enter another (e.g., division). It is believed all cyclins are associated with p34$^{cdc2}$ protein kinase or related kinases. The proteolysis targeting signal is localized to amino acids 42-RAALGNISEN-50 (destruction box). There is evidence that cyclin is converted to a form vulnerable to a ubiquitin ligase or that a cyclin-specific ligase is activated during mitosis (Ciechanover, A., Cell, (1994) 79:13-21). Inhibition of the proteasome inhibits cyclin degradation, and therefore inhibits cell proliferation, for example, in cyclin-related cancers (Kumatori et al., Proc. Natl. Acad. Sci. USA (1990) 87:7071-7075). In certain embodiments, the invention relates to a method for treating a proliferative disease in a subject (e.g., cancer, psoriasis, or restenosis), comprising administering to the subject an effective amount of a proteasome inhibitor composition in a manner disclosed herein. The invention also relates to a method for treating cyclin-related inflammation in a subject, comprising administering to a subject a therapeutically effective amount of a proteasome inhibitor composition in a manner described herein.

In maturing reticulocytes and growing fibroblasts, cells deprived of insulin or serum, the rate of proteolysis nearly doubles, suggesting a role for the proteasome in cellular metabolism. In certain embodiments, the invention relates to methods for reducing the rate of intracellular protein degradation in a cell. Each of these methods comprises contacting a cell (in vivo or in vitro, e.g., a muscle in a subject) with an effective amount of a pharmaceutical composition comprising a proteasome inhibitor disclosed herein.

Alzheimer's disease (AD) is a progressive neurodegenerative disease disorder associated with a loss of higher cognitive function. Pathological hallmarks of the disease include senile amyloid plaques, neurofibrillary tangles, dystrophic neuritis and significant neuronal loss in selected regions of the brain. Microglia, the resident macrophages in the brain, release numerous proinflammatory cytokines, including TNF-α, when activated by Aβ42, a peptide associated with neuritic and vascular amyloid plaques. This microglial-mediated inflammatory response contributes to significant neuronal loss. Cell-based studies demonstrated that primary cortical neurons treated with conditioned media from microglial BV2 cells stimulated either with LPS/INF-γ or sonicated Aβ42 peptides resulted in approximately a 60% decrease in cell viability (Gan et al., J. Biol. Chem. 279:5565-5572, 2004). A higher expression of immunoproteasome is found in brain tissue from AD patients than in that of non-demented elderly adults (Mishto et al, Neurobiol Aging 27:54-66, 2006).

Patients suffering from Huntington's disease (HD), another neurodegenerative disorder, display motor dysfunction and cognitive decline over a period of years until death. Upon autopsy, the presence of inclusions or intraneuronal aggregates, caused by a polyQ expansion mutation (also referred to as a CAG triplet repeat expansion), can be detected, accompanied by significant atrophy in the striatum and cortex portions of the brain. Immunohistochemistry revealed that there was a significant enhancement in immunoproteasome expression in the striatum and frontal cortex of brains from HD patients as compared to those from age-matched normal adults (Diaz-Hernandez et al, J Neurosci 23:11653-1161, 2003). Upon further analysis, it was discovered that the enhancement predominantly occurred in the degenerating neurons. Using a mouse model of HD, the researchers noted a selective increase in both chymotrypsin- and trypsin-like activities in the affected and aggregate-containing regions of the brain, primarily the cortex and striatum (Diaz-Hernandez et al, J Neurosci 23:11653-1161, 2003).

Accordingly, certain embodiments of the invention relate to the use of proteasome inhibitor compositions disclosed herein for the treatment of neurodegenerative diseases. Neurodegenerative diseases and conditions includes, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R. et al., J. Clin. Invest. (2003) 111: 1771-1782), therefore suggesting that the ubiquitin-proteasome machinery regulates osteoblast differentiation and bone formation. Therefore, the disclosed proteasome inhibitor compositions may be useful in the treatment and/or prevention of diseases associated with bone loss, such as osteoporosis.

Cancer is a general term for disease characterized by uncontrolled, abnormal growth of cells. Many cancers arise via multistep pathways involving inactivation of tumor suppressor proteins and activation of oncogenic peptides. Cancer cells can spread to other parts of the body through the lymphatic system or blood stream. Usually, cancer is classified according to the type of tissue or cell most prominently involved. As noted previously, proteasome inhibition has already been validated as a therapeutic strategy for the treatment of cancer, particularly multiple myeloma. As shown in FIG. 1, multiple myeloma cells possess both forms of the proteasome, although the ratio can vary somewhat. Multiple myeloma is a hematologic disease characterized by an excessive number of abnormal plasma cells in the bone marrow. Plasma cells develop from B-cells, thus it is not surprising that other B-cell malignancies would also express immunoproteasome to some extent. Except for two chronic mylogenous leukemia cell lines, heme-related cancers (e.g., multiple myeloma, leukemias and lymphomas) generally appear to express immunoproteasome (FIG. 1). Cancer cells originating from lymphoid cells express 30% or more immunoproteasome. In certain embodiments, the invention relates to a method for the treatment of cancer, comprising administering a therapeutically effective amount of a compound described herein. In certain preferred embodiments, the cancer is a heme-related disorder.

Intriguingly, some cancers (e.g., solid tumors, head and neck squamous cell carcinoma, cervical carcinoma and small cell lung carcinoma) appear to have down regulated immunoproteasome expression (Evans et al, J Immunol 167:5420, 2001; Meissner et al, Clin Cancer Res 11:2552, 2005; Restifo et al, J Exp Med 177:265-272, 1993). This appears to be correlated with deficient antigen processing and may be a strategy used by tumor cells to escape immune surveillance. The treatment of the cells with INF-γ could induce immunoproteasome expression. Therefore, certain embodiments of the invention relate to a method of treating cancers comprising administering to a subject in need of such treatment an effective amount of INF-γ or TNF-α and a proteasome inhibitor compound disclosed herein.

Administration

Compounds prepared as described herein can be administered in various forms, depending on the disorder to be treated and the age, condition, and body weight of the patient, as is well known in the art. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In other cases, the inhibitors useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of an inhibitor(s) as an active ingredient. A composition may also be administered as a bolus, electuary, or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an inhibitor(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

The inhibitor(s) can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions of this invention suitable for parenteral administration comprise one or more inhibitors(s) in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

These inhibitors(s) may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the inhibitor(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The concentration of a disclosed compound in a pharmaceutically acceptable mixture will vary depending on several factors, including the dosage of the compound to be administered, the pharmacokinetic characteristics of the compound(s) employed, and the route of administration. In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

Another aspect of the invention provides a conjoint therapy wherein one or more other therapeutic agents are administered with the proteasome inhibitor. Such conjoint treatment may be achieved by way of the simultaneous, sequential, or separate dosing of the individual components of the treatment.

In certain embodiments, a compound of the invention is conjointly administered with one or more other proteasome inhibitor(s).

In certain embodiments, a compound of the invention is conjointly administered with a chemotherapeutic. Suitable chemotherapeutics may include, natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates (busulfan), nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine); aromatase inhibitors (anastrozole, exemestane, and letrozole); and platinum coordination complexes (cisplatin, carboplatin), procarbazine, hydroxyurea, mitotane, aminoglutethimide; hormones (i.e. estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing.

In certain embodiments, a compound of the invention is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof.

In certain embodiments, a compound of the invention is conjointly administered with an immunotherapeutic agent. Suitable immunotherapeutic agents may include, but are not limited to, cyclosporine, thalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab.

EXEMPLIFICATION

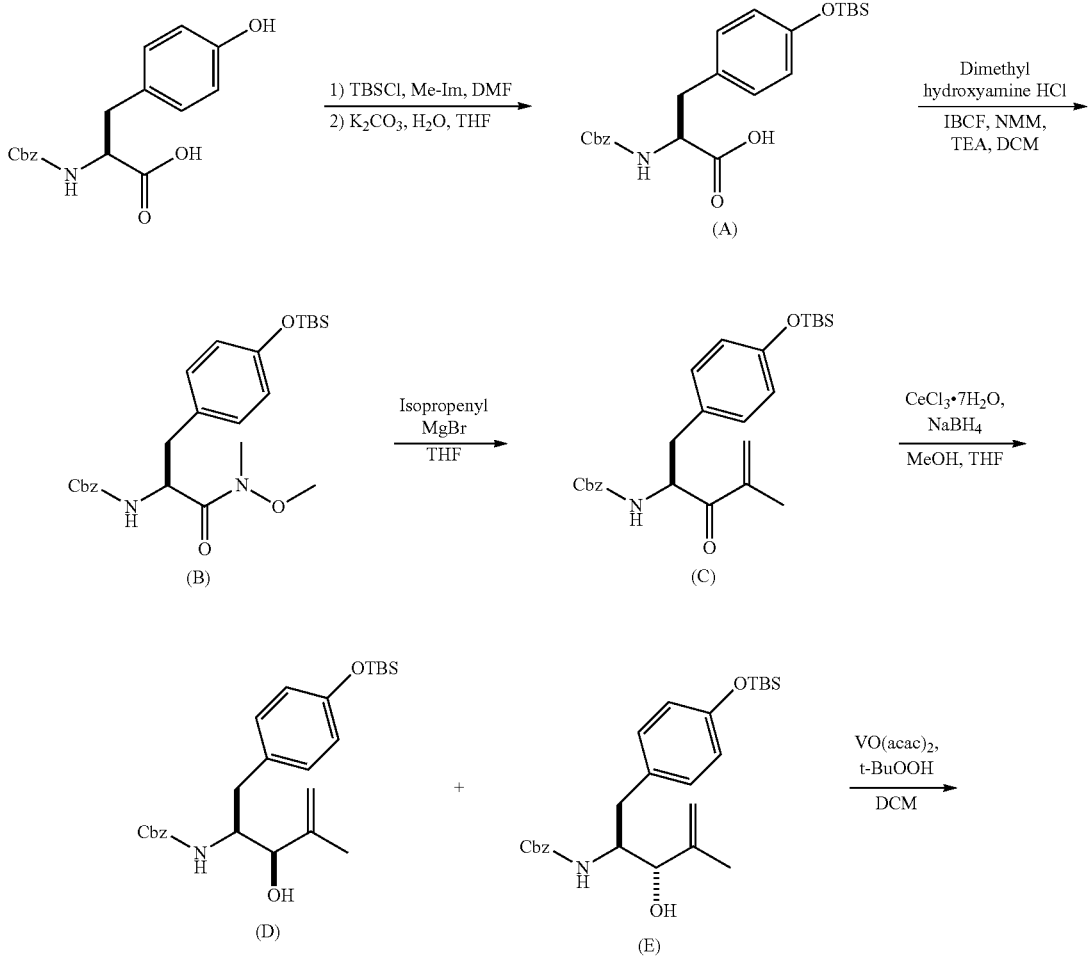

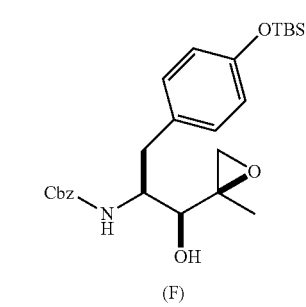
(F)

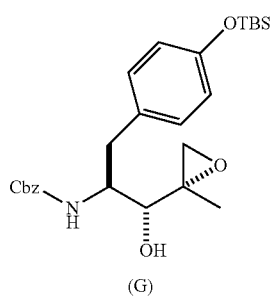
(G)

4/1 Ratio

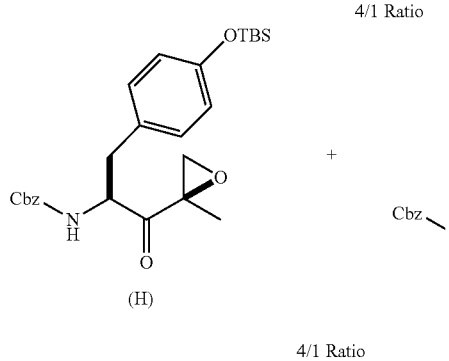
(H)

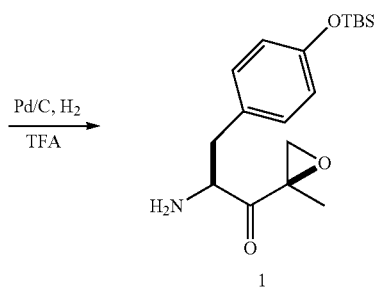
(I)

4/1 Ratio

Synthesis of (A)

To a solution of Cbz-Trp-OH (10 g, 29 mmol) in DMF (150 mL) was added Me-Im (25.2 mL, 458 mmol) dropwise. The solution was allowed to stir for 10 minutes followed by the addition of TBSCl (23.9 g, 158 mmol). The resulting solution was allowed to stir overnight. Water (100 mL) was then added and the mixture was extracted with EtOAc (3×50 mL). The combined organic layers were washed with water (3×50 mL) and brine (50 m 1), dried over $MgSO_4$, filtered, and concentrated under reduced pressure to yield an oil that was dissolved in 1:1 water/THF (200 mL) and $K_2CO_3$ (440 mg, 0.031 mmol) was added to the solution. The resulting solution was allowed to stir overnight. The organic solvent was then removed under reduced pressure and the pH adjusted to 2 with 1N HCl. The resulting solution was extracted with EtOAc (3×75 mL) and the combined organic layers were dried over $MgSO_4$, filtered, and concentrated under reduced pressure to yield (A).

Synthesis of (B)

To a solution of dimethyl hydroxylamine hydrochloride (3.6 g, 36.9 mmol) in DCM (20 mL) at 0° C. was added diisopropylethylamine (DIEA) (5 mL, 54.7 mmol) dropwise. The resulting solution was allowed to stir for 20 minutes.

To a solution of (A) in DCM (20 mL) at 0° C. was added isobutylchlorformate (IBCF) (5 mL, 51.5 mmol) dropwise, followed by the drop wise addition of N-methylmorpholine (NMM) (4.0 mL, 56.7 mmol). The resulting solution was allowed to stir for 10 minutes before adding it to the previously prepared dimethyl hydroxylamine hydrochloride/DIEA solution. The mixture was allowed to stir for 3 hrs at 0° C., followed by the addition of water (50 mL). The layers were separated and the water layer was washed with DCM (3×15 mL). The combined organic layers were washed with 1N HCl (3×20 mL) and brine (20 mL), dried over $MgSO_4$, filtered and concentrated under reduced pressure to yield an oil that was purified by flash chromatography using 20 to 40% EtOAc/hexanes as the eluent to yield (B).

Synthesis of (C)

To a solution of (B) (6.82 g, 14.4 mmol) in a solution of THF (40 mL) at −20° C. was added a solution isopropenyl magnesium bromide (90 mL, 0.5 M in THF) while keeping the internal temperature below −5° C. The solution was allowed to stir for 3 hrs at 0° C. followed by the addition of 1N HCl (20 mL). The solution was filtered through Celite 521 and the filter cake washed with EtOAc. The organic solvent was then removed under reduced pressure and the remaining aqueous solution was extracted with EtOAc (3×20 mL). The combined organic layers were washed with sat. $NaHCO_3$ (3×, 15 mL) and brine (15 mL), dried over $MgSO_4$, filtered, and concentrated under reduced pressure to provide an oil that was purified by flash chromatography using 10 to 20% EtOAc/hexanes as the eluent to yield (C).

Synthesis of (D) and (E)

To a solution of (C) (3.06 g, 6.75 mmol) in MeOH (40 mL) and THF (40 mL) was added $CeCl_3 \cdot 7H_2O$ (3.64 g, 9.77 mmol). The resulting mixture was allowed to stir until it became homogenous. The solution was then cooled to 0° C. and $NaBH_4$ (369 mg, 9.75 mmol) was added over 10 minutes. The solution was allowed to stir for 1 hr followed by the addition of AcOH (5 mL) with continued stirring for 20 minutes. The solvent was evaporated under reduced pressure and the resulting residue was diluted with water (30 mL) and extracted with EtOAc (3×10 mL). The combined organic layers were washed with water (3×10 mL) and brine (10 mL), dried over $MgSO_4$, filtered, and concentrated under reduced pressure to yield a 4/1 mixture of (D) and (E).

Synthesis of (F) and (G)

To a solution of (D) and (E) in DCM (90 mL) at 0° C. was added $VO(acac)_2$ (63 mg, 0.23 mmol), after stirring for 5 minutes t-BuOOH (2.25 mL, 6.0M in decane) was added dropwise. The resulting solution was allowed to stir for 2 hrs and was then filtered through Celite 521, and the filter cake was washed with DCM (20 mL). The combined organic layers were washed with sat. NaHCO$_3$ (3×20 mL) and brine (20 mL), dried over MgSO$_4$, filtered, and concentrated under reduced pressure to yield a 4/1 mixture of (F) and (G).

Synthesis of (H)

To a solution of Dess-Martin periodinane (6.75 g, 15.9 mmol) in DCM (75 mL) at 0° C. was added a solution of (F) and (G) in DCM (35 mL) dropwise. The solution was allowed to warm to room temperature and stir overnight. The solvent was then concentrated under reduced pressure and the residue was diluted with EtOAc (20 mL) and sat. NaHCO$_3$ (20 mL). The resulting mixture was filtered through Celite 521 and the filter cake was washed with EtOAc (20 mL). The layers were separated and the organic layer was washed with water (3×10 mL) and brine (10 mL), dried over MgSO$_4$, filtered, and concentrated under reduced pressure to provide an mixture of (H) and (I) (4/1) that was purified by flash chromatography using 15 to 40% EtOAc/hexanes as the eluent to yield (H).

Synthesis of 1

To a solution of (H) (50 mg, 1.06 mmol) in TFA (5 mL) was added Pd/C (14 mg, 10%). The resulting mixture was allowed to stir under 1 atmosphere of H$_2$ for 2 hrs followed by dilution with DCM (10 mL). The mixture was filtered through Celite 521 and the filter cake was washed with DCM (10 mL). The filtrate was concentrated under reduced pressure and the resulting residue was diluted with DCM (10 mL) and concentrated under reduced pressure a second time. The residue was placed under high vacuum for 2 hrs to provide 1.

Scheme 2: Synthesis of Example 2

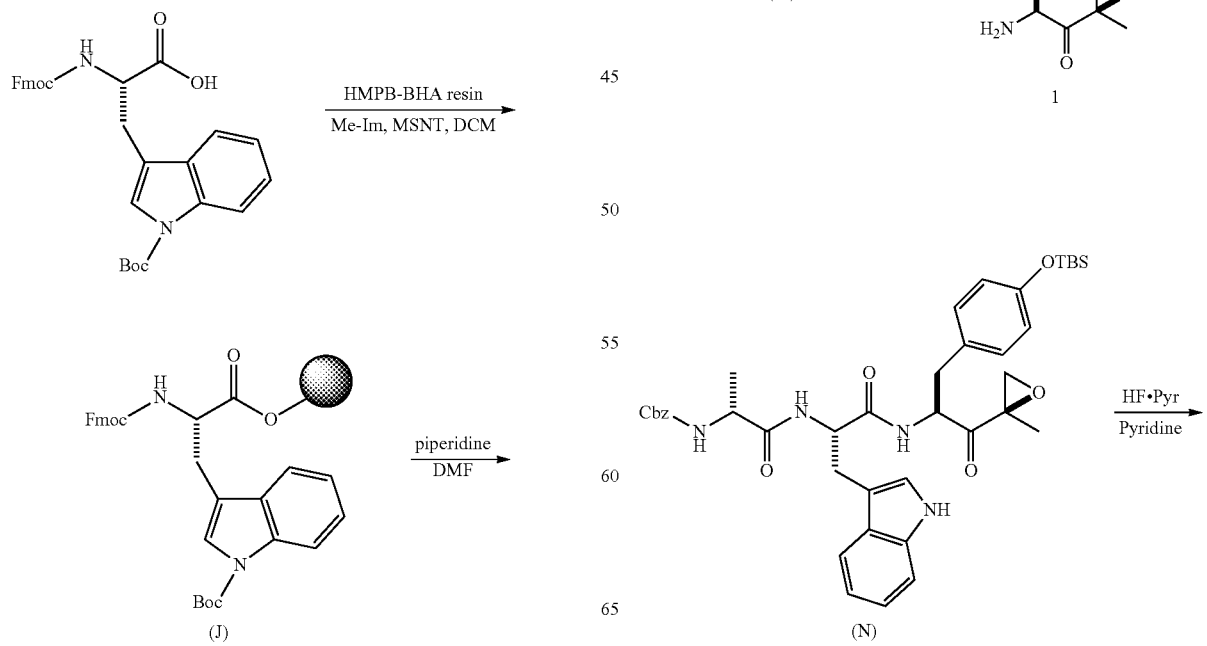

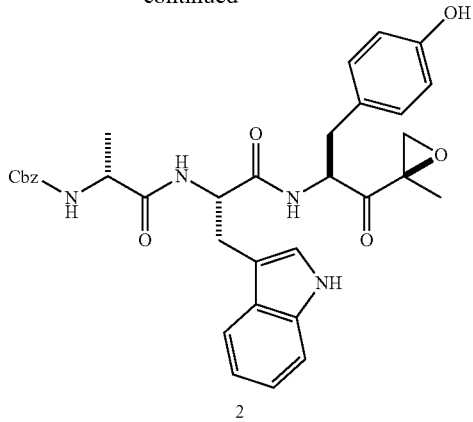

2

Synthesis of (J)

To a solution of Fmoc-Trp (Boc)-OH (2.4 mmol, 1.0 g,) in DCM (20 mL) was added Me-Im (6.7 mmol, 0.370 mL) and the mixture was stirred until the solution was homogenous, at which time 1-(mesitylene-2-sulfonyl)-3-nitro-1,2,4-triazole (MSNT) (2.9 mmol, 0.870 g,) was added. Once the MSNT had dissolved, the reaction mixture was added to HMPB-BHA resin (0.8 mmol, 1.25 g) and the resulting solution was allowed to shake for 45 minutes. The resin was filtered and washed with DMF (50 mL), MeOH (50 mL), and DCM (50 mL). The resin was then allowed to air dry to provide (J).

Synthesis of (K)

To (J) (0.40 mmol, 0.62 g) was added 20% piperidine/DMF (10 mL) and the resulting heterogeneous solution was allowed to shake for 20 minutes. The mixture was filtered and the resin was washed with DMF (20 mL), MeOH (20 mL), and DCM (20 mL) and allowed to air dry before subjecting it to the above reaction condition a second time to yield (K).

Synthesis of (L)

To (K) (0.40 mmol) was added DMF (20 mL), Cbz-D-Ala-OH (0.40 mmol, 0.090 g), DIEA (1.6 mmol, 0.12 mL), HOBT (0.64 mmol, 0.062 mg), and BOP (0.64 mmol, 0.178 g) and the reaction mixture was allowed to shake for 45 minutes. The reaction mixture was filtered and the resin was washed with DMF (40 mL), MeOH (40 mL), and DCM (40 mL), and allowed to air dry, to yield (L).

Synthesis of (M)

To (L) (0.08 mmol) was added 5% TFA/DCM (2 mL) and the mixture was allowed to shake for 20 minutes. The reaction was filtered and the resin was washed with DCM (10 mL). The volatiles were removed under reduced pressure and the resulting oil was diluted with DCM (10 mL) and evaporated a total of three times to yield (M).

Synthesis of (N)

To a stirred solution of (M) (0.11 mmol, 0.019 g) in MeCN (4 mL) and DMF (1 mL) was added (M) (0.1 mmol), DIEA (2.9 mmol, 0.5 mL), HOBT (0.2 mmol, 0.032 g), and HBTU (0.23 mmol, 0.087 g) and the mixture was stirred at room temperature overnight. The reaction was diluted with sat NaHCO₃ (15 mL) and extracted with EtOAc. The organic layer was washed with sat. NaHCO₃ and brine, dried over MgSO₄, and the volatiles removed under reduced pressure. The crude material was purified by flash chromatography using 20 to 40% EtOAc/hexanes as the eluent to afford (N).

Synthesis of 2

To a stirred solution of (N) (0.1 mmol) in pyridine (1.5 mL) and THF (3.0 mL) at 0° C. was added a solution of HF/pyridine dropwise. The solution was allowed to stir for 2 hours at 0° C. prior to the addition of water (5.0 mL) and extraction with EtOAc. The combined organic layers were washed with sat. NaHCO₃ and brine, dried over MgSO₄, filtered and the volatiles removed under reduced pressure. The crude material was purified by flash chromatography using 30 to 60% EtOAc/hexanes as the eluent, to afford 2 (4.2 mg).

Scheme 3: Synthesis of Example 3

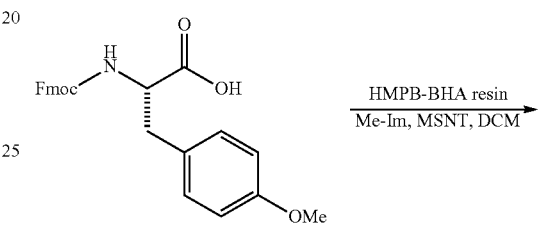

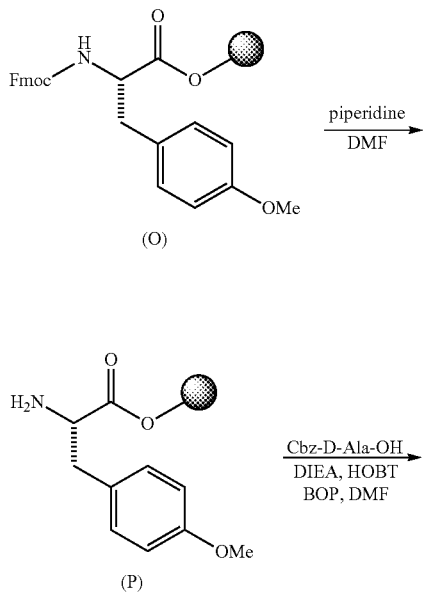

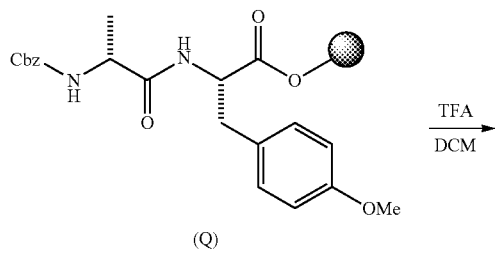

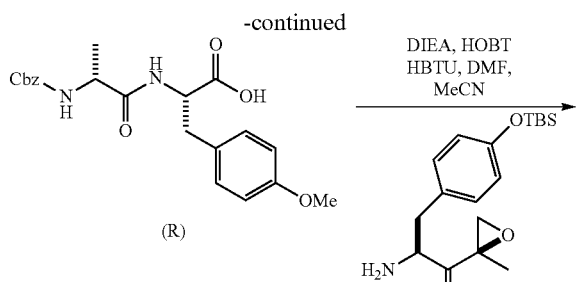

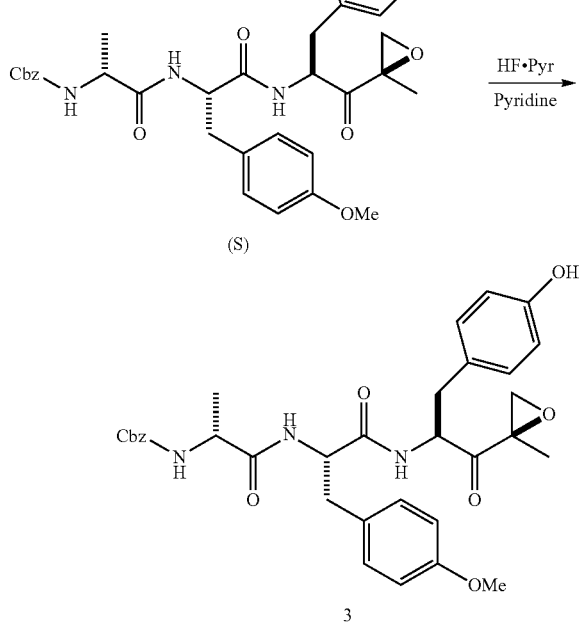

(0.64 mmol, 0.062 mg), and BOP (0.64 mmol, 0.178 g) and the reaction mixture was allowed to shake for 45 minutes. The reaction mixture was filtered and the resin was washed with DMF (40 mL), MeOH (40 mL), and DCM (40 mL), and allowed to air dry, to yield (Q).

Synthesis of (R)

To (Q) (0.08 mmol) was added 5% TFA/DCM (2 mL) and the mixture was allowed to shake for 20 minutes. The reaction was filtered and the resin was washed with DCM (10 mL). The volatiles were then removed under reduced pressure and the resulting oil was diluted with DCM (10 mL) and evaporated a total of three times to yield (R).

Synthesis of (S)

To a stirred solution of 1 (0.11 mmol, 0.019 g) in MeCN (4 mL) and DMF (1 mL) was added (R) (0.1 mmol), DIEA (2.9 mmol, 0.5 mL), HOBT (0.2 mmol, 0.032 g), and HBTU (0.23 mmol, 0.087 g) and the mixture was stirred at room temperature overnight. The reaction was diluted with sat NaHCO$_3$ (15 mL) and extracted with EtOAc. The organic layer was washed with sat. NaHCO$_3$, and brine, dried over MgSO$_4$, filtered, and concentrated under reduced pressure. The resulting material was purified by flash chromatography using 20 to 40% EtOAc/hexanes as the eluent to afford (S).

Synthesis of 3

To a stirred solution of (S) (0.1 mmol), in pyridine (1.5 mL) and THF (3.0 mL) at 0° C. was added a solution of HF/Pyridine dropwise. The solution was allowed to stir for 2 hours at 0° C. followed by the addition of water (5.0 mL) and extraction with EtOAc. The organic layer was then washed with sat. NaHCO$_3$, and brine, dried over MgSO$_4$, filtered, and concentrated under reduced pressure. The resulting material was purified by flash chromatography using 30 to 60% EtOAc/hexanes as the eluent, to afford 3 (6.7 mg).

Synthesis of (O)

To a solution of Fmoc-Tyr(Me)—OH (1.9 mmol, 0.80 g,) in DCM (20 mL) was added Me-Im (6.7 mmol, 0.370 mL). When the solution was homogenous, MSNT (2.9 mmol, 0.870 g,) was added and the mixture was stirred until the MSNT dissolved, at which time HMPB-BHA resin (0.64 mmol, 1.00 g) and the resulting solution was allowed to shake for 45 minutes. The resin was filtered and washed with DMF (50 mL), MeOH (50 mL), and DCM (50 mL) and then the resin was allowed to air dry, to yield (O).

Synthesis of (P)

To (O) (0.40 mmol, 0.62 g) was added 20% piperidine/DMF (10 mL) and the resulting heterogenous solution was allowed to shake for 20 minutes. The mixture was filtered and the resin was washed with DMF (20 mL), MeOH (20 mL), and DCM (20 mL) and allowed to air dry. The resin was then subjected to the above reaction condition a second time to yield (P).

Synthesis of (Q)

To (P) (0.40 mmol) was added DMF (20 mL), Cbz-D-Ala-OH (0.40 mmol, 0.090 g), DIEA (1.6 mmol, 0.12 mL), HOBT Scheme 4: Synthesis of Example 4

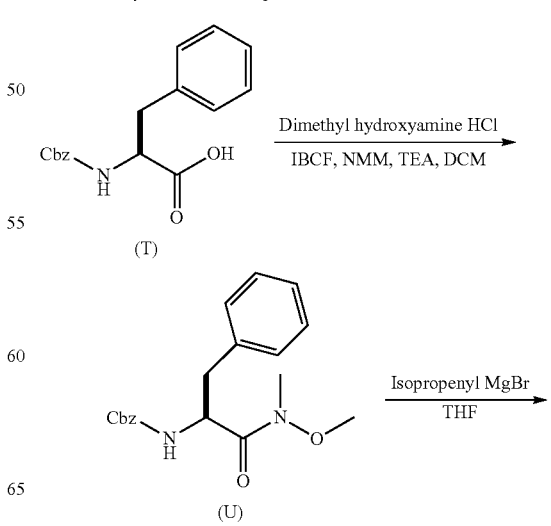

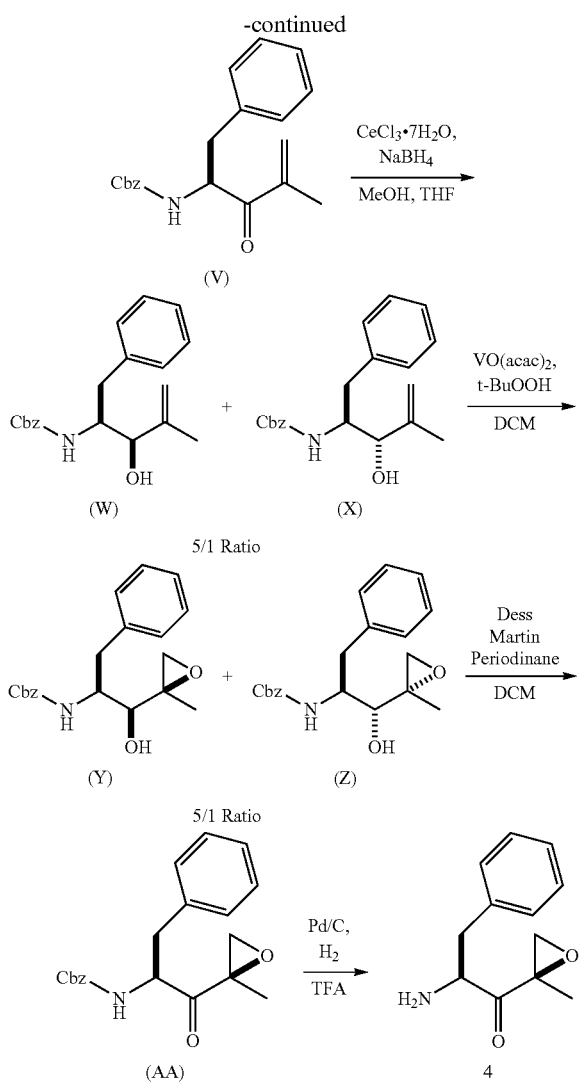

Synthesis of (U)

To a solution of dimethyl hydroxylamine hydrochloride (18.4 g, 226.3 mmol) in DCM (400 mL) at 0° C. was added DIEA (25.8 mL, 282 mmol) dropwise. The resulting solution was allowed to stir for 20 minutes.

To a solution of Cbz-Phe-OH (50 g, 169 mmol) in DCM (400 mL) at 0° C. was added IBCF (24.4 mL, 266 mmol) dropwise, followed by the dropwise addition of NMM (20.7 mL, 293 mmol). The resulting solution was allowed to stir for 10 minutes then added to the previously prepared dimethyl hydroxylamine hydrochloride/DIEA solution. The mixture was allowed to stir for 3 hrs at 0° C. followed by the addition of water (250 mL). The layers were then separated and the water layer washed with DCM (3×100 mL). The combined organic layers were washed with 1N HCl (3×100 mL) and brine (100 mL), dried over $MgSO_4$, filtered, and concentrated under reduced pressure to yield an oil that was purified by flash chromatography using 20 to 40% EtOAc/hexanes as the eluent, to yield (U).

Synthesis of (V)

To a solution of (U) (47 g, 145 mmol) in a solution of THF (400 mL) at −20° C. was added a solution isopropenyl magnesium bromide (800 mL, 0.5 M in THF) while keeping the internal temperature below −5° C. The solution was allowed to stir for 3 hrs at 0° C. followed by the addition of 1N HCl (200 mL). The solution was filtered through Celite 521 and the filter cake washed with EtOAc. The organic solvent was then removed under reduced pressure and the remaining aqueous solution was extracted with EtOAc (3×200 mL). The combined organic layers were washed with satd. $NaHCO_3$ (3×150 mL) and brine (150 mL), dried over $MgSO_4$, filtered, and concentrated under reduced pressure to yield an oil that was purified by flash chromatography using 20 to 40% EtOAc/hexanes as the eluent to yield (V).

Synthesis of (W) and (X)

To a solution of (V) (30.03 g, 92.0 mmol) in MeOH (500 mL) and THF (500 mL) was added $CeCl_3.7H_2O$ (48.04 g, 130 mmol). The resulting solution was allowed to stir until it became homogenous. The solution was then cooled to 0° C. and $NaBH_4$ (4.90 mg, 129 mmol) was added over a 10 minute period. The solution was allowed to stir for 1 hr followed by the addition of AcOH (70 mL) with continued stirring for 20 minutes. The mixture was then concentrated under reduced pressure and the resulting residue diluted with water (400 mL) and extracted with EtOAc (3×130 mL). The combined organic layers were washed with water (3×, 130 mL) and brine (130 mL), dried over $MgSO_4$, filtered, and concentrated under reduced pressure to yield a 5/1 mixture of (W) and (X).

Synthesis of (Y) and (Z)

To a solution of (W) and (X) in DCM (500 mL) at 0° C. was added $VO(acac)_2$ (900 mg, 3.26 mmol), after stirring for 5 minutes t-BuOOH (30 mL, 6.0M in decane) was added dropwise. The resulting solution was allowed to stir for 2 hrs then filtered through Celite 521 and the filter cake was washed with DCM (200 mL). The filtrate was then washed with satd. $NaHCO_3$ (3×200 mL) and brine (200 mL), dried over $MgSO_4$, filtered, and concentrated under reduced pressure to yield a 5/1 mixture of (Y) and (Z).

Synthesis of (AA)

To a solution of Dess-Martin periodinane (40 g, 94.2 mmol) in DCM (300 mL) at 0° C. was added a solution of (Y) and (Z) in DCM (100 mL) dropwise. The solution was then allowed to warm to room temperature and stir overnight. The reaction mixture was then concentrated under reduced pressure and the residue diluted with EtOAc (120 mL) and satd. $NaHCO_3$ (120 mL). The resulting mixture was filtered through Celite 521 and the filter cake washed with EtOAc (120 mL). The layers were separated and the organic layer was washed with water (3×60 mL) and brine (60 mL), dried over $MgSO_4$ filtered, and concentrated under reduced pressure to give an oil that was purified by flash chromatography using 15 to 40% EtOAc/hexanes as the eluent to yield (AA).

Synthesis of 4

To a solution of (AA) (50 mg, 1.06 mmol) in TFA (5 mL) was added Pd/C (14 mg, 10%). The resulting mixture was allowed to stir under 1 atmosphere $H_2$ for 2 hrs, and then diluted with DCM (10 mL). The mixture was filtered through Celite 521 and the filter cake washed with DCM (10 mL). The filtrate was then concentrated under reduced pressure and the residue diluted with DCM (10 mL) and concentrated under reduced pressure a second time. The residue was placed under high vacuum for 2 hrs to yield 4.

Scheme 5: Synthesis of Example 5

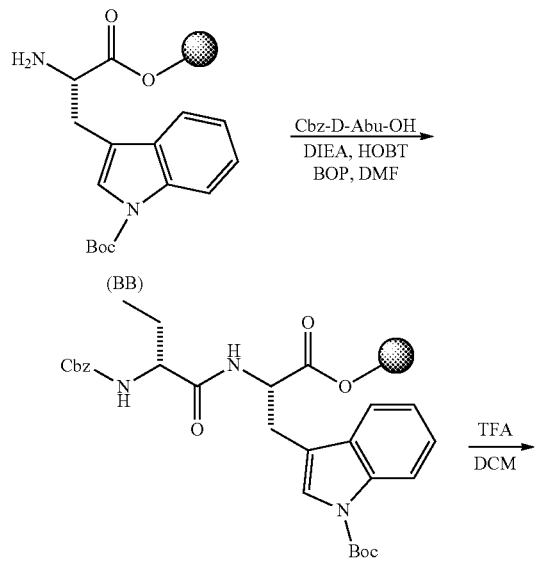

Synthesis of (CC)

To (BB) (0.06 mmol) was added DMF (2 mL), Cbz-D-Abu-OH (0.12 mmol, 0.032 g), DIEA (0.256 mmol, 0.075 mL), HOBT (0.102 mmol, 0.010 mg), and BOP (0.102 mmol, 0.075 g) and the reaction mixture was allowed to shake for 45 minutes. The reaction mixture was then filtered and the resin washed with DMF (4 mL), MeOH (4 mL), and DCM (4 mL), and allowed to air dry, to yield (CC).

Synthesis of (DD)

To (CC) (0.08 mmol) was added 50% TFA/DCM (2 mL) and the mixture was allowed to shake for 20 minutes. The reaction was filtered and the resin was washed with DCM (10 mL). The solution was then under reduced pressure and the resulting oil was diluted with DCM (10 mL) and evaporated a total of three times to yield (DD).

Synthesis of 5

To a stirred solution of 4 (0.11 mmol, 0.019 g) in MeCN (4 mL) and DMF (1 mL) was added (DD) (0.1 mmol), DIEA (2.9 mmol, 0.5 mL), HOBT (0.2 mmol, 0.032 g), and HBTU (0.23 mmol, 0.087 g) and the mixture was stirred at room temperature overnight. The reaction was then diluted with sat NaHCO$_3$ (15 mL) and extracted with EtOAc. The organic layer was washed with satd. NaHCO$_3$ and brine, dried over MgSO$_4$, filtered and concentrated under reduced pressure. The resulting material was purified by flash chromatography using 25 to 55% EtOAc/hexanes as the eluent to afford 5 (12.0 mg).

Scheme 6: Synthesis of Example 6

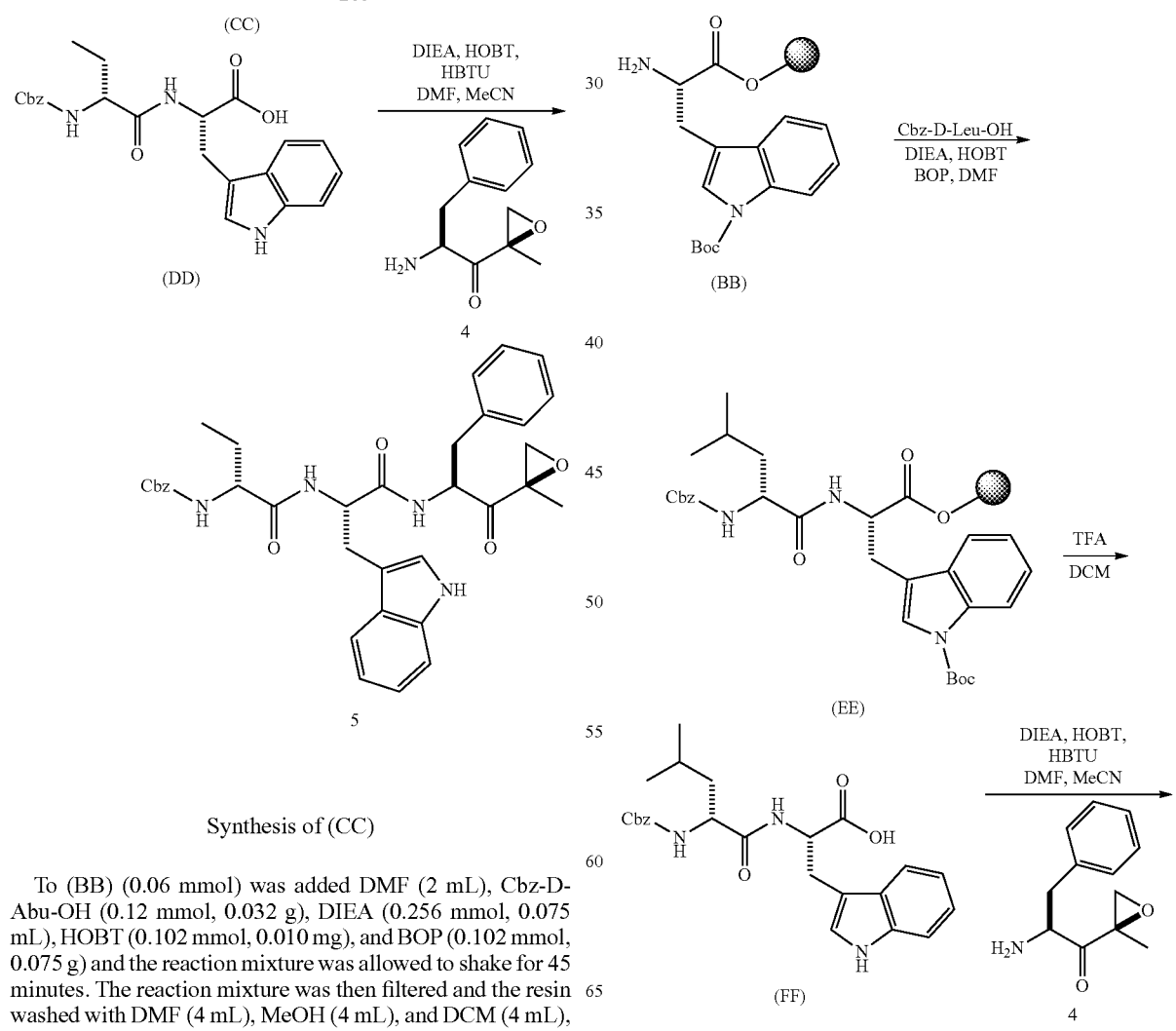

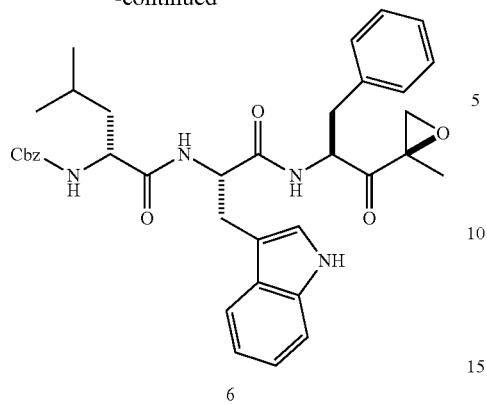

6

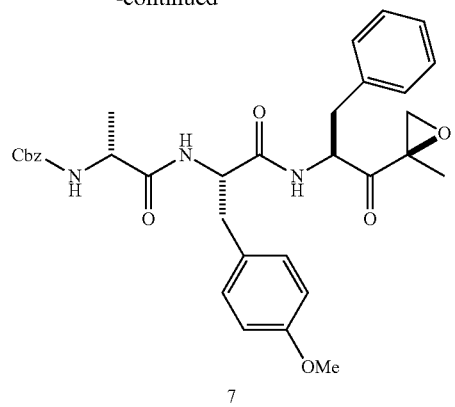

7

Synthesis of (EE)

To (BB) (0.06 mmol) was added DMF (2 mL), Cbz-D-Leu-OH (0.12 mmol, 0.032 g), DIEA (0.256 mmol, 0.075 mL), HOBT (0.102 mmol, 0.010 mg), and BOP (0.102 mmol, 0.075 g) and the reaction mixture was allowed to shake for 45 minutes. The reaction mixture was then filtered and the resin washed with DMF (4 mL), MeOH (4 mL), and DCM (4 mL), and allowed to air dry, to yield (EE).

Synthesis of (FF)

To (FF) (0.08 mmol) was added 50% TFA/DCM (2 mL) and the mixture was allowed to shake for 20 minutes. The reaction was filtered and the resin washed with DCM (10 mL). The volatiles were removed under reduced pressure and the resulting oil was diluted with DCM (10 mL) and evaporated a total of three times to yield (FF).

Synthesis of 6

To a stirred solution of 4 (0.11 mmol, 0.019 g) in MeCN (4 mL) and DMF (1 mL) was added (FF) (0.1 mmol), DIEA (2.9 mmol, 0.5 mL), HOBT (0.2 mmol, 0.032 g), and HBTU (0.23 mmol, 0.087 g) and the mixture was stirred at room temperature overnight. The reaction was then diluted with sat NaHCO$_3$ (15 mL) and extracted with EtOAc. The organic layer was washed with satd. NaHCO$_3$ and brine, dried over MgSO$_4$, filtered, and concentrated under reduced pressure. The resulting material was then purified by flash chromatography using 25 to 55% EtOAc/hexanes as the eluent to afford 20 (14.0 mg).

Synthesis of 7

To a stirred solution of 4 (0.11 mmol, 0.019 g) in MeCN (4 mL) and DMF (1 mL) was added (R) (0.1 mmol), DIEA (2.9 mmol, 0.5 mL), HOBT (0.2 mmol, 0.032 g), and HBTU (0.23 mmol, 0.087 g) and the mixture was stirred at room temperature overnight. The reaction was then diluted with satd. NaHCO$_3$ (15 mL) and extracted with EtOAc. The organic layer was washed with satd. NaHCO$_3$ and brine, dried over MgSO$_4$, filtered, and concentrated under reduced pressure. The resulting material was purified by flash chromatography using 25 to 55% EtOAc/hexanes as the eluent to afford 7 (10.5 mg).

Scheme 8: Synthesis of Example 8

Scheme 7: Synthesis of Example 7

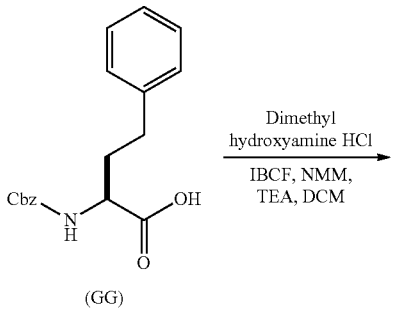

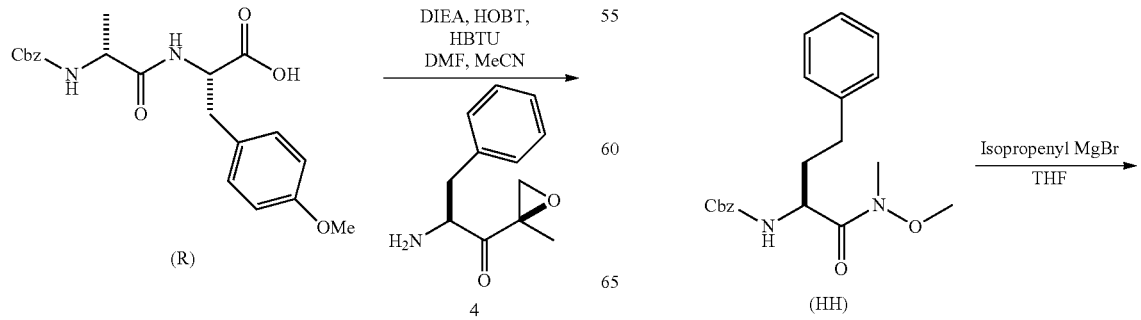

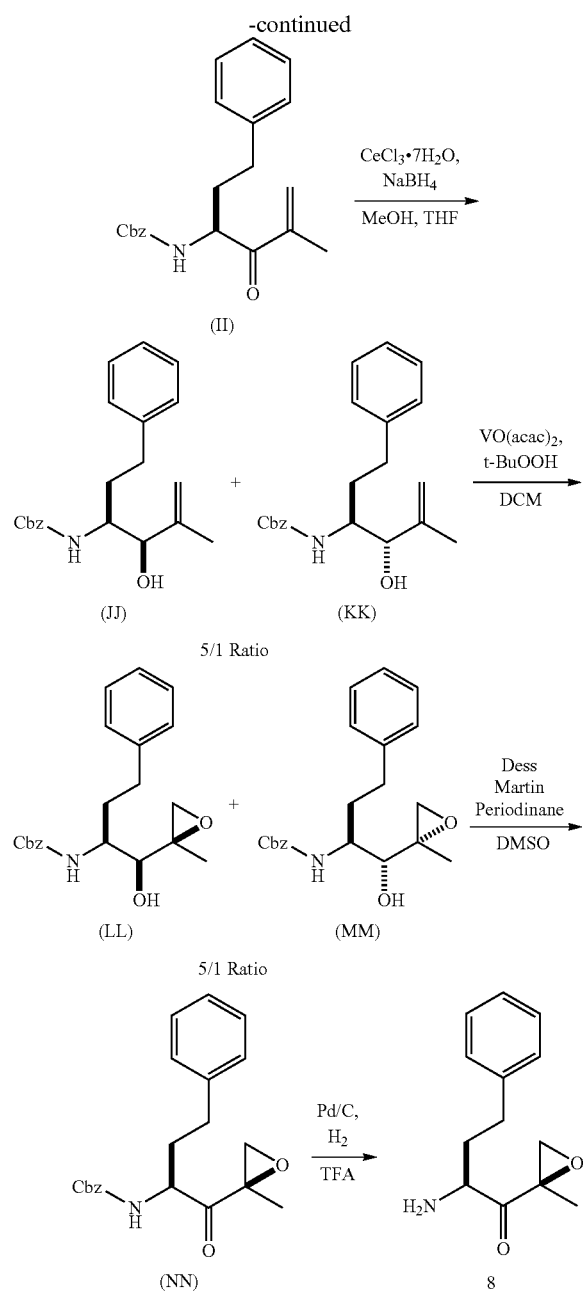

Synthesis of (HH)

To a solution of dimethyl hydroxylamine hydrochloride (331 mg, 3.4 mmol) in DCM (20 mL) at 0° C. was added triethylamine (343 mg, 3.4 mmol) dropwise. The resulting solution was allowed to stir for 20 minutes.

To a solution of Cbz-HomoPhe-OH (1.0 g, 3.2 mmol) in DCM (100 mL) at 0° C. was added IBCF (460 mg, 3.35 mmol) dropwise, followed by the dropwise addition of NMM (343 mg, 3.4 mmol). The resulting solution was allowed to stir for 10 minutes and then added to the previously prepared dimethyl hydroxylamine HCl/TEA solution. The resulting mixture was stirred at 0° C. for 3 hrs followed by the addition of water (50 mL). The layers were separated and the aqueous layer was extracted with DCM (3×100 mL). The combined organic layers were washed with 1N HCl (30 mL) and brine (30 mL), dried over MgSO$_4$, filtered, and concentrated under reduced pressure. The resulting material was then purified by flash chromatography using EtOAc/hexanes (1:3) as the eluent to yield intermediate (HH) (0.92 g).

Synthesis of (II)

To a solution of (HH) (920 mg, 2.6 mmol) in THF (50 mL) at −20° C. was added a solution of isopropenyl magnesium bromide (26 mL, 12.9 mmol, 0.5 M in THF). The resulting solution was allowed to stir at 0° C. for 6 hours followed by the addition of 1N HCl (10 mL). The resulting mixture was filtered through Celite 521 and the filter cake was washed with ethyl acetate. The layers were separated and aqueous phase was extracted with ethyl acetate (3×20 mL). The combined organic layers were washed with satd. NaHCO$_3$ (30 mL) and brine (30 mL), dried over MgSO$_4$, filtered and concentrated under reduced pressure. The resulting material was purified by flash chromatography using EtOAc/hexanes (1:3) as the eluent to yield (II) (700 mg).

Synthesis of (JJ) and (KK)

To a solution of (II) (700 mg, 2.1 mmol) in DCM (50 mL) at 0° C. was added CeCl$_3$.7H$_2$O (942 mg, 2.52 mmol) and NaBH$_4$ (98 mg, 2.52 mmol) successively. The solution was stirred at room temperature overnight followed by the addition of AcOH (5 mL). The mixture was concentrated under reduced pressure and then diluted with EtOAc (100 mL) and satd. NaHCO$_3$ (50 mL). The aqueous layer was then extracted with EtOAc (2×50 mL) and the combined organic layers were dried over Na$_2$SO$_4$, filtered, and concentrated under reduced pressure to a yellow oil that was purification by flash chromatography using EtOAc/hexanes (1:3) as the eluent to yield (JJ) and (KK) in a 5/1 ratio.

Synthesis of (LL) and (MM)

To a solution of (JJ) and (KK) in THF (50 mL) at 0° C. was added VO(acac)$_2$ (18 mg, 0.066 mmol) and t-BuOOH (0.9 mL, 6.0M in decane) successively. The resulting solution was stirred at room temperature for 10 hours then filtered through Celite 521 and the filter cake was washed with EtOAc (100 mL). The combined organic layers were washed with satd. NaHCO$_3$ (10 mL) and brine (10 mL), dried over MgSO$_4$, filtered and concentrated under reduced pressure to give (LL) and (MM) (585 mg) in a 5/1 ratio.

Synthesis of (NN)

To a solution of Dess-Martin Periodinane (1.40 g, 3.3 mmol) in DMSO (20 mL) at 0° C. was added (LL) and (MM) (585 mg) in DMSO (10 mL). The solution was stirred at room temperature for 6 hours, and then diluted with EtOAc (100 mL) and satd. NaHCO$_3$ (50 mL), the aqueous phase was then extracted with EtOAc (2×50 mL), and the combined organic layers were dried over Na$_2$SO$_4$, filtered, and concentrated under reduced pressure to give a yellow oil that was purified by flash chromatography using EtOAc/hexanes (2:3) as the eluent to yield (NN) (465 mg).

Synthesis of 8

To a solution of (NN) (290 mg, 0.82 mmol) in TFA (5 mL) was added Pd/C (14 mg, 10%). The resulting mixture was allowed to stir under 1 atmosphere H$_2$ for 2 hrs, and was then diluted with DCM (10 mL). The mixture was filtered through Celite 521 and the filter cake washed with DCM (10 mL). The was concentrated under reduced pressure and the residue diluted with DCM (10 mL) and concentrated under reduced pressure. The resulting residue was placed under high vacuum for 2 hrs, to yield 8.

Scheme 9: Synthesis of Example 9

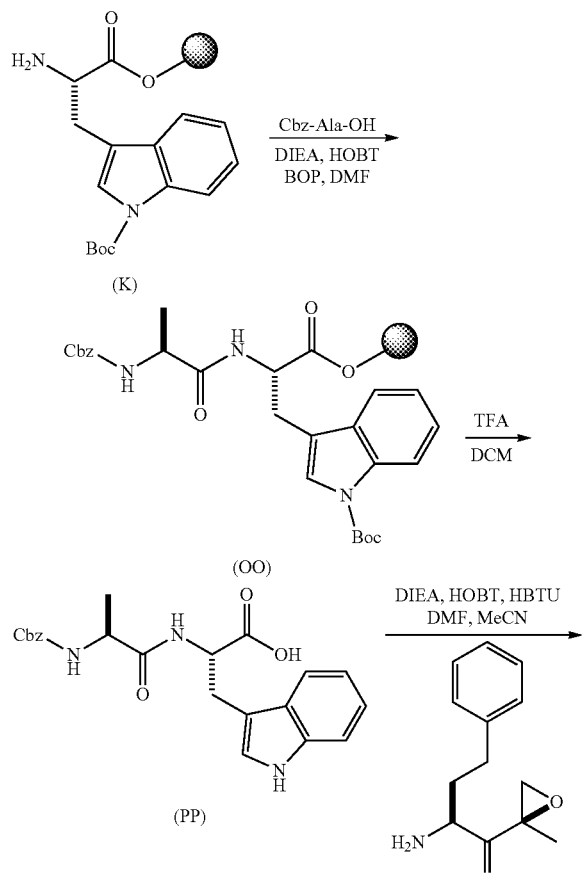

Synthesis of (OO)

To (K) (0.06 mmol) was added DMF (2 mL), Cbz-Ala-OH (0.12 mmol, 0.032 g), DIEA (0.256 mmol, 0.075 mL), HOBT (0.102 mmol, 0.010 mg), and BOP (0.102 mmol, 0.075 g) and the reaction mixture was allowed to shake for 45 minutes. The reaction mixture was then filtered and the resin washed with DMF (4 mL), MeOH (4 mL), and DCM (4 mL), and allowed to air dry, to yield (OO).

Synthesis of (PP)

To (OO) (0.08 mmol) was added 50% TFA/DCM (2 mL) and the mixture was allowed to shake for 20 minutes. The reaction was then filtered and the resin washed with DCM (10 mL). The volatiles were removed under reduced pressure and the resulting oil was diluted with DCM (10 mL) and evaporated a total of three times to yield (PP).

Synthesis of 9

To a stirred solution of 8 (0.11 mmol, 0.019 g) in MeCN (4 mL) and DMF (1 mL) was added (PP) (0.1 mmol), DIEA (2.9 mmol, 0.5 mL), HOBT (0.2 mmol, 0.032 g), and HBTU (0.23 mmol, 0.087 g) and the mixture was stirred at room temperature overnight. The reaction was then diluted with satd. NaHCO$_3$ (15 mL) and extracted with EtOAc. The organic layer was then washed with satd. NaHCO$_3$ and brine, dried over MgSO$_4$, filtered and concentrated under reduced pressure. The resulting material was purified by flash chromatography using 25 to 55% EtOAc/hexanes as the eluent, to afford 9 (7.8 mg).

Scheme 10: Synthesis of Example 10

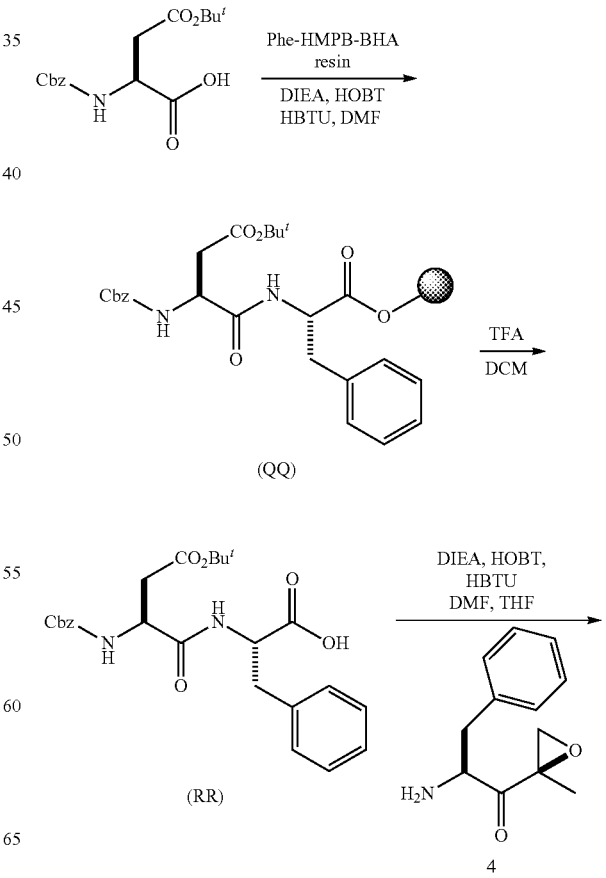

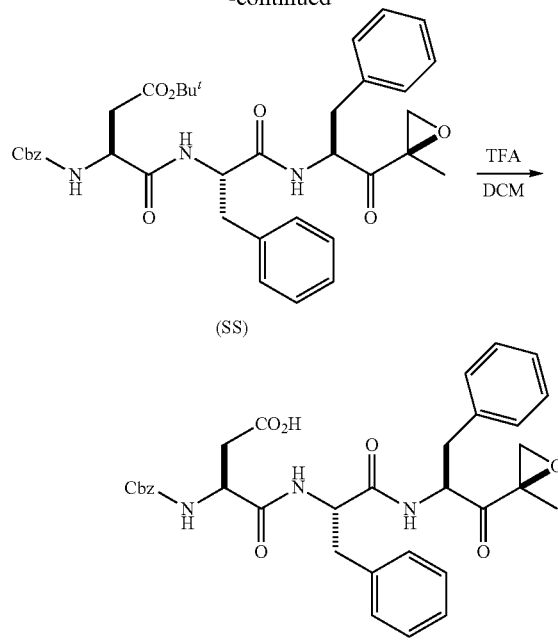

Synthesis of (QQ)

To a solution of Cbz-Asp (t-Bu)—OH (0.32 mmol, 108 mg) in DMF (2 mL) at 0° C. was added HOBT (0.51 mmol, 78 mg), HBTU (0.51 mmol, 194 mg), and DIEA (1.2 mmol, 0.2 mL). Once the resulting mixture became a homogenous solution, Phe-HMPB-BHA resin (0.13 mmol, 200 mg) was added and the resulting reaction mixture was allowed to shake at 0-4° C. overnight. The resin was filtered off and washed with DMF (3×5 mL) and DCM (3×5 mL). The resin was allowed to air dry to yield (QQ).

Synthesis of (RR)

To (QQ) (0.13 mmol) was added TFA/DCM (5 mL, 5:95) and the mixture was allowed to shake at 0-4° C. for 30 minutes. The reaction was then filtered and the resin washed with DCM (3×10 mL). The volatiles were removed under reduced pressure at 0° C. to yield (RR).

Synthesis of (SS)

To a 0° C. solution of (RR) (0.13 mmol) and 4 (0.12 mmol) in THF (5 mL) was added HOBT (0.18 mmol, 31 mg), HBTU (0.18 mmol, 76 mg) and DIEA (0.6 mmol, 0.1 mL), and the resulting reaction mixture was stirred at 0-4° C. overnight. The reaction mixture was then diluted with EtOAc (100 mL) and satd. $NaHCO_3$, and the aqueous phase was extracted with EtOAc. The combined organic layers were dried over $Na_2SO_4$, filtered, and concentrated under reduced pressure to give a yellow oil that was purified by HPLC, eluting with an MeCN/aq. $NH_4OAc$ solution, to give (SS).

Synthesis of 10

To a 0° C. solution of (SS) in DCM (5 mL) was added TFA acid (5 mL) dropwise and the resulting solution was stirred for 3 hrs. The reaction mixture was then concentrated under reduced pressure and the resulting residue was purified by HPLC, eluting with an MeCN/aq. $NH_4OAc$ solution, to give 10.

Scheme 11: Synthesis of Example 11

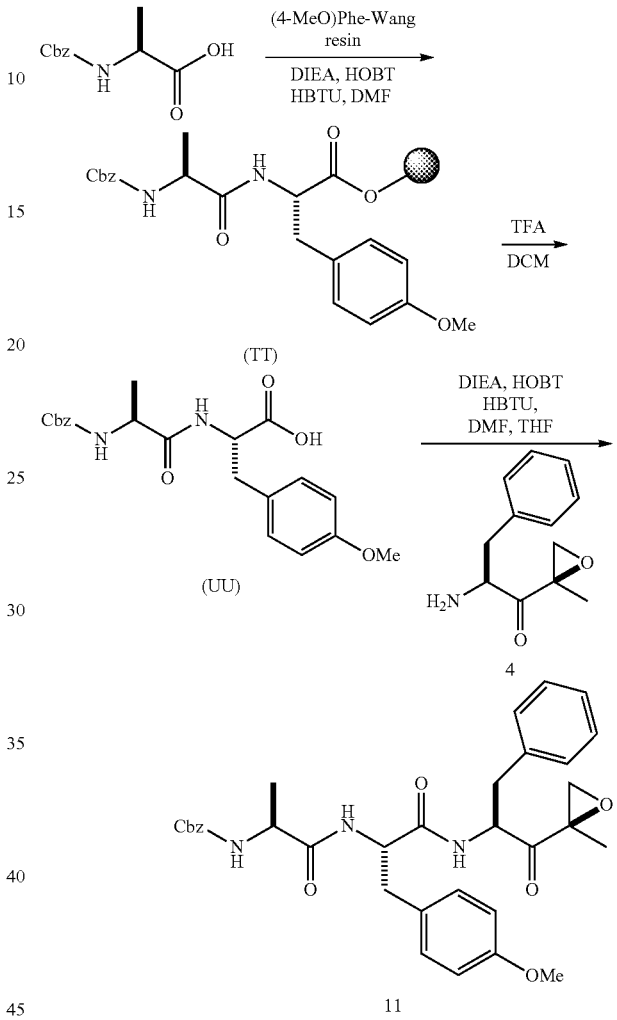

Synthesis of (TT)

To a 0° C. solution of Z-Ala-OH (0.32 mmol, 71 mg) in DMF (2 mL) was added HOBT (0.51 mmol, 78 mg), HBTU (0.51 mmol, 194 mg) and diisopropylethylamine (1.2 mmol, 0.2 mL). Once the resulting mixture became homogenous, Phe(4-MeO)-Wang-resin (0.13 mmol, 200 mg) was added and the resulting reaction mixture was allowed to shake overnight. The resin was then filtered off and washed with DMF (3×5 mL) and DCM (3×5 mL). The resulting resin was allowed to air dry to yield (TT).

Synthesis of (UU)

To (TT) (0.13 mmol) was added 50% TFA/DCM (5 mL) and the mixture was allowed to shake for 30 minutes. The reaction was then filtered and the resin washed with DCM (3×10 mL). The volatiles were removed under reduced pressure to yield (UU).

Synthesis of 11

To a 0° C. solution of (UU) (0.13 mmol) and 4 (0.12 mmol) in THF (5 mL) was added HOBT (0.18 mmol, 31 mg), HBTU (0.18 mmol, 76 mg) and DIEA (0.6 mmol, 0.1 mL). The resulting reaction mixture was stirred at 0-4° C. overnight followed by dilution with EtOAc (100 mL) and satd. NaHCO₃. The aqueous phase was then extracted with EtOAc and the combined organic layers were dried over Na₂SO₄, filtered, and concentrated under reduced pressure to a yellow oil that was purified by HPLC, eluting with an MeCN/aq. NH₄OAc solution, to give 11.

Scheme 12: Synthesis of Example 12

Scheme 13: Synthesis of Example 13

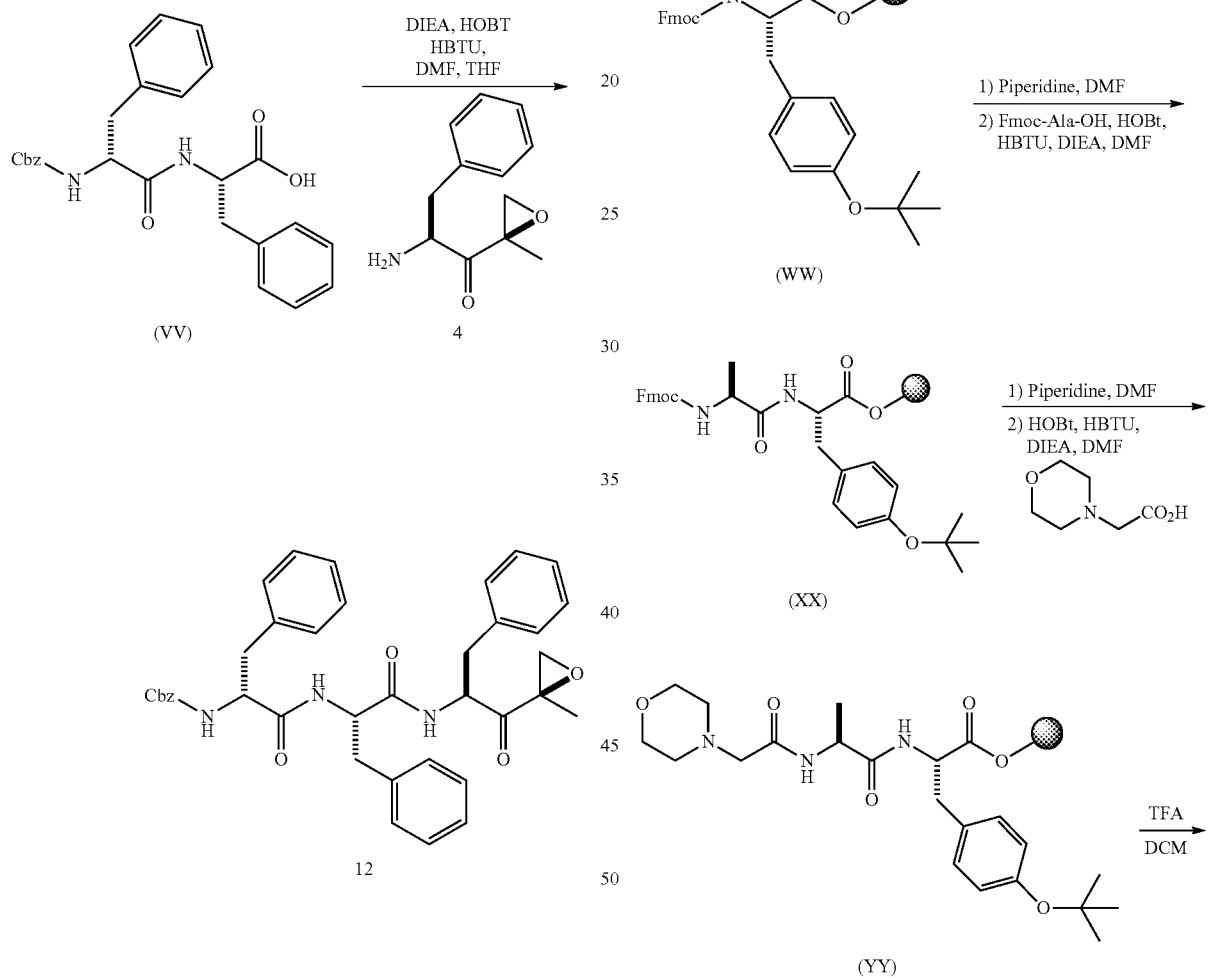

Synthesis of 12

To a 0° C. solution of (VV) (0.18 mmol, 50 mg) and 4 (0.12 mmol) in THF (5 mL) was added HOBT (0.18 mmol, 31 mg), HBTU (0.18 mmol, 76 mg) and DIEA (0.6 mmol, 0.1 mL). The resulting reaction mixture was stirred at 0-4° C. overnight followed by dilution with EtOAc (100 mL) and satd. NaHCO₃. The aqueous layer was then extracted with EtOAc, and the combined organic layers were dried over Na₂SO₄, filtered, and concentrated under reduced pressure to a yellow oil that was purified by HPLC, eluting with an MeCN/aq. NH₄OAc solution, to provide 12.

Synthesis of (WW)

To a solution of Fmoc-O-t-butyl-L-tyrosine (6.4 mmol, 2.94 g) in DCM (22 mL) was added 1-methylimidazole (4.8 mmol, 0.380 mL) and the mixture was stirred until the solution was homogenous, at which time 1-(mesitylene-2-sulfonyl)-3-nitro-1,2,4-triazole (MSNT) (6.4 mmol, 1.9 g) was added. Once the MSNT had dissolved, the reaction mixture was added to HMPB-BHA resin (1.28 mmol, 2 g) and the resulting mixture was allowed to shake for 45 minutes. The resin was filtered and washed with DMF (50 mL), MeOH (50 mL), and DCM (50 mL). The resin was then allowed to air dry to provide (WW).

Synthesis of (XX)

To (WW) (0.40 mmol, 0.62 g) was added 20% piperidine/DMF (50 mL) and the resulting mixture was allowed to shake for 20 minutes. The mixture was filtered and the resin was washed with DMF (20 mL), MeOH (20 mL), and DCM (20 mL) and allowed to air dry before subjecting it to the above reaction condition a second time.

To the resulting resin was added DMF (64 mL), Fmoc-Ala-OH (32 mmol, 1.05 g), DIEA (12.8 mmol, 2.2 mL), HOBT (5.12 mmol, 692 mg), and HBTU (5.12 mmol, 1.94 g) and the reaction mixture was allowed to shake for 45 minutes. The reaction mixture was filtered and the resin was washed with DMF (40 mL), DCM (40 mL), MeOH (40 mL), H$_2$O (40 mL) MeOH (40 mL), H$_2$O (40 mL), MeOH (40 mL), and DCM (40 mL), and allowed to air dry, to yield (XX).

Synthesis of (YY)

To (XX) (0.192 mmol, 0.3 g) was added 20% piperidine/DMF (10 mL) and the resulting mixture was allowed to shake for 20 minutes. The mixture was filtered and the resin was washed with DMF (20 mL), MeOH (20 mL), and DCM (20 mL) and allowed to air dry before subjecting it to the above reaction condition a second time.

To the resulting resin was added DMF (12 mL), morpholino acetic acid (0.48 mmol, 70 mg), DIEA (1.92 mmol, 334 µL), HOBT (0.768 mmol, 104 mg), and HBTU (0.768 mmol, 291 mg) and the reaction mixture was allowed to shake for 45 minutes. The reaction mixture was filtered and the resin was washed with DMF (40 mL), DCM (40 mL), MeOH (40 mL), H$_2$O (40 mL), MeOH (40 mL) H$_2$O (40 mL), MeOH (40 mL), and DCM (40 mL), and allowed to air dry, to yield (YY).

Synthesis of (ZZ)

To (YY) (0.192 mmol) was added 5% TFA/DCM (10 mL) and the mixture was allowed to shake for 10 minutes at 0° C. The reaction mixture was filtered and the resin was washed with DCM (10 mL). The volatiles were removed under reduced pressure and the resulting oil was diluted with DCM (10 mL) and evaporated a total of three times to yield (ZZ).

Synthesis of 13

To a stirred solution of (ZZ) (0.192 mmol, 83 mg) in MeCN (6 mL) and DMF (2 mL) was added 4 (0.384 mmol, 79 mg), DIEA (0.768 mmol, 133 µL), HOBT (0.3 mmol, 41 mg), and HBTU (0.3 mmol, 116 mg) and the mixture was stirred at 0° C. for 2 hours. The reaction was diluted with sat NaHCO$_3$ (15 mL) and extracted with EtOAc (3×). The organic layer was washed with sat. NaHCO$_3$ and brine, dried over MgSO$_4$, filtered, and concentrated under reduced pressure. The resulting crude material was purified by flash chromatography using EtOAc then EtOAc/MeOH/TEA (98/1/1) as the eluent to afford 13 as a white solid that was characterized by LC/MS (LCRS(MH) m/z: 623.80).

Scheme 14: Synthesis of Example 14

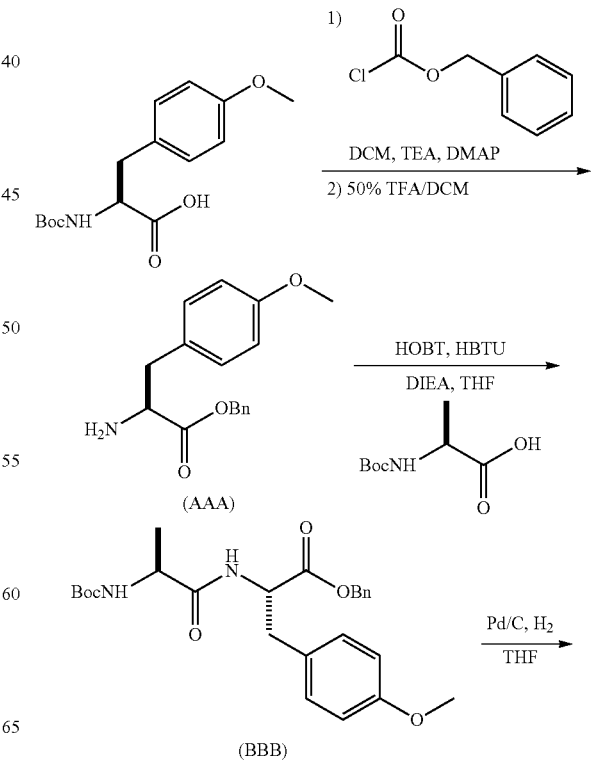

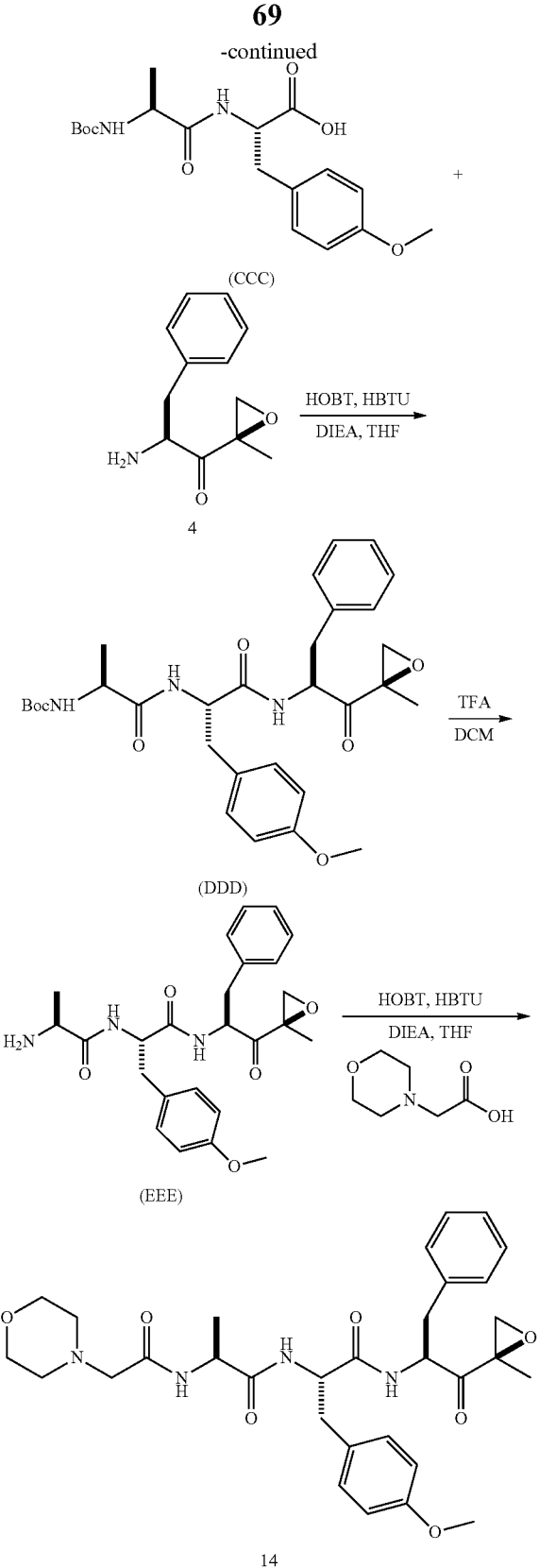

Synthesis of (AAA)

A suspension of Boc-Tyr(Me)—OH (10 g) in anhydrous dichlormethane (450 mL) was cooled to −5° C. in an ice/ acetone bath. To this suspension was added triethylamine (9.4 mL, 67.8 mmol) and DMAP (600 mg). A solution of benzylchloroformate (5.7 mL, 40.6 mmol) in dichloromethane (50 mL) was then added dropwise. The resulting solution was allowed to stir at −5° C. for three hours, and then allowed to warm to room temperature. A solution of saturated aqueous sodium bicarbonate (200 mL) was then added. The organic layer was separated and the aqueous layer was washed with dichloromethane (200 mL). The combined organic layers were washed with a saturated aqueous sodium bicarbonate solution, dried over sodium sulfate, filtered, and concentrated under reduced pressure. The resulting residue was purified by silica gel column chromatography using 80% hexanes/20% ethyl acetate to provide 11.43 g of a white solid. (88% yield) which was characterized by LC/MS (LCRS (MH) m/z: 386.42).

Boc-Tyr(Me)—OBn (2 g, 5.2 mmol) was dissolved in dichloromethane (15 mL) and cooled to 0° C. followed by dropwise addition of TFA (15 mL). The reaction was allowed to warm to room temp and was stirred for 2 hours. The solvents were removed under reduced pressure to yield (AAA) as a clear oil (1.4 g, 95% yield) which was characterized by LC/MS (LCRS(MH) m/z: 286.42) and was used without further purification.

Synthesis of (BBB)

To a 0° C. solution of Boc-Ala-OH (750 mg, 3.9 mmol), H-Tyr(Me)—OBn (950 mg, 3.3 mmol), HOBT (712 mg, 5.3 mmol) and HBTU (2.0 g, 5.3 mmol) in acetonitrile (60 mL) and DMF (6 mL) was added N,N-diisopropylethylamine (2.3 mL) dropwise. The mixture was stirred at 0° C. for 2 hours and was then diluted with ethyl acetate (300 mL) and washed with a saturated aqueous sodium bicarbonate solution (2×100 mL) and brine (100 mL). The organic layers were dried over sodium sulfate, filtered and concentrated under reduced pressure to yield an opaque oil that was purified by silica gel column chromatography using 50% hexanes/50% ethyl acetate to yield 600 mg of (BBB) as a white foam (40% yield) that was characterized by LC/MS (LCRS(MH) m/z: 457.52).

Synthesis of (CCC)

To a 0° C. solution of (BBB) (5.9 g, 12.9 mmol) in tetrahydrofuran (120 mL) was added 10% Pd/C (1.2 g) and the resulting mixture was allowed to stir under 1 atmosphere of hydrogen for 2 hours. The mixture was then filtered through Celite-545 and the filter cake was washed with tetrahydrofuran. The organic filtrate was then concentrated under reduced pressure and placed under high vacuum to provide 4.53 g (95% yield) of (CCC) that was used without further purification.

Synthesis of (DDD)

To a 0° C. solution of (CCC) (4 g, 10.9 mmol), 4 (2.23 g, 10.9 mmol), HOBT (2.36 g, 17.4 mmol) and HBTU (6.6 g, 17.4 mmol) in acetonitrile (200 mL) and DMF (5 mL) was added N,N-diisopropylethylamine (7.6 mL) and the mixture was stirred at 0° C. for 2 hours. It was then diluted with ethyl acetate (400 mL) and washed with saturated aqueous sodium bicarbonate (2×100 mL) and brine (100 mL). The organic layers were dried over sodium sulfate, filtered, and concentrated under reduced pressure. The resulting residue was purified by HPLC (aqueous ammonium acetate (0.02 M) and acetonitrile) to provide (DDD) (4.47 g, 74% yield) as characterized by LC/MS (LCRS(MH) m/z: 554.79).

Synthesis of (EEE)

To a 0° C. solution of (DDD) (2 g, 3.6 mmol) in dichloromethane (32 mL) was added trifluoroacetic acid (8 mL), and the resulting solution was stirred at that temperature for another hour. The solution was then concentrated under reduced pressure and placed under high vacuum to provide (EEE) as confirmed by LC/MS (LCRS(MH) m/z: 454.72) that was used without further purification.

Synthesis of 14

To a 0° C. solution of (EEE), morpholin-4-yl-acetic acid (1.048 g, 7.22 mmol), HOBT (780 mg, 5.76 mmol) and HBTU (2.2 g, 5.76 mmol) in acetonitrile (60 mL) and DMF (3 mL) was added N,N-diisopropylethylamine (2.5 mL) dropwise. The mixture was stirred at 0° C. for 2 hours and was then diluted with ethyl acetate (300 mL) and washed with saturated aqueous sodium bicarbonate (2×100 mL) and brine (100 mL). The organic layers were dried over sodium sulfate, filtered, and concentrated under reduced pressure. The resulting residue was purified by HPLC (aqueous ammonium acetate (0.02 M) and acetonitrile) to provide 14 (620 mg, 29% yield) which was characterized by LC/MS (LCRS(MH) m/z: 581.83).

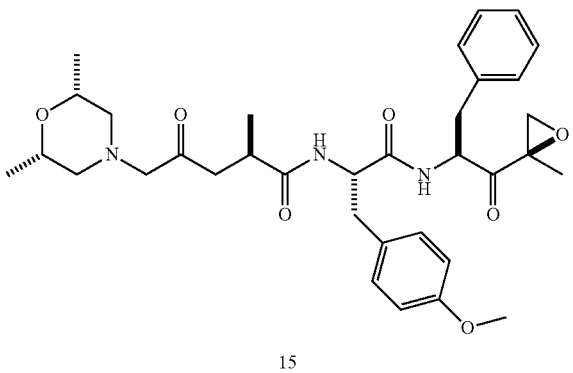

To a 0° C. solution of (EEE) (65 mg, 0.144 mmol), (2R, 6S)-2,6-dimethylmorpholin-4-yl)acetic acid hydrochloride (FFF) (50 mg, 0.288 mmol), HOBT (32 mg, 0.23 mmol) and HBTU (88 mg, 0.23 mmol) in acetonitrile (15 mL) and DMF (1 mL), was added N,N-diisopropylethylamine (100 μL) dropwise and the mixture was stirred at 0° C. for 2 hours. It was then diluted with ethyl acetate (30 mL) and washed with saturated aqueous sodium bicarbonate (2×15 mL) and brine (15 mL). The organic layers were dried over sodium sulfate, filtered, and concentrated under reduced pressure to give a residue that was purified by HPLC (aqueous ammonium acetate (0.02 M) and acetonitrile) to provide 15 (32 mg, 36% yield) as characterized by LC/MS (LCRS(MH) m/z: 609.83).

Scheme 15: Synthesis of Example 15

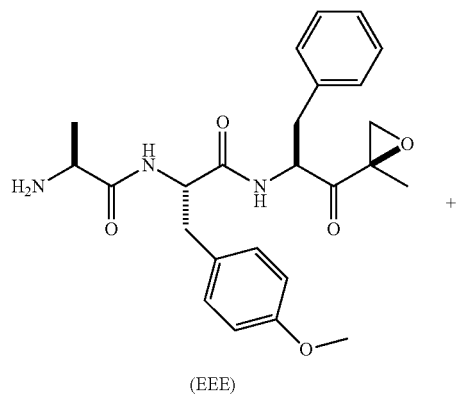

(EEE)

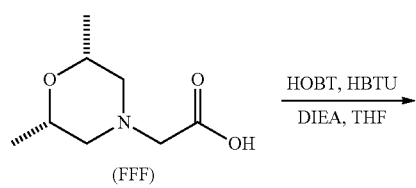

(FFF)

Scheme 16: Synthesis of Example 16

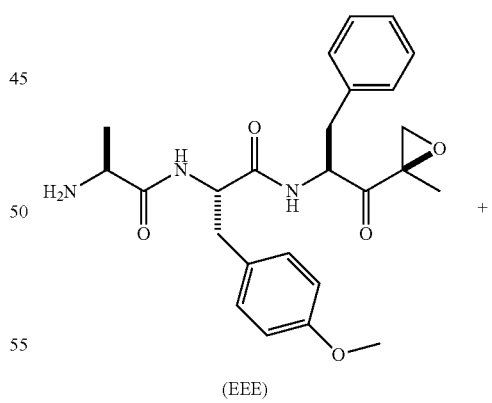

(EEE)

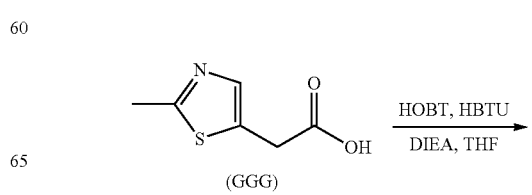

(GGG)

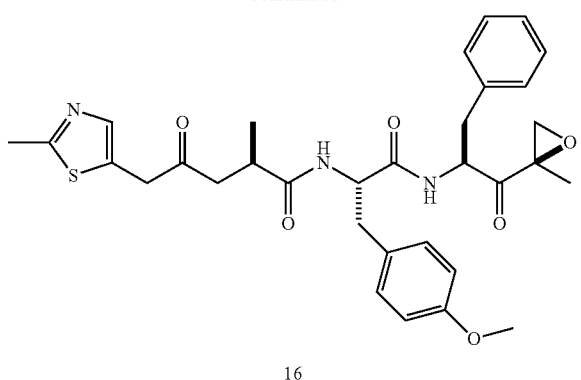

16

To a 0° C. solution of (EEE) (62 mg, 0.14 mmol), (2-methyl-1,3-thiazol-5-yl)acetic acid (GGG) (25 mg, 0.15 mmol), HOBT (30 mg, 0.22 mmol) and HBTU (84 mg, 0.22 mmol) in acetonitrile (15 mL) and DMF (1 mL) was added N,N-diisopropylethylamine (143 µL) dropwise and the resulting mixture was stirred at 0° C. for 2 hours. It was then diluted with ethyl acetate (30 mL) and washed with saturated aqueous sodium bicarbonate (2×15 mL) and brine (15 mL). The organic layers were dried over sodium sulfate, filtered, and concentrated under reduced pressure to give a residue that was purified by HPLC (aqueous ammonium acetate (0.02 M) and acetonitrile) to provide 16 that was characterized by LC/MS (LCRS(MH) m/z: 593.72).

Scheme 17: Synthesis of Example 17

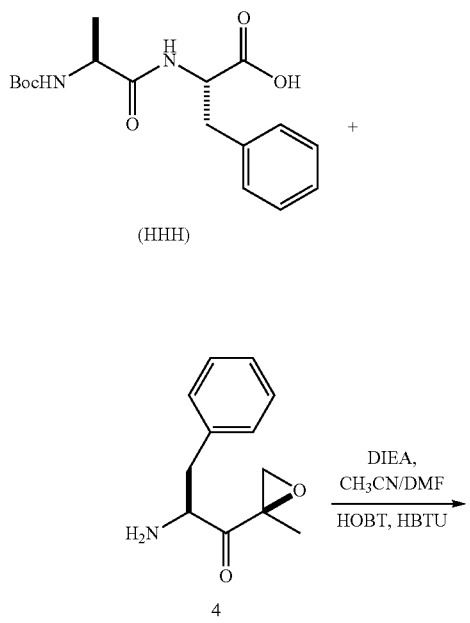

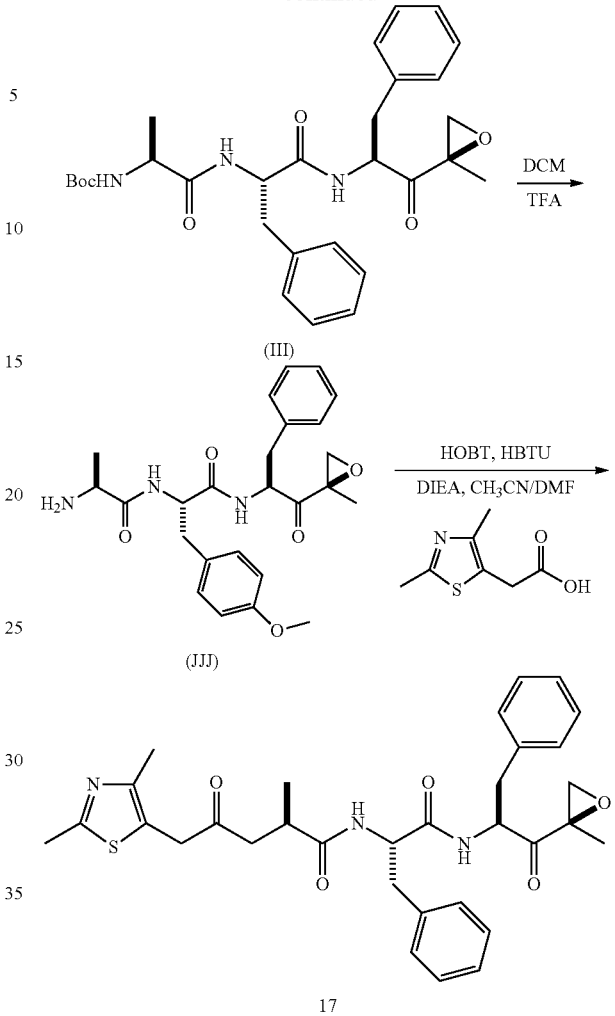

Synthesis of (III)

To a 0° C. solution of (HHH) (2 g, 5.9 mmol), 4 (2.44 g, 11.89 mmol), HOBT (1.28 g, 9.5 mmol) and HBTU (3.6 g, 9.5 mmol) in acetonitrile (180 mL) and DMF (10 mL) was added N,N-diisopropylethylamine (4.14 mL) dropwise and the mixture was stirred at 0° C. for 2 hours. It was then diluted with ethyl acetate (200 mL) and washed with a saturated aqueous sodium bicarbonate solution (2×50 mL) and brine (50 mL). The combined organic layers were dried over sodium sulfate, filtered, and concentrated under reduced pressure to give a residue that was purified by HPLC (aqueous ammonium acetate (0.02 M) and acetonitrile) to provide (III) (1.5 g, 50% yield) as characterized by LC/MS (LCRS(MH) m/z: 524.71).

Synthesis of (JJJ)

To a 0° C. solution of (III) (60 mg, 0.1 mmol) in dichloromethane (2 mL) was added trifluoroacetic acid (0.5 mL), and the resulting solution was stirred at that temperature for another hour. The solution was then concentrated under reduced pressure and placed under high vacuum to provide (JJJ) as confirmed by LC/MS (LCRS(MH) m/z: 424.51) that was used without further purification.

Synthesis of 17

To a 0° C. solution of (JJJ), (2,4-dimethyl-1,3-thiazol-5-yl-acetic acid (40 mg, 0.23 mmol), HOBT (25 mg, 0.183 mmol) and HBTU (70 mg, 0.183 mmol) in acetonitrile (6 mL) and DMF (1 mL) was added N,N-diisopropylethylamine (80 µL) dropwise. The mixture was then stirred at 0° C. for 2 hours. It was then diluted with ethyl acetate (50 mL) and washed with saturated aqueous sodium bicarbonate (2×10 mL) and brine (10 mL). The combined organic layers were dried over sodium sulfate, filtered, and concentrated under reduced pressure to give a residue that was purified by HPLC (aqueous ammonium acetate (0.02 M) and acetonitrile) to provide 17 (29 mg, 44% yield) which was characterized by LC/MS (LCRS(MH) m/z: 577.86).

Example 18

Assays to Determine Inhibitory Preference

There are three types of assays that can be utilized when determining whether or not a molecule preferentially inhibits the CT-L activity of the constitutive or immunoproteasome. Enzyme kinetic assays such as those disclosed in U.S. application Ser. No. 09/569,748, Example 2 and Stein et al., Biochem. (1996), 35, 3899-3908 use isolated 20S proteasome preps with greater than 90% constitutive proteasome subunits or immunoproteasome subunits. The inhibitory preference of the molecule is then based on the $EC_{50}$ ratio of the chymotryptic-like activity of the constitutive proteasome to that of the immunoproteasome (20S ratio).

Alternatively, the CT-L $EC_{50}$ of a compound can be determined using 26S proteasome in the context of a cell lysate. Compound is added to lysate generated from cells that either predominantly express constitutive proteasome (e.g., HT29) or immunoproteasome (e.g., THP1). Again, the inhibitory preference is then based on the $EC_{50}$ ratio (Lysate ratio).

Lastly, a more cell-based approach can be utilized. Cells expressing approximately equivalent amounts of immuno- and constitutive proteasome (e.g., RPMI-8226) are treated with test compound, followed by the method for determining the activity of a proteasome inhibitor as described in application Ser. No. 11/254,541. The ratio of the $EC_{50}$ generated in the ELISA-based assay using β5 antibody and LMP7 antibodies (ELISA ratio) provides the basis for determining the inhibitory preference of the test compound. In all instances, a ratio of one indicates that the molecule works equally well at inhibiting the CT-L activity of both forms of proteasome. In all three assays, a ratio of less than one denotes the molecule inhibits the CT-L activity of the constitutive proteasome better than that of the immunoproteasome. Ratios greater than one signifies the molecule inhibits chymotrypsin-like activity of the immunoproteasome better than that of the constitutive proteasome.

Example 19

ELISA Assay

A suitable ELISA assay may be found in U.S. patent application Ser. No. 11/254,541, incorporated herein in its entirety. Briefly, RPMI-8226 cells were treated with 0.1 nM to 1 µM of proteasome Inhibitor B. The samples were then washed with phosphate-buffered saline (PBS) and lysed in hypotonic buffer (20 mM Tris pH 8, 5 mM EDTA) (Tris-HCl and EDTA are available from Teknova, Inc., Hollister, Calif.). Cellular debris was removed by centrifugation at 14,000 rpm in a microfuge (4° C.) for 2 min. The supernatant was transferred to a fresh tube, snap frozen in liquid nitrogen and stored at −80° C. After thawing on ice, the samples (30 µl for assays run in triplicate) were treated with 500 nM of Inhibitor A for 1 hr at room temperature. Following treatment with Inhibitor A, the lysate was denatured by addition of seven volumes of 1% SDS (210 µl) (available from Bio-Rad, Hercules, Calif.) and heating at 99° C. with vigorous shaking for 5 min. The sample was allowed to cool and two volumes (60 µl) of 10% Triton X-100 (available from Bio-Rad, Hercules, Calif.) was added.

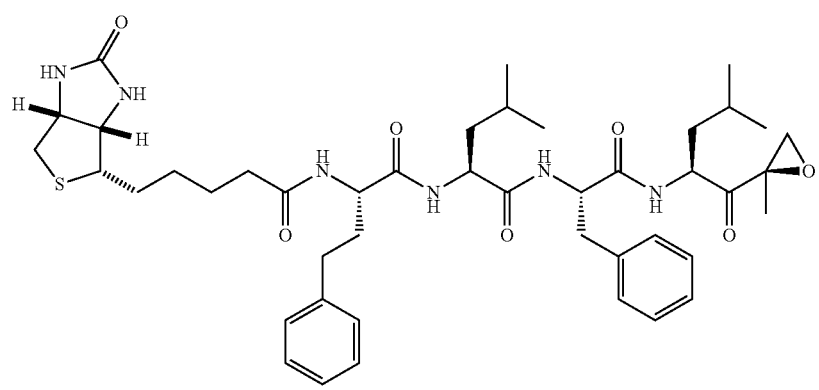

Inhibitor A

-continued

Inhibitor B

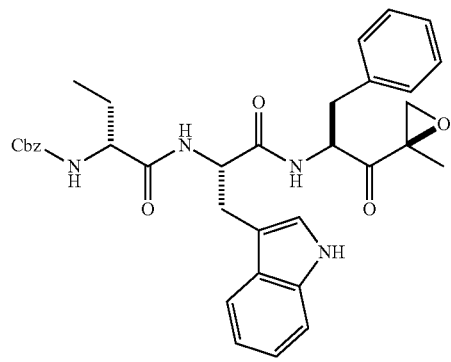

Streptavidin sepharose beads (6.5 μl/well) (available from Amersham Biosciences, Piscataway, N.J.), were washed three times with 1 ml PBS (available from Mediatech, Inc., Herndon, Va.) in a microcentrifuge tube. The beads were resuspended in ELISA wash/block buffer (PBS+0.1% Tween 20+1% bovine serum albumin; 20 μl/well) and transferred to the wells of a 96 well filter plate (BSA is available from Sigma, St. Louis, Mo.; Tween is available from Calbiochem, San Diego, Calif.). Denatured whole blood or PBMC lysates that were treated with Inhibitor 3 were added to the filter plate wells containing the streptavidin sepharose beads (each sample assayed in triplicate) and incubated for 1 hr at room temperature with shaking (MultiScreen-DV Opaque Plates with low protein binding durapore membrane; available from Millipore, Billerica, Mass.). The unbound material was removed by gentle filtration and the beads were washed six times with ELISA wash/block buffer (200 μl each).

Primary antibody to human 20S proteasome subunit (35 (rabbit polyclonal antibody; available from Biomol, Plymouth Meeting, Pa.) or human 20S immunoproteasome subunit LMP7 (rabbit polyclonal antibody; available from Affinity BioReagents, Golden, Colo.) was diluted 1:1000 in ELISA wash/block buffer, added to the beads (100 μl/well), and incubated for 1 hr at room temperature on an orbital shaker. The beads were washed six times with ELISA wash/block buffer with gentle filtration. Secondary antibody treatment (1:5000) and washing are as described for primary antibody (goat anti-rabbit antibody-HRP conjugate; available from Biosource, Camarillo, Calif.). The beads were then resuspended in 100 μl chemiluminescent detection reagent (Super Signal Pico Chemiluminescent Substrate™; available from Pierce, Rockford, Ill.) and luminescence was read on a Tecan plate reader.

Occupation of the active sites of the proteasome with the peptide epoxyketone inhibitor results in both a decrease in chymotryptic-like catalytic activity and a decrease in binding of the biotinylated probe (Inhibitor A). These data suggest that the ELISA-based assay using the biontinylated probe accurately reflects the inhibitory activity of Inhibitor B.

An exemplary feature of the ELISA-based PD assay is that it permits differentiation between constitutive proteasome inhibition (β5) and immunoproteasome inhibition (LMP7) because it utilizes subunit-specific antibodies.

Utilizing a different active site probe (Inhibitor C) expands the utility of the ELISA-based assay for measuring the occupation of multiple constitutive (β5, β1, β2) and immunoproteasome (LMP7, LMP2) active sites in 8226 multiple myeloma cell line that co-expresses both forms of proteasome. The expanded active site assay can be used to measure relative inhibitor selectivity both between the immuno- and constitutive proteasomes as well as among the three active sites of each proteasome. In addition, the ELISA-based assay is able to determine the potency and selectivity of other classes of proteasome inhibitors, including the peptide boronic acid-based inhibitors.

Inhibitor C

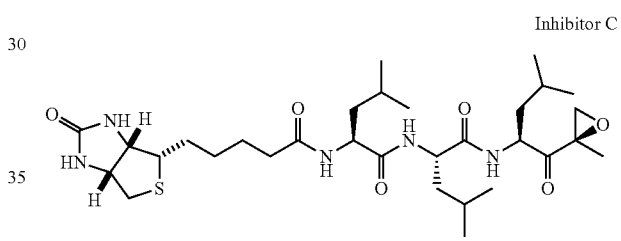

To conduct a pharmacodynamic evaluation of an inhibitor, whole blood and PBMC samples are collected prior to dosing and at multiple time-points after dosing. Lysates are prepared and protein concentration assays performed to normalize for total protein in each lysate. The level of inhibitor binding to β5 and LMP7 subunits in whole blood and PBMCRPMI-8226 cells, respectively, is determined by the streptavidin-capture ELISA described above. Standard curves with purified constitutive proteasome and immunoproteasome are utilized to ensure assay linearity/dynamic range and to convert the chemiluminescence signal to an absolute amount (μg) of subunit bound. The ratio of the EC50 generated in the ELISA-based assay using β5 antibody and LMP7 antibodies (ELISA ratio) provides the basis for determining the inhibitory preference of the test compound. The above inhibitor (B) has a ratio greater than 20, thus, it is much more selective at inhibiting the chymotryptic-like activity associated with the immunoproteasome.

To determine the level of proteasome inhibition for a given patient, the amount of β5 or LMP7 detected in the post-dose sample is compared to the pre-dose sample. Proteasome inhibition is determined after a single dose or after a cycle of dosing, or is used to monitor inhibition shortly after dosing as well as to monitor recovery of proteasome activity after a course of dosing.

Example 20

Biological Results

| Structure | 20S ratio (const: immuno) | Lysate ratio (HT29: Sultan/Thp1) | Elisa ratio (beta5:LMP7) |
|---|---|---|---|
| Cbz-Gln-Trp-Phe-epoxyketone | >1.0 | >3.0 | >1.0 |
| Cbz-Glu-Trp-Phe-epoxyketone | >2.0 | >2.0 | >3.0 |
| Cbz-His-Phe-Phe-epoxyketone | <1.0 | <1.0 | <1.0 |
| Cbz-Gln-Phe-Phe-epoxyketone | >2.0 | >3.0 | >5.0 |

-continued
| Structure | 20S ratio (const: immuno) | Lysate ratio (HT29: Sultan/Thp1) | Elisa ratio (beta5:LMP7) |
|---|---|---|---|
| 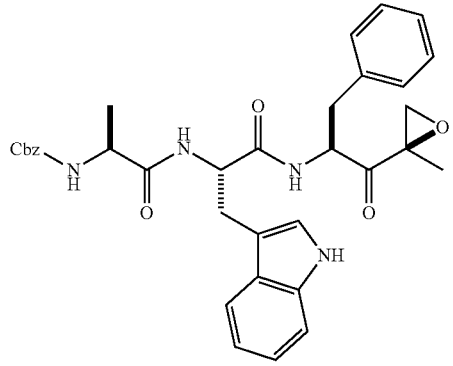 [SMILES: C[C@H](NC(=O)OCc1ccccc1)C(=O)N[C@@H](Cc1c[nH]c2ccccc12)C(=O)N[C@@H](Cc1ccccc1)C(=O)[C@@]1(C)CO1] | >1.0 | >2.0 | >5.0 |
| 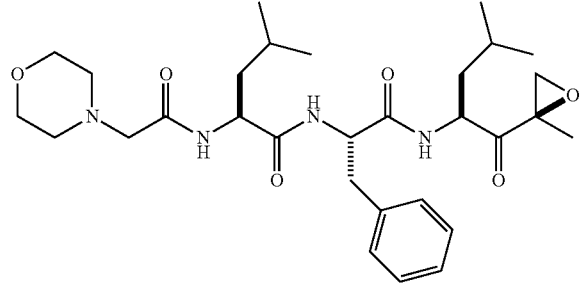 [SMILES: CC(C)C[C@H](NC(=O)CN1CCOCC1)C(=O)N[C@@H](Cc1ccccc1)C(=O)N[C@@H](CC(C)C)C(=O)[C@@]1(C)CO1] | <0.5 | <0.5 | <0.5 |
| 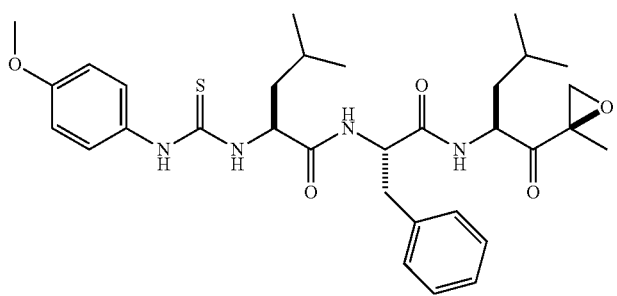 [SMILES: COc1ccc(NC(=S)N[C@@H](CC(C)C)C(=O)N[C@@H](Cc2ccccc2)C(=O)N[C@@H](CC(C)C)C(=O)[C@@]2(C)CO2)cc1] | | <0.5 | |
| 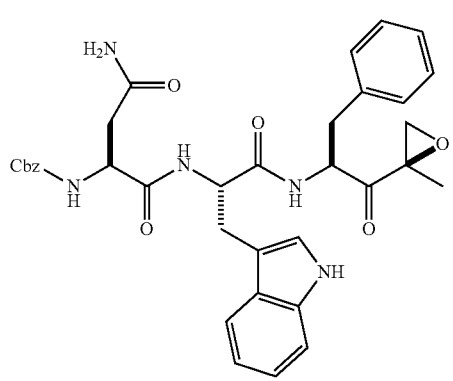 [SMILES: C[C@]1(C(=O)[C@H](Cc2ccccc2)NC(=O)[C@H](Cc2c[nH]c3ccccc23)NC(=O)[C@H](CC(N)=O)NC(=O)OCc2ccccc2)CO1] | >1.0 | >5.0 | >1.0 |

-continued
| Structure | 20S ratio (const: immuno) | Lysate ratio (HT29: Sultan/Thp1) | Elisa ratio (beta5:LMP7) |
|---|---|---|---|
| 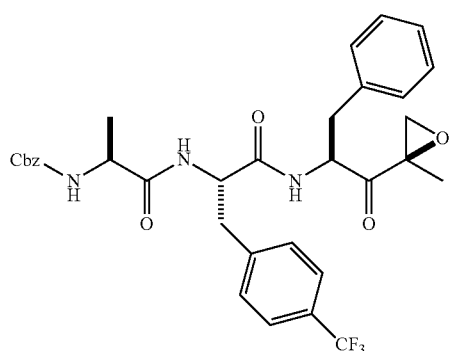 | >1.0 | >3.0 | >2.0 |
| 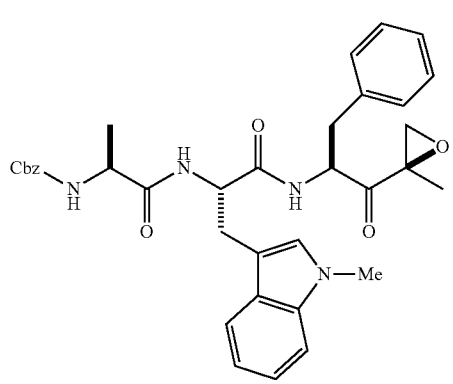 [SMILES: C[C@H](NC(=O)OCc1ccccc1)C(=O)N[C@@H](Cc1cn(C)c2ccccc12)C(=O)N[C@@H](Cc1ccccc1)C(=O)[C@@]1(C)CO1] | >1.0 | >1.0 | >3.0 |
| 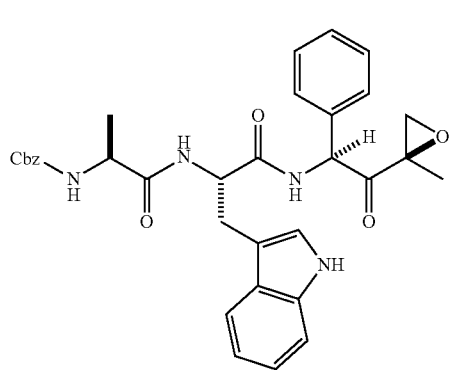 [SMILES: C[C@H](NC(=O)OCc1ccccc1)C(=O)N[C@@H](Cc1c[nH]c2ccccc12)C(=O)N[C@H](C(=O)[C@@]1(C)CO1)c1ccccc1] | >2.0 | >5.0 | >3.0 |
| 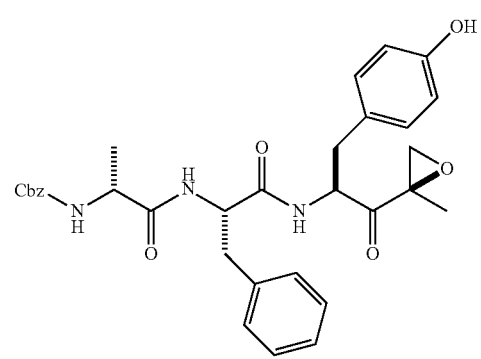 [SMILES: C[C@@H](NC(=O)OCc1ccccc1)C(=O)N[C@@H](Cc1ccccc1)C(=O)N[C@@H](Cc1ccc(O)cc1)C(=O)[C@@]1(C)CO1] | >5.0 | >3.0 | >3.0 |

| Structure | 20S ratio (const: immuno) | Lysate ratio (HT29: Sultan/Thp1) | Elisa ratio (beta5:LMP7) |
| --- | --- | --- | --- |
| Cbz-Leu-Leu-Phe-epoxyketone | <0.5 | <1.0 | <0.5 |
| Cbz-Gly-Phe-Phe-epoxyketone | >3.0 | >5.0 | >2.0 |
| Cbz-Ile-Phe-Phe-epoxyketone | >5.0 | >3.0 | >2.0 |
| Cbz-Abu-Phe-Phe-epoxyketone | >5.0 | >5.0 | >3.0 |
| PhNHC(O)NH-Leu-Phe-Leu-epoxyketone | | | <5.0 |

-continued

| Structure | 20S ratio (const: immuno) | Lysate ratio (HT29: Sultan/Thp1) | Elisa ratio (beta5:LMP7) |
|---|---|---|---|
| 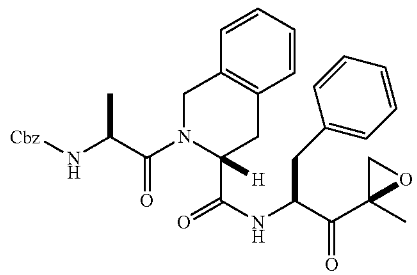 [SMILES: C[C@H](NC(=O)OCc1ccccc1)C(=O)N1Cc2ccccc2C[C@@H]1C(=O)N[C@@H](Cc1ccccc1)C(=O)[C@@]1(C)CO1] | <1.0 | <1.0 | <0.5 |
| 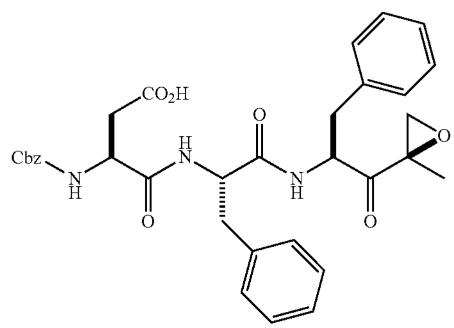 [SMILES: C[C@]1(C(=O)[C@H](Cc2ccccc2)NC(=O)[C@H](Cc2ccccc2)NC(=O)[C@H](CC(=O)O)NC(=O)OCc2ccccc2)CO1] | >3.0 | >3.0 | >2.0 |
| | >5.0 | >2.0 | >5.0 |
| | >5.0 | >3.0 | >5.0 |

-continued

| Structure | 20S ratio (const: immuno) | Lysate ratio (HT29: Sultan/Thp1) | Elisa ratio (beta5:LMP7) |
|---|---|---|---|
| [Cbz-Ala-Tyr(OMe-Bn)-Tyr-epoxyketone structure] | >5.0 | >3.0 | >5.0 |
| [Cbz-Ala-Phe-Ala-epoxyketone structure] | <0.5 | <0.5 | <0.5 |
| [Cbz-Ala-Phe-Leu-epoxyketone structure] | <0.5 | <0.5 | <1.0 |
| [Cbz-Ala-Trp-Ala-epoxyketone structure] | <0.5 | | |
| [Cbz-Ala-Trp-Leu-epoxyketone structure] | <0.5 | | |

-continued
| Structure | 20S ratio (const: immuno) | Lysate ratio (HT29: Sultan/Thp1) | Elisa ratio (beta5:LMP7) |
|---|---|---|---|
| 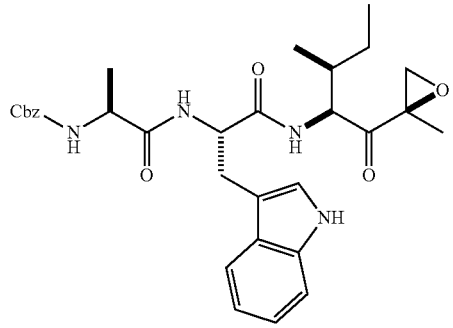 | <0.5 | <0.5 | <1.0 |
| 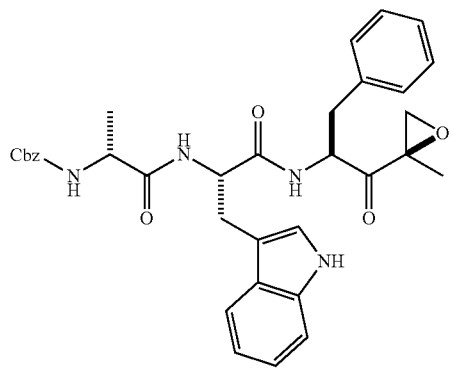 [SMILES: C[C@@H](NC(=O)OCc1ccccc1)C(=O)N[C@@H](Cc1c[nH]c2ccccc12)C(=O)N[C@@H](Cc1ccccc1)C(=O)[C@@]1(C)CO1] | >5.0 | >5.0 | >5.0 |
| 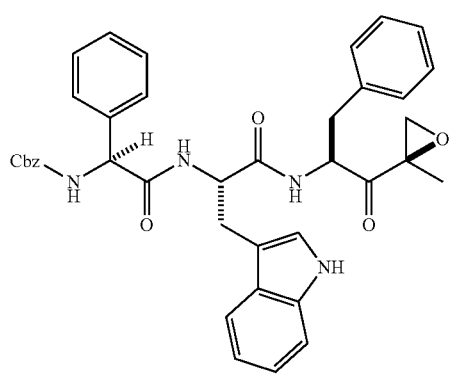 [SMILES: C[C@]1(C(=O)[C@H](Cc2ccccc2)NC(=O)[C@H](Cc2c[nH]c3ccccc23)NC(=O)[C@@H](NC(=O)OCc2ccccc2)c2ccccc2)CO1] | >3.0 | >3.0 | >1.0 |
| 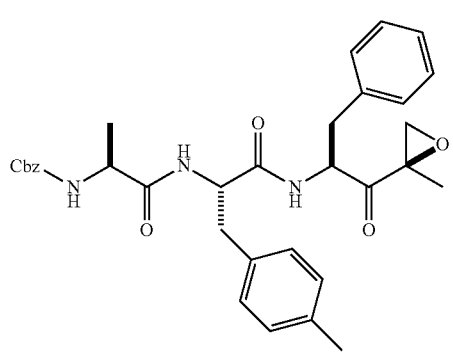 [SMILES: Cc1ccc(C[C@H](NC(=O)[C@H](C)NC(=O)OCc2ccccc2)C(=O)N[C@@H](Cc2ccccc2)C(=O)[C@@]2(C)CO2)cc1] | >2.0 | >5.0 | >5.0 |

-continued
| Structure | 20S ratio (const: immuno) | Lysate ratio (HT29: Sultan/Thp1) | Elisa ratio (beta5:LMP7) |
|---|---|---|---|
| 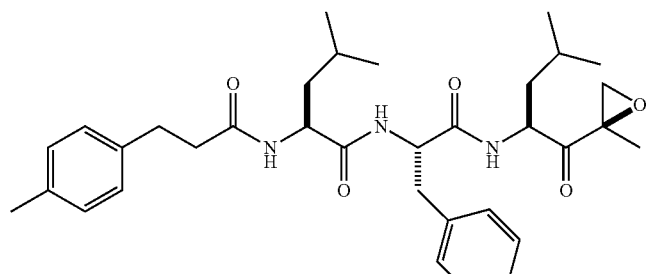 | | <0.5 | |
| 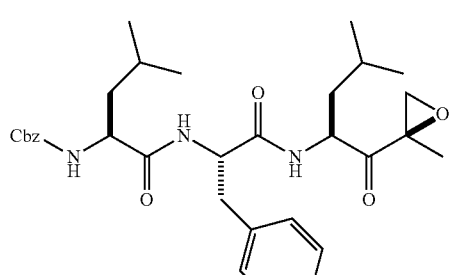 | <0.5 | <0.5 | <0.5 |
| 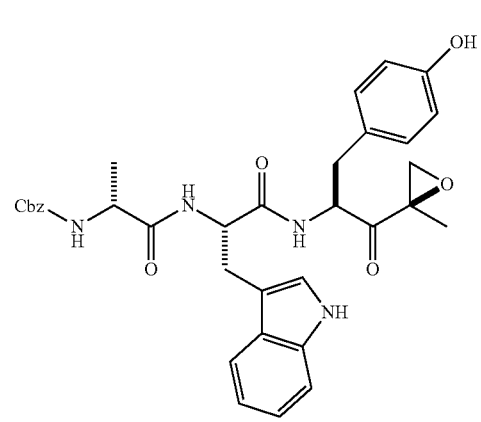 [SMILES: C[C@@H](NC(=O)OCc1ccccc1)C(=O)N[C@@H](Cc1c[nH]c2ccccc12)C(=O)N[C@@H](Cc1ccc(O)cc1)C(=O)[C@@]1(C)CO1] | >5.0 | >5.0 | >3.0 |
| 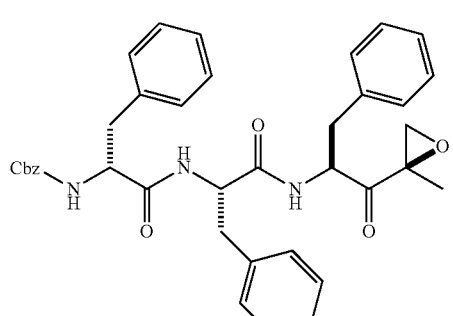 | >5.0 | >2.0 | >3.0 |

-continued
| Structure | 20S ratio (const: immuno) | Lysate ratio (HT29: Sultan/Thp1) | Elisa ratio (beta5:LMP7) |
|---|---|---|---|
| 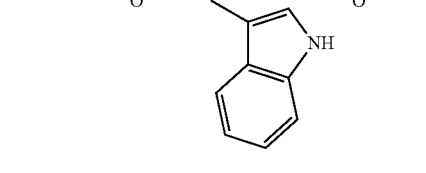 | >5.0 | >3.0 | >5.0 |
| 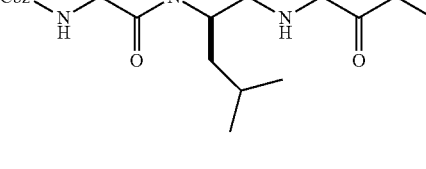 | <0.5 | <0.5 | <0.5 |
| 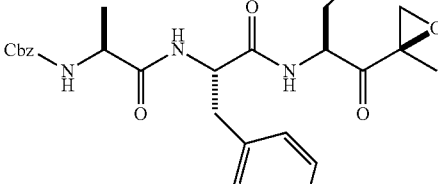 | >1.0 | >2.0 | >5.0 |
| 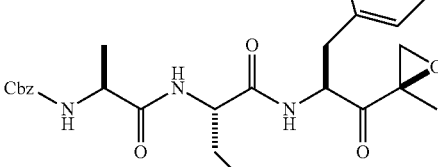 | >2.0 | >2.0 | >3.0 |

-continued

| Structure | 20S ratio (const: immuno) | Lysate ratio (HT29: Sultan/Thp1) | Elisa ratio (beta5:LMP7) |
|---|---|---|---|
| | >5.0 | >3.0 | >5.0 |
| | >5.0 | >5.0 | >5.0 |
| 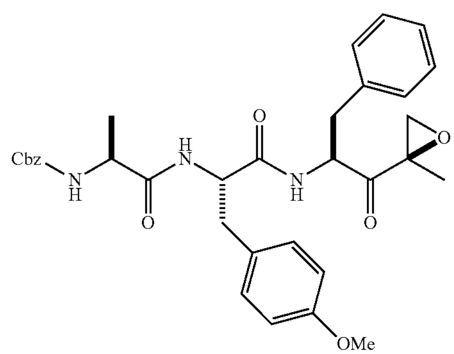 [SMILES: COc1ccc(C[C@H](NC(=O)[C@H](C)NC(=O)OCc2ccccc2)C(=O)N[C@@H](Cc2ccccc2)C(=O)[C@@]2(C)CO2)cc1] | >2.0 | >2.0 | >5.0 |
| | | | <1.0 |

-continued
| Structure | 20S ratio (const: immuno) | Lysate ratio (HT29: Sultan/Thp1) | Elisa ratio (beta5:LMP7) |
|---|---|---|---|
| 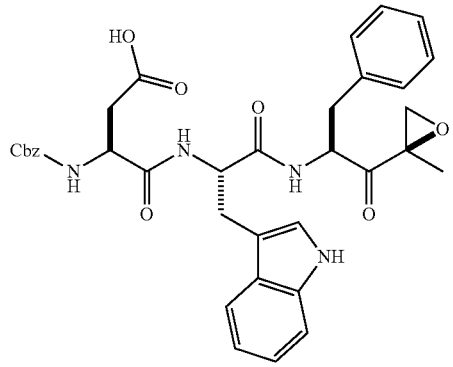 [SMILES: C[C@]1(C(=O)[C@H](Cc2ccccc2)NC(=O)[C@H](Cc2c[nH]c3ccccc23)NC(=O)[C@H](CC(=O)O)NC(=O)OCc2ccccc2)CO1] | >3.0 | >3.0 | >2.0 |
| 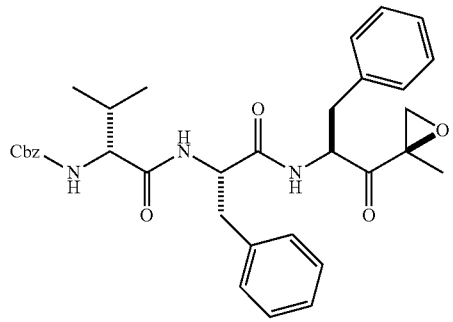 [SMILES: CC(C)[C@@H](NC(=O)OCc1ccccc1)C(=O)N[C@@H](Cc1ccccc1)C(=O)N[C@@H](Cc1ccccc1)C(=O)[C@@]1(C)CO1] | >5.0 | >2.0 | >2.0 |
| 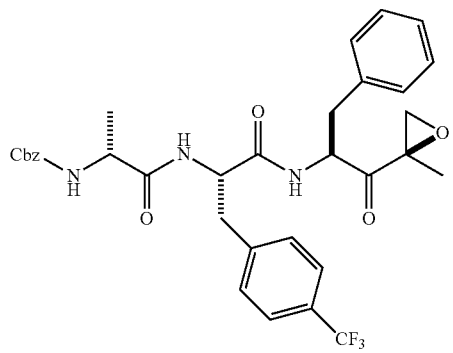 [SMILES: C[C@@H](NC(=O)OCc1ccccc1)C(=O)N[C@@H](Cc1ccc(C(F)(F)F)cc1)C(=O)N[C@@H](Cc1ccccc1)C(=O)[C@@]1(C)CO1] | >5.0 | >2.0 | >1.0 |
| 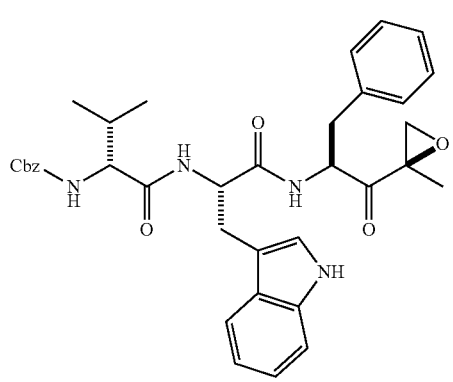 [SMILES: CC(C)[C@@H](NC(=O)OCc1ccccc1)C(=O)N[C@@H](Cc1c[nH]c2ccccc12)C(=O)N[C@@H](Cc1ccccc1)C(=O)[C@@]1(C)CO1] | >5.0 | >5.0 | >5.0 |

-continued

| Structure | 20S ratio (const: immuno) | Lysate ratio (HT29: Sultan/Thp1) | Elisa ratio (beta5:LMP7) |
|---|---|---|---|
| | | <0.5 | |
| 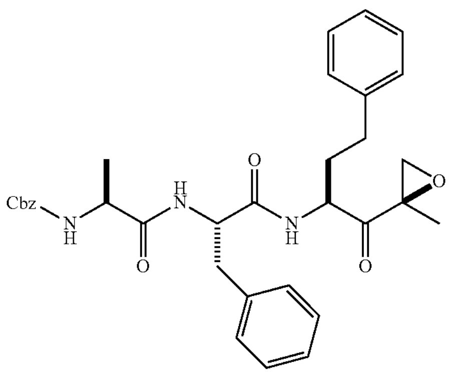 [SMILES: C[C@H](NC(=O)OCc1ccccc1)C(=O)N[C@@H](Cc1ccccc1)C(=O)N[C@@H](CCc1ccccc1)C(=O)[C@@]1(C)CO1] | >2.0 | >3.0 | >3.0 |
| | >1.0 | >5.0 | >1.0 |
| | >1.0 | >2.0 | >5.0 |

-continued
| Structure | 20S ratio (const: immuno) | Lysate ratio (HT29: Sultan/Thp1) | Elisa ratio (beta5:LMP7) |
|---|---|---|---|
| 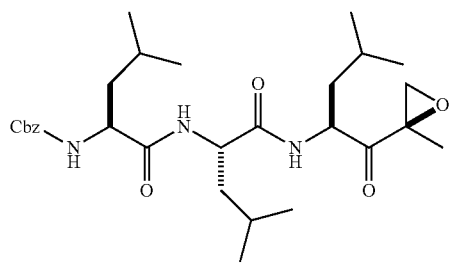 [SMILES: CC(C)C[C@H](NC(=O)OCc1ccccc1)C(=O)N[C@@H](CC(C)C)C(=O)N[C@@H](CC(C)C)C(=O)[C@@]1(C)CO1] | <0.5 | <0.5 | <0.5 |
| 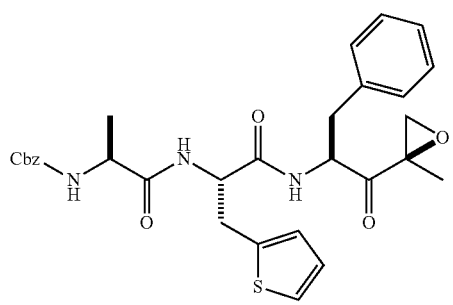 [SMILES: C[C@H](NC(=O)OCc1ccccc1)C(=O)N[C@@H](Cc1cccs1)C(=O)N[C@@H](Cc1ccccc1)C(=O)[C@@]1(C)CO1] | >2.0 | >2.0 | >3.0 |
| 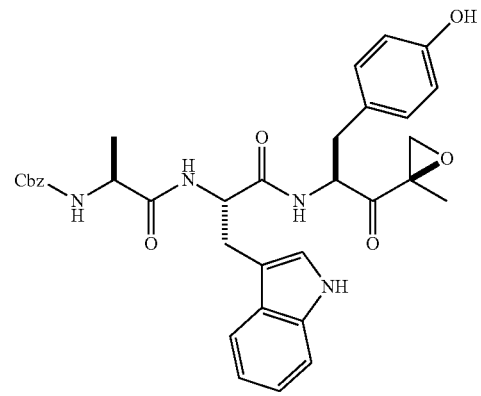 [SMILES: C[C@H](NC(=O)OCc1ccccc1)C(=O)N[C@@H](Cc1c[nH]c2ccccc12)C(=O)N[C@@H](Cc1ccc(O)cc1)C(=O)[C@@]1(C)CO1] | >3.0 | >3.0 | >5.0 |
| 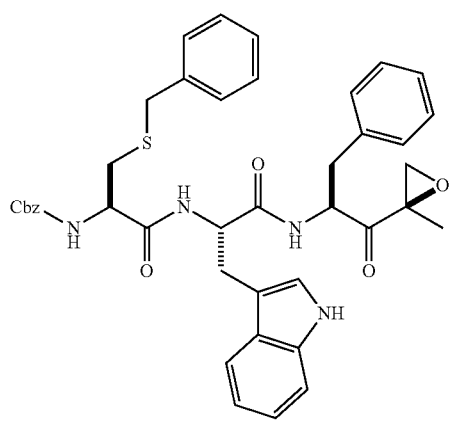 [SMILES: C[C@]1(C(=O)[C@H](Cc2ccccc2)NC(=O)[C@H](Cc2c[nH]c3ccccc23)NC(=O)[C@H](CSCc2ccccc2)NC(=O)OCc2ccccc2)CO1] | >2.0 | >3.0 | >1.0 |

| Structure | 20S ratio (const: immuno) | Lysate ratio (HT29: Sultan/Thp1) | Elisa ratio (beta5:LMP7) |
|---|---|---|---|
| 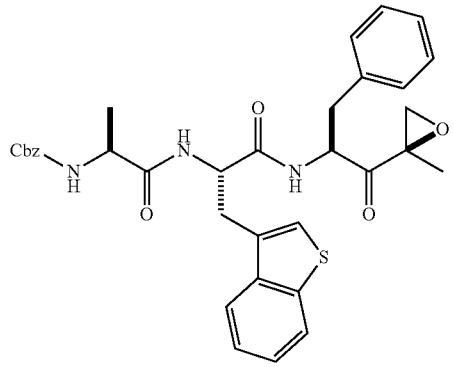 [SMILES: C[C@H](NC(=O)OCc1ccccc1)C(=O)N[C@@H](Cc1csc2ccccc12)C(=O)N[C@@H](Cc1ccccc1)C(=O)[C@@]1(C)CO1] | >1.0 | >1.0 | >3.0 |

Example 21

Use of Immunoproteasome Inhibitor in Rheumatoid Arthritis Model

The effect of Compound 14 on disease progression was assessed in 2 mouse models of rheumatoid arthritis (FIG. 2). In the arthrogenic antibody model, in which disease is induced by the administration of anti-collagen antibodies and lipopolysaccharide (LPS) (Terato et al., J Immunol 148:2103-2108, 1992), Compound 14 inhibited disease progression in a dose dependent manner (FIG. 2A). Rhematoid arthritis was induced on Day 0 in female Balb/c mice by IV administration of anti-type II collagen antibodies followed 3 days later by LPS. Compound X was administered IV 3 times/week for 2 weeks beginning on Day 4, the first day animals showed evidence of disease. Per mouse, each paw was measured for disease using a scale of 0-4 and a total clinical score was assigned for each animal (max score=16). Administration of 6 mg/kg of Compound 14 reduced disease severity by ~50% while the 20 mg/kg dose level inhibited the disease by greater than 75%.

The effect administration of Compound 14 on disease progress was also assessed in an alternative mouse model for RA, in which disease develops 21-30 days after immunization with bovine type II collagen (Kagari et al., J Immunol 169:1459-1466, 2002). Administration of 6 or 20 mg/kg Compound 14 beginning after first signs of disease inhibited disease progression as compared to vehicle control (FIG. 2 B). Again, disease progression was measured using a total clinical score of paw condition per mouse. As seen previously, increasing amounts of Compound 14 resulted in enhanced reduction of disease severity.

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims.

All of the above-cited references and publications are hereby incorporated by reference.

We claim:

1. A compound having a structure of formula (I) or a pharmaceutically acceptable salt thereof,

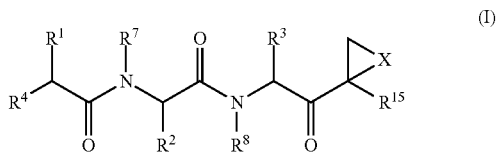

wherein
each A is independently selected from C=O, C=S, and SO$_2$; or
A is optionally a covalent bond when adjacent to an occurrence of Z;
B is absent or is N(R$^9$)R$^{10}$;
L is absent or is selected from C=O, C=S, and SO$_2$;
M is C$_{1-12}$alkyl;
Q is absent or is selected from O, NH, and N—C$_{1-6}$alkyl;
X is selected from O, S, NH, and N—C$_{1-6}$alkyl;
each Z is independently selected from O, S, NH, and N—C$_{1-6}$alkyl; or
Z is optionally a covalent bond when adjacent to an occurrence of A;
R$^1$ is selected from H, —C$_{1-6}$alkyl-B, C$_{1-6}$hydroxyalkyl, C$_{1-6}$alkoxyalkyl, aryl, and C$_{1-6}$aralkyl;
R$^2$ and R$^3$ are each independently selected from aryl, C$_{1-6}$aralkyl, heteroaryl, and C$_{1-6}$heteroaralkyl;
R$^4$ is N(R$^5$)L-Q-R$^6$;
R$^5$ is selected from hydrogen, OH, aryl C$_{1-6}$alkyl, and C$_{1-6}$alkyl;
R$^6$ is selected from an N-terminal protecting group, heterocyclylMZAZC$_{1-6}$alkyl-, heterocyclylM-, and carbocyclylM;
R$^7$ and R$^8$ are independently selected from hydrogen, C$_{1-6}$alkyl, and C$_{1-6}$aralkyl;
R$^9$ is selected from hydrogen, OH, and C$_{1-6}$alkyl; and
R$^{10}$ is an N-terminal protecting group; and
R$^{15}$ is selected from C$_{1-6}$alkyl and C$_{1-6}$hydroxyalkyl;
provided that in any occurrence of the sequence ZAZ, at least one member of the sequence must be other than a covalent bond.

2. The compound of claim 1, wherein $R^7$ and $R^8$ are independently selected from hydrogen and $C_{1-6}$aralkyl.

3. The compound of claim 2, wherein $R^7$ and $R^8$ are both hydrogen.

4. The compound of claim 3, wherein $R^{15}$ is selected from methyl, ethyl, hydroxymethyl, and 2-hydroxyethyl.

5. The compound of claim 1, wherein $R^5$ is hydrogen.

6. The compound of claim 1, wherein L and Q are absent.

7. The compound of claim 1, wherein $R^6$ is an N-terminal protecting group.

8. The compound of claim 7, wherein $R^6$ is selected from t-butoxycarbonyl and benzyloxycarbonyl.

9. The compound of claim 1, wherein the carbon bearing $R^1$ has a D stereochemical configuration.

10. The compound of claim 9, wherein $R^1$ is selected from methyl, ethyl, isopropyl, carboxymethyl, and benzyl.

11. The compound of claim 1, wherein $R^2$ is selected from $C_{1-6}$alkyl-phenyl, $C_{1-6}$alkyl-indolyl, $C_{1-6}$alkyl-thienyl, $C_{1-6}$alkyl-thiazolyl, and $C_{1-6}$alkyl-isothiazolyl.

12. The compound of claim 1, wherein $R^2$ is selected from

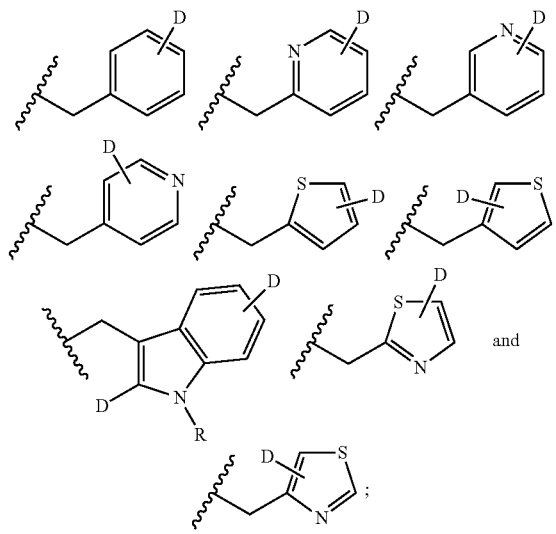

wherein D is selected from hydrogen, methoxy, t-butoxy, hydroxy, cyano, trifluoromethyl, and $C_{1-4}$alkyl, wherein $C_{1-4}$alkyl may be substituted or not with substituents selected from the group consisting of a halogen, a hydroxyl, a carbonyl, a thiocarbonyl, an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety; and R is hydrogen or a suitable protecting group.

13. The compound of claim 1, wherein $R^3$ is selected from $C_{1-6}$alkyl-phenyl and $C_{1-6}$alkyl-indolyl.

14. The compound of claim 13, wherein $R^3$ is selected from

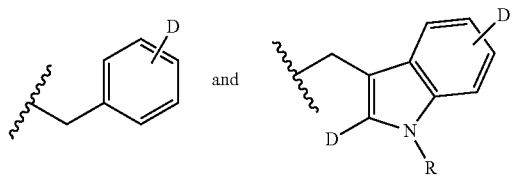

wherein D is selected from hydrogen, methoxy, t-butoxy, hydroxy, cyano, trifluoromethyl, and $C_{1-4}$-alkyl, wherein $C_{1-4}$-alkyl may be substituted or not with substituents selected from the group consisting of a halogen, a hydroxyl, a carbonyl, a thiocarbonyl, an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety; and R is hydrogen or a suitable protecting group.

15. The compound of claim 1, wherein $R^6$ is selected from heterocyclylMZAZ-$C_{1-8}$alkyl-, heterocyclylM-, and carbocyclylM-.

16. The compound of claim 15, wherein $R^6$ is heterocyclylMZAZ-$C_{1-8}$alkyl-, and heterocyclylM-.

17. The compound of claim 1, wherein L is C=O, Q is absent, M is $C_{1-8}$alkyl and $R^6$ is heterocyclylM- and the heterocyclyl moiety is selected from morpholino, piperidino, piperazino, and pyrrolidino.

18. The compound of claim 17, wherein L is C=O, Q is absent, M is $C_{1-8}$alkyl and $R^6$ is heterocyclylM- and the heterocyclyl moiety is morpholino.

19. The compound of claim 1, wherein an $EC_{50}$ ratio of the compound in an assay of constitutive proteasome activity as compared to the $EC_{50}$ of the compound in an assay of immunoproteasome activity is greater than 1.0.

20. The compound of claim 19, wherein the $EC_{50}$ ratio is greater than 3.0.

21. A pharmaceutical composition, comprising a pharmaceutically acceptable carrier or diluent and a compound of claim 1, or a pharmaceutically acceptable salt thereof.

22. The pharmaceutical composition of claim 21, wherein L is C=O, Q is absent, M is $C_{1-8}$alkyl and $R^6$ is heterocyclylM- and the heterocyclyl moiety is morpholino.

* * * * *

UNITED STATES PATENT AND TRADEMARK OFFICE
CERTIFICATE OF CORRECTION

| | |
|---|---|
| PATENT NO. | : 8,357,683 B2 |
| APPLICATION NO. | : 13/328909 |
| DATED | : January 22, 2013 |
| INVENTOR(S) | : Kevin D. Shenk |

It is certified that error appears in the above-identified patent and that said Letters Patent is hereby corrected as shown below:

On the Title Page, Col. 1, line 2, delete "San Francesco, CA" and insert -- San Francisco, CA --

In the Claims:

Column 108, line 15, claim 14, delete "$C_{1-4}$-alkyl," and insert -- $C_{1-4}$alkyl, --

Column 108, line 16, claim 14, delete "$C_{1-4}$-alkyl" and insert -- $C_{1-4}$alkyl --

Signed and Sealed this
Seventh Day of May, 2013

Teresa Stanek Rea
*Acting Director of the United States Patent and Trademark Office*